(12) United States Patent
Koong et al.

(10) Patent No.: US 8,372,861 B2
(45) Date of Patent: Feb. 12, 2013

(54) INHIBITORS OF THE UNFOLDED PROTEIN RESPONSE AND METHODS FOR THEIR USE

(75) Inventors: Albert C. Koong, Los Altos, CA (US); Douglas E. Feldman, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1039 days.

(21) Appl. No.: 12/280,793

(22) PCT Filed: Feb. 27, 2007

(86) PCT No.: PCT/US2007/062917
§ 371 (c)(1),
(2), (4) Date: Jan. 9, 2009

(87) PCT Pub. No.: WO2007/101224
PCT Pub. Date: Sep. 7, 2007

(65) Prior Publication Data
US 2009/0312362 A1    Dec. 17, 2009

Related U.S. Application Data

(60) Provisional application No. 60/777,458, filed on Feb. 27, 2006.

(51) Int. Cl.
*A61K 31/435* (2006.01)
*C07D 221/04* (2006.01)
(52) U.S. Cl. ........................ 514/299; 546/112
(58) Field of Classification Search .................. 546/112; 514/229, 299
See application file for complete search history.

(56) References Cited

U.S. PATENT DOCUMENTS

| | | | |
|---|---|---|---|
| 4,172,896 | A | 10/1979 | Uno et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,731,000 | A | 3/1998 | Ruff et al. |
| 5,763,493 | A | 6/1998 | Ruff et al. |
| 5,958,703 | A | 9/1999 | Dower et al. |
| 6,110,973 | A | 8/2000 | Young |
| 2003/0049701 | A1 | 3/2003 | Muraca |
| 2003/0224428 | A1 | 12/2003 | Ron et al. |
| 2006/0041006 | A1 | 2/2006 | Ibrahim et al. |
| 2006/0247320 | A1 | 11/2006 | Tagat et al. |

FOREIGN PATENT DOCUMENTS

WO      2007101224 A2      9/2007

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Dorwald F. A. Side Reactions in Organic Synthesis, 2005, Wiley: VCH, Weinheim pg. IX of Preface.*
Bakhite et al . English abstract DN 133:309854 2000.*
Perola, et al., "Successful Virtual Screening of a Chemical Database for Farnesyltransferase Inhibitor Leads," Jounal of Medicinal Chemistry, 2000, vol. 43, No. 3, 401-408.
Iwawaki, et al., "A transgenic mouse model for monitoring endoplasmic reticulum stress," Nature Medicine, Jan. 2004, vol. 10, No. 1, 98-102.
Kaufman, "Orchestrating the unfolded protein response in health and disease," The Journal of Clinical Investigation, Nov. 2002, vol. 110, No. 10, 1389-1398.
Zhang et al., "Signaling the Unfolded Protein Response from the Endoplasmic Reticulum," The Journal of Biological Chemistry, Jun. 18, 2004, vol. 279, No. 25, 25935-25938.
Garber, "Researchers Target Unfolded Protein Response in Cancerous Tumor Growth," Journal of the National Cancer Institute, Apr. 19, 2006, vol. 98, No. 8, 512-514.
Feldman, et al., "The Unfolded Protein Response: A Novel Component of the Hypoxic Stress Response in Tumors," Mol Cancer Res, Nov. 2005, vol. 3, No. 11, 597-605.
Search Report and Written Opinion of the International Searching Authority, application No. PCT/US07/62917, mailed Aug. 14, 2008.
Search Report and Written Opinion of the International Searching Authority, application No. PCT/US07/62918, mailed Sep. 30, 2008.

* cited by examiner

*Primary Examiner* — Rita Desai
(74) *Attorney, Agent, or Firm* — David J. Aston; Peters Verny, LLP

(57) ABSTRACT

Compounds that are inhibitors of the unfolded protein response and endonuclease IRE1 are provided, together with compositions comprising such compounds, and methods for their use in the treatment of various disorders, such as cancer, autoimmune disorders, and diabetes. Also provided are packaged pharmaceuticals comprising these compositions. The compositions may be administered in combination with another therapeutic agent.

18 Claims, 27 Drawing Sheets

IRESTATIN 9389

LEFT TUMOR: XBP-luci
RIGHT TUMOR: CMV-luci

INHIBITORS OF THE UNFOLDED PROTEIN RESPONSE AND METHODS FOR THEIR USE

CROSS-REFERENCE TO RELATED APPLICATIONS

This application is a national phase application of PCT International Patent Application PCT/US2007/062917, filed Feb. 27, 2007, which claims the benefit of U.S. Provisional Application No. 60/777,458, filed Feb. 27, 2006, the disclosures of which are incorporated herein by reference in their entireties.

STATEMENT REGARDING FEDERALLY SPONSORED RESEARCH OR DEVELOPMENT

This invention was made in part with government support under PHS Grant No. 1R01CA112108-01A1, awarded by the National Institutes of Health. The government may have certain rights in the invention.

FIELD OF THE INVENTION

The present invention relates generally to compounds, compositions, and packaged pharmaceuticals useful in the treatment of disorders characterized by cell growth in hypoxic conditions, such as cancers, in particular solid tumors. More specifically, the invention relates to compounds, compositions, and packaged pharmaceuticals that inhibit the activity of IRE1. The invention also relates to methods for inhibiting the unfolded protein response, for inhibiting IRE1, and for treating or preventing disorders associated with the unfolded protein response.

BACKGROUND OF THE INVENTION

A defining feature of solid tumors is their capacity to divide aggressively and disseminate metastases under conditions of nutrient deprivation and limited oxygen availability. These severe stresses arise from inadequate perfusion as the primary tumor rapidly outgrows its initial blood supply, and from dramatic structural abnormalities of tumor vessels that can lead to disturbed microcirculation (Hockel and Vaupel, *Semin. Oncol.* 28(2 Suppl 8):36-41, 2001; Vaupel, et al. *Med. Oncol.* 18:243-59, 2001). As a result, regions of low $O_2$ tension, or hypoxia, are heterogeneously distributed within the tumor mass. While tumor hypoxia is a physiological barrier to cell survival, it paradoxically drives malignant progression by imposing a powerful selective pressure for cells that can best adapt to this stress and subsequently resume cell division.

Tumor hypoxia also correlates with a more aggressive disease course and increased failure following radiation and chemotherapy. The presence of hypoxia has been demonstrated in a wide variety of human cancers, including cervix, breast, lung, brain, pancreas, head and neck, and prostate (Evans S., & Koch C. *Cancer Lett.* 195:1-16, 2003). Many of these tumors contained regions of severe hypoxia (<5 mmHg oxygen). Clinically, the duration of disease- and progression-free survival correlates inversely with the degree of tumor hypoxia. For example, in patients with squamous carcinoma of the head and neck, the one year disease-free survival was 78% for patients with median tumor pO2>10 mm Hg but only 22% for median pO2<10 mm (Brizel, et al., *Int. J. Radiat. Oncol. Biol. Phys.* 38:285-9, 1997). Hypoxic cells also exhibit increased resistance to standard radiation and chemotherapy treatment programs, as these cells are relatively isolated from the blood supply and because radiation and chemotherapy preferentially kill rapidly dividing cell populations. Collectively, these findings provide strong evidence that hypoxia has a profound impact on tumor growth and clinical outcome.

Hypoxia dramatically reshapes cellular physiology, causing cell cycle arrest, a shift in energy production to glycolysis, elevated secretion of survival and pro-angiogenic factors, expression of genes involved in drug resistance, and increased cell motility and invasion. A watershed discovery linking these profound changes to the control of gene expression was made with the identification of hypoxia-inducible factor (HIF), a heterodimeric transcription factor that exerts control over a broad range of cellular pathways including glycolysis, angiogenesis and erythropoiesis (Semenza, *Trends Mol. Med.* 2002 8(4 Suppl):S62-7, 2002; Semenza, *Nat. Rev. Cancer* 3:721-32, 2003).

While HIF controls the expression of more than 60 genes and constitutes a key node in cellular stress signaling, HIF activation alone cannot account for the full repertoire of changes that occur intracellularly as oxygen becomes limiting. The hypoxic cell also elicits additional, HIF-1-independent, adaptive responses that contribute to increased survival under low oxygen conditions. For example, an immediate reaction to hypoxia is a reduction in the rates of global protein synthesis, which reduces energy demands when oxygen and ATP levels are low (Hochachka et al., *Proc. Natl. Acad. Sci. USA*, 93:9493-8, 1996). Further, hypoxia causes a sharp increase in the expression of molecular chaperones, which assist in protein refolding and in the degradation of terminally misfolded conformers. Underlying these changes is a coordinated cellular program called the unfolded protein response (UPR) that serves as a master regulator of cellular homeostasis and which plays a fundamental cytoprotective role during cellular stresses such as hypoxia.

The endoplasmic reticulum (ER) is an extensive intracellular membrane network that extends throughout the cytoplasm and functions primarily to process newly synthesized secretory and transmembrane proteins. Accumulation of unfolded proteins in this compartment causes ER stress, with prolonged ER stress resulting in cell death. The cellular response to ER stress consists of at least two coordinated pathways: 1) rapid translational arrest mediated by PERK (pancreatic ER kinase or PKR-like ER kinase); and 2) transcriptional activation of unfolded protein response (UPR) target genes (Ron D. *J. Clin. Invest.* 110:1383-1388, 2002; Harding H., et al. *Annu. Rev. Cell. Dev. Biol.* 18:575-599, 2002; Feldman D. E., et al. *Mol. Cancer Res.* 3:597-605, 2005). In addition to solid tumors, the UPR has been implicated in diseases such as conformational diseases, diabetes, cardiovascular disease, atherosclerosis, viral infection, and cerebrovascular disease (Schroder M., et al. *Mutat. Res.* 569: 29-63, 2005; Kaufman R. *J. Clin. Invest.* 110:1389-1398, 2002).

During normal embryonic development, activation of the UPR is essential for the maturation of secretory cells in the liver and pancreas, and drives an expansion of the ER in antibody-secreting B lymphocytes to accommodate increased secretory load. Iwakoshi et al., *Immunological Reviews* 194: 29-38 (2003); Harding et al., *Molecular Cell* 5: 897-904 (2000); Shaffer et al., *Immunity* 21: 81-93 (2004); Reimold et al., *Genes Dev* 14: 152-157 (2000). Several lines of evidence have also implicated the UPR in various disease processes, such as diabetes and cardiovascular disease, and as a survival mechanism underlying tumor growth and the adaptation of malignant cells to hypoxic stress. Ma and Hendershot, *Nat Rev Cancer* 4: 966-977 (2004); Feldman et al., *Mol Cancer Res* 3: 597-605 (2005); Koumenis, *Curr Mol Med* 6: 55-69 (2006).

A critical feature of malignant tumors is their capacity to survive and seed distant metastases under conditions of nutrient deprivation and limited oxygen availability. Hockel and Vaupel, *Seminars in Oncology* 28: 36-41 (2001); Vaupel et al., *Methods in Enzymology* 381: 335-354 (2004); Subarsky and Hill, *Clin Exp Metastasis* 20: 237-250 (2003). Intratumoral hypoxia arises solid tumors through severe structural abnormalities of tumor vasculature and disturbed microcirculation, resulting in tissue regions of extremely low $O_2$ partial pressures distributed heterogeneously within the tumor mass. Vaupel et al., *Methods in Enzymology* 381: 335-354 (2004); Hockel and Vaupel, *Journal of the National Cancer Institute* 93: 266-276 (2001); Vaupel et al., *Medical Oncology* 18: 243-259 (2001). Since the delivery of oxygen and nutrients to the tumor is determined by fluctuating blood flow, different regions of the tumor must constantly adjust to varying degrees of nutrient deprivation. The tumor microenvironment thus imposes a strong selective pressure for cells best adapted for survival under these stresses. Adaptation to hypoxia contributes to the diminished apoptotic potential of tumor cells and accounts for many of the clinical consequences of malignant progression, including locoregional tumor recurrence and distant metastases. Evans and Koch, *Cancer Letters* 195: 1-16 (2003); Le et al., *Cancer Metastasis Rev* 23: 293-310 (2004). Hypoxia-mediated clonal expansion of cells with diminished apoptotic potential has been demonstrated in vitro, and hypoxic cells exhibit increased metastatic potential. Erler et al., *Nature* 440: 1222-1226 (2006); Graeber et al., *Nature* 379: 88-91 (1996). Importantly, depletion of molecular oxygen or glucose impairs the posttranslational modification and oxidative folding of secretory proteins, providing a direct biochemical link between nutrient deprivation in tumors and activation of the UPR. Tu et al., *Science* 290: 1571-1574 (2000); Koumenis et al., *Molecular & Cellular Biology* 22: 7405-7416 (2002).

PERK, an ER transmembrane protein, was first identified as regulating translational attenuation during ER stress through the phosphorylation of translation initiation factor eIF2α. While most mRNA translation is repressed following phosphorylation of eIF2α, activating transcription factor 4 (ATF4) is selectively translated during ER stress leading to increased expression of chaperones, foldases, and downstream targets such as CHOP/GADD153, a pro-apoptotic gene. Koumenis et al demonstrated that translational control of protein synthesis during hypoxia also occurs through the activation of PERK. These investigators showed that PERK -/- MEFs where unable to phosphorylate eIF2α and had decreased survival after exposure to hypoxia compared to the wild-type MEFs. They concluded that PERK plays an important role in hypoxia-induced translation attenuation, further supporting a role for hypoxia in the development of ER stress (Koumenis et al., *Mol. Cell. Biol.* 22:7405-7416 (2002)). A rapid decrease in de novo protein synthesis upon exposure to hypoxia has also been observed (Chen et al., *Cancer Res.* 64:7302-7310 (2004)). Downstream of PERK, ATF4 is also activated by hypoxia in a HIF-1 independent manner. One consequence of ATF4 activation is induction of a GADD34 which feeds back to desphosphorylate eIF2α and release cells from translational inhibition.

In coordination with the inhibition of protein synthesis, the UPR is also responsible for the transcriptional activation of a discrete set of genes. These genes function to increase the cellular folding capacity through the induction of ER chaperone proteins and folding enzymes. The UPR is a conserved stress response and many of its downstream target genes have been characterized in yeast and mammalian cells. In mammalian cells, activating transcription factor 6 (ATF6) and X-box binding protein (XBP1) are critical regulators of the transcriptional response to ER stress.

The ER resident transmembrane protein IRE1 is conserved throughout eukaryotic phylogeny and functions as both a proximal sensor of ER stress and as a critical UPR signal transducer via its dual cytoplasmic kinase and endoribonuclease domains. Tirasophon et al., *Genes Dev* 12: 1812-1824 (1998). Mammalian IRE1α, the major functional homolog of yeast IRE1α, excises a 26-nucleotide intron from the mRNA encoding the bZIP transcription factor XBP-1. This introduces a translational frame shift downstream of the splice site to generate XBP-1s, a potent transcription factor. Yoshida et al., *Cell* 107: 881-891 (2001); Calfon et al., *Nature* 415: 92-96 (2002); Lee et al., *Genes & Development* 16: 452-466 (2002). XBP-1s drives an expansion of ER capacity through the increased expression of molecular chaperones and components of the ER-associated protein degradation (ERAD) machinery that is required for the clearance of terminally misfolded proteins. Schroder and Kaufman, *Mutation Research* 569: 29-63 (2005); Lee et al., *Molecular & Cellular Biology* 23: 7448-7459 (2003). IRE1α is extensively activated in hypoxic regions of human tumor xenografts throughout tumorigenesis (Feldman et al., *Mol Cancer Res* 3: 597-605 (2005)), and transformed mouse fibroblasts genetically deleted for XBP-1 exhibit increased sensitivity to hypoxia and fail to grow as tumors when implanted into immune-deficient mice (Romero-Ramirez et al., *Cancer Research* 64: 5943-5947 (2004)). Activation of IRE1α by ER stress triggers multiple signaling outputs that extend beyond the splice-activation of XBP-1, including IRE1α endonuclease-mediated cleavage of a subset of mRNAs encoding secretory proteins (Hollien and Weissman, *Science* 313: 104-107 (2006)), and activation of autophagy and apoptosis pathways through the IRE1α kinase domain and its downstream effectors caspase-12, ASK1, and JNK1 (Ogata et al., *Mol Cell Biol* (2006); Urano et al., *Science* 287: 664-666 (2000)). Thus IRE1α may participate in both cytoprotective and pro-apoptotic pathways.

A schematic of the UPR pathway is shown in FIG. 1. In this model, GRP78 regulates each of the major branches of the UPR by direct association with ATF6, IRE1 and PERK. Given its importance in regulating the UPR, GRP78 levels can be increased by downstream signaling from each of these pathways, indicating that significant overlap occurs in activation of the UPR.

The functional link between the UPR and hypoxia was found through studies on GRP78, a critical regulator of the UPR. Expression of the glucose regulated family of proteins (GRPs) within solid tumors was recognized more than a decade ago. These experiments indicate that glucose starvation and hypoxia were physiologically relevant stresses occurring during the growth of solid tumors (Cai J., et al., *J. Cell. Physiol.* 154:229-237, 1993). Furthermore, cells in which GRP78 expression was inhibited through an antisense strategy exhibited increased sensitivity to hypoxia compared to the parental wild-type cell line (Koong A., et al., *Int. J. Radiat. Oncol. Biol. Phys.* 28:661-666, 1994).

Other UPR regulated genes such as GRP94 and protein disulfide isomerase (PDI) have also been implicated in mediating neuronal survival after ischemia/reperfusion injury (Sullivan D., et al., *J. Biol. Chem.* 278:47079-47088, 2003; Bando Y., et al., *Eur. J. Neurosci.* 18, 2003.). Similarly, oxygen regulated protein 150 kDal (ORP150, also known as GRP170), another ER chaperone protein, protected neurons from ischemic stress in a cell culture model and reduced the cerebral infarct area after middle cerebral artery occlusion in a transgenic mouse model (Tamatani M., et al., *Nat. Med.* 7:317-323, 2001).

These studies indicate that the UPR has a broad range of functions during hypoxia including promotion of cell survival and regulation of angiogenesis. Given its role in regulating survival under hypoxia and its requirement for tumor growth, targeting XBP-1 may be an effective therapeutic strategy. However, there are currently few examples of anti-cancer drugs that can effectively inhibit transcription factor activation. There thus remains a need for compositions that may be employed to inhibit the activity of XBP-1 and thereby prevent or inhibit tumor growth.

Identification of compounds capable of inhibiting the activity of XBP-1 and thereby capable of preventing or inhibiting tumor growth would be facilitated by assays suitable for use in high throughput screens. Direct measurement of XBP-1 levels in cells is not easily automated. Convenient and easily detectable substrates for the endonuclease or kinase activities of IRE1 are currently unavailable. US Patent Application No. 2003/0224428 reports methods purportedly useful in screening inhibitors of IRE1-mediated processing of untranslatable XBP-1 mRNA. The reported methods are limited to the screening of plasma cells or virus-infected cells, however, and are therefore unsuitable for identifying compounds useful in the treatment or prevention of disorders in more general cell types and tissues. The methods also fail to account for the effects of tumor microenvironment, such as, for example, hypoxia, on the activity of potential therapeutic compounds. The methods also lack steps to counterscreen for compounds causing non-specific effects on the detectable marker and for compounds that are toxic to cells even in the absence of ER stress. The methods would therefore falsely identify compounds that have nothing to do with the UPR and that would be unsuitable for therapeutic use. Furthermore, the methods have not been shown to be suitable for use in high throughput screening assays.

Due to the importance of the unfolded protein response in cellular metabolism, and, in particular, in pathological processes, there is great interest in developing inhibitors with defined specificities against this process. Such inhibitors can help to identify target enzymes in cells, particularly where the cells are associated with particular indications, and can provide new drug candidates. There is thus a need for inhibitors of the unfolded protein response and novel methods of inhibiting this pathway, as well as methods of treating or preventing disorders of the unfolded protein response and methods of identifying novel inhibitors of the pathway.

SUMMARY OF THE INVENTION

The present invention addresses these problems by providing novel inhibitors of the unfolded protein response, compositions, packaged pharmaceuticals, and methods of use thereof.

In one aspect, the invention provides compounds represented by structural formula (I):

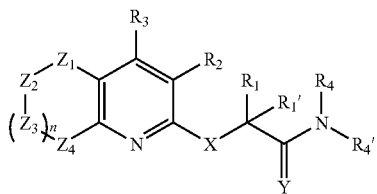

(I)

or a pharmaceutically acceptable derivative or prodrug thereof, wherein:
X is O, S, or N—$R_4''$;
Y is O or S;

$Z_1$, $Z_2$, $Z_3$, and $Z_4$ are independently $C(R_6)(R_6')$ or $NR_4''$, provided that only one of $Z_1$, $Z_2$, $Z_3$, and $Z_4$ at a time is N—$R_4''$;
n is 0-2;
$R_1$, $R_1'$, $R_6$, and $R_6'$ are independently hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and are optionally substituted with 1-3 J groups;
$R_2$ is alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;
$R_3$ is alkyl, alkenyl, alkynyl, aralkyl, alkoxy, aryloxy, aralkoxy, cycloalkyl, cycloalkenyl, cycloalkoxy, haloalkyl, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;
$R_1$, $R_1'$, and $R_2$ taken together may form

wherein $R_5$ is hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;
$R_4$, $R_4'$, and $R_4''$ are independently hydrogen, alkyl, alkenyl, alkynyl, aryl, aralkyl, aralkenyl, cycloalkyl, cycloalkenyl, cycloalkoxy, heterocyclyl, heterocyclylalkyl, heteroaryl, heteroaralkyl, formate, formamide, acyl, phosphoryl, sulfonyl, or sulfonamido and are optionally substituted with 1-3 J groups, wherein $R_4$ and $R_4'$ taken together with the N atom to which they are attached complete a cyclic structure having from 4 to 8 atoms in the ring;
J is alkyl, alkenyl, alkynyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J' groups; and
J' is alkyl, alkenyl, alkynyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

provided that when X is S and Y is O;

$R_1$ and $R_1'$ are hydrogen and $R_2$ is CN or $R_1$, $R_1'$, and $R_2$ together form

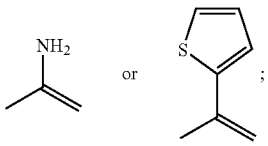

$Z_1$, $Z_3$, and $Z_4$ are $CH_2$, and $Z_2$ is $CH_2$, $NC(O)CH_3$, $CHCH_3$, $CHCH_2CH_3$, $CHCH(CH_3)_2$, $CHCH_2CH(CH_3)_2$, or CH-phenyl;

and $R_3$ is $CH_3$, $CF_3$, i-Bu, Br, C(O)OEt, or CH=CH-phenyl;

then $R_4$ and $R_4'$ are not both hydrogen or ethyl; $R_4$ and $R_4'$ taken together with the N atom to which they are attached do not form a tetrahydroisoquinoline or N-methylpiperazine; and when $R_4$ is hydrogen, $R_4'$ is not $C_{1-4}$ alkyl; $CH_2COOH$; unsubstituted cyclohexyl; unsubstituted naphthyl; unsubstituted adamantyl;

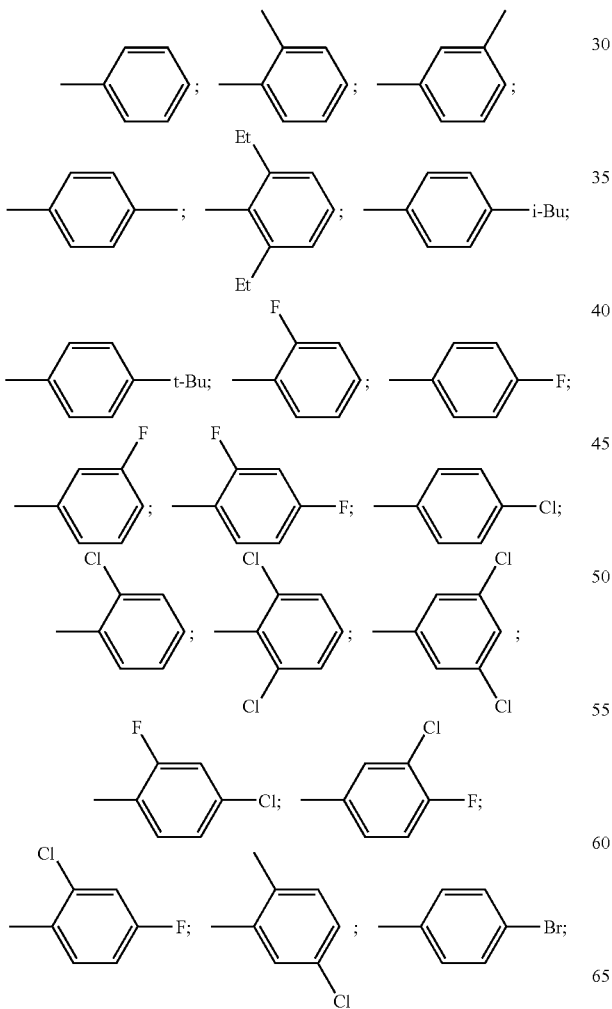

-continued

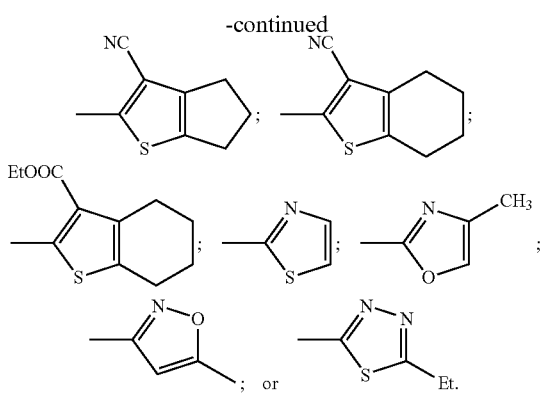

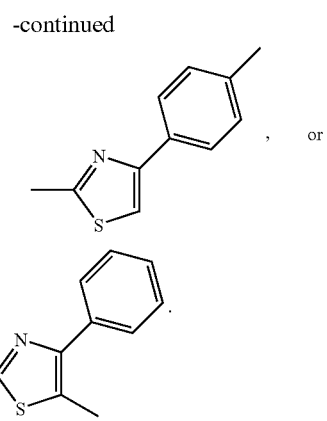

In some embodiments of the invention, $Z_1$, $Z_2$, $Z_3$, and $Z_4$ are $C(R_6)(R_6')$, and n is 0 or 1.

In some embodiments, $R_6$ and $R_6'$ are both hydrogen.

In some embodiments, X is S.

In some embodiments, Y is O.

In some embodiments, $R_3$ is alkyl or haloalkyl.

In other embodiments, $R_3$ is $CF_3$.

In some embodiments, $R_1$ and $R_1'$ are both hydrogen.

In some embodiments, $R_1$ and $R_1'$ are both hydrogen, and $R_2$ is CN.

In some embodiments, $R_1$, $R_1'$, and $R_2$ together form

and in more specific embodiments, $R_5$ is $NH_2$.

In some embodiments, $R_4'$ is hydrogen, and $R_4'$ is an optionally substituted aryl, heteroaryl, aralkyl, or heteroaralkyl.

In specific embodiments, $R_4'$ is an optionally substituted

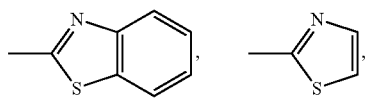

pyridinyl, phenyl, or benzyl.

In even more specific embodiments, $R_4'$ is substituted with one or two $CH_3$, $CH_2CH_3$, CN, $OCH_3$, or phenyl groups.

In still more specific embodiments, $R_4'$ is

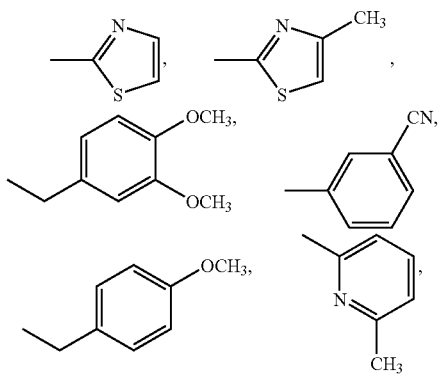

In even more specific embodiments, $R_4'$ is

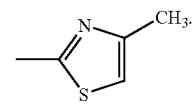

In some embodiments, $R_4$ and $R_4'$ are both alkyl.

In more specific embodiments, $R_4$ and $R_4'$ are both ethyl.

In some embodiments, $Z_2$ is $NR_4''$; and $R_4''$ is $C(O)CH_3$.

In some embodiments, $Z_1$, $Z_2$, $Z_3$, and $Z_4$ are $CR_6R_6'$, n is 0 or 1, X is S, Y is O, $R_1$ and $R_1'$ are hydrogen, $R_2$ is CN, and $R_3$ is $CF_3$.

In specific embodiments, $R_6$ and $R_6'$ are both hydrogen.

In some embodiments, $Z_1$, $Z_2$, $Z_3$, and $Z_4$ are $CR_6R_6'$, n is 0 or 1, X is S, Y is O, $R_1$, $R_1'$, and $R_2$ together form

$R_3$ is $CF_3$, and $R_5$ is $NH_2$.

In specific embodiments, $R_6$ and $R_6'$ are both hydrogen.

In some embodiments, $Z_1$, $Z_2$, $Z_3$, and $Z_4$ are $CR_6R_6'$, n is 0 or 1, X is S, Y is O, $R_3$ is $CF_3$, $R_4$ is hydrogen, and $R_4'$ is

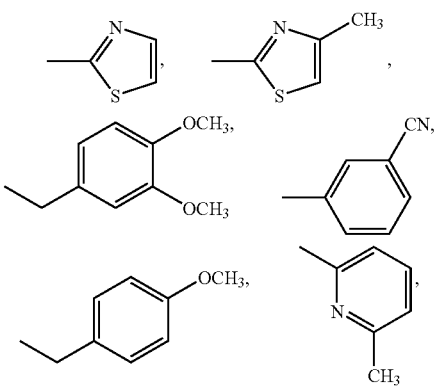

-continued

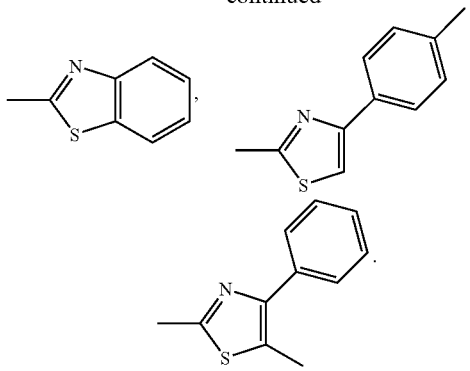

In specific embodiments, $R_6$ and $R_6'$ are both hydrogen.

In some embodiments, $R_1$, $R_1'$, $R_2$, $R_3$, $R_4$, $R_4'$, $R_4''$, $R_5$, J, and J' each independently contains 10 or fewer non-hydrogen atoms.

In specific embodiments, $R_1$, $R_1'$, $R_2$, $R_3$, $R_4$, $R_4'$, $R_4''$, $R_5$, J, and J' each independently contains 6 or fewer non-hydrogen atoms.

In another aspect, the invention provides a pharmaceutical composition comprising a compound represented by structural formula (I):

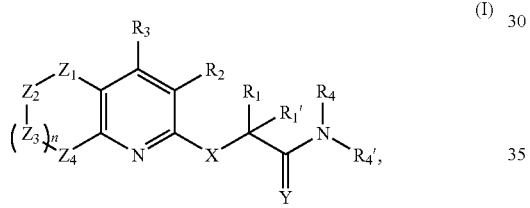

or a pharmaceutically acceptable derivative or prodrug thereof, wherein:

X is O, S, or N—$R_4''$;
Y is O or S;
$Z_1$, $Z_2$, $Z_3$, and $Z_4$ are independently $C(R_6)(R_6')$ or $NR_4''$, provided that only one of $Z_1$, $Z_2$, $Z_3$, and $Z_4$ at a time is N—$R_4''$;
n is 0-2;
$R_1$, $R_1'$, $R_6$, and $R_6'$ are independently hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and are optionally substituted with 1-3 J groups;
$R_2$ is alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;
$R_3$ is alkyl, alkenyl, alkynyl, aralkyl, alkoxy, aryloxy, aralkoxy, cycloalkyl, cycloalkenyl, cycloalkoxy, haloalkyl, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

$R_1$, $R_1'$, and $R_2$ taken together may form

wherein $R_5$ is hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

$R_4$, $R_4'$, and $R_4''$ are independently hydrogen, alkyl, alkenyl, alkynyl, aryl, aralkyl, aralkenyl, cycloalkyl, cycloalkenyl, cycloalkoxy, heterocyclyl, heterocyclylalkyl, heteroaryl, heteroaralkyl, formate, formamide, acyl, phosphoryl, sulfonyl, or sulfonamido and are optionally substituted with 1-3 J groups, wherein $R_4$ and $R_4'$ taken together with the N atom to which they are attached complete a cyclic structure having from 4 to 8 atoms in the ring;

J is alkyl, alkenyl, alkynyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J' groups; and J' is alkyl, alkenyl, alkynyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

and a pharmaceutically acceptable carrier.

In some embodiments, $Z_1$, $Z_2$, $Z_3$, and $Z_4$ are $C(R_6)(R_6')$, and n is 0 or 1.

In specific embodiments, $R_6$ and $R_6'$ are both hydrogen.
In other embodiments, X is S.
In other embodiments, Y is O.
In other embodiments, $R_3$ is alkyl or haloalkyl.
In specific embodiments, $R_3$ is $CF_3$.
In other embodiments, $R_1$ and $R_1'$ are both hydrogen.
In other embodiments, $R_1$ and $R_1'$ are both hydrogen, and $R_2$ is CN.
In still other embodiments, $R_1$, $R_1'$, and $R_2$ together form

In specific embodiments, $R_5$ is $NH_2$.
In some embodiments, $R_4$ is hydrogen; and $R_4'$ is an optionally substituted aryl, heteroaryl, aralkyl, or heteroaralkyl.

In specific embodiments, $R_4'$ is an optionally substituted

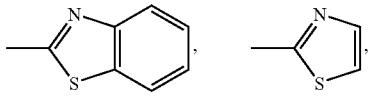

pyridinyl, phenyl, or benzyl.

In more specific embodiments, $R_4'$ is substituted with one or two $CH_3$, $CH_2CH_3$, CN, $OCH_3$, or phenyl groups.

In even more specific embodiments, $R_4'$ is

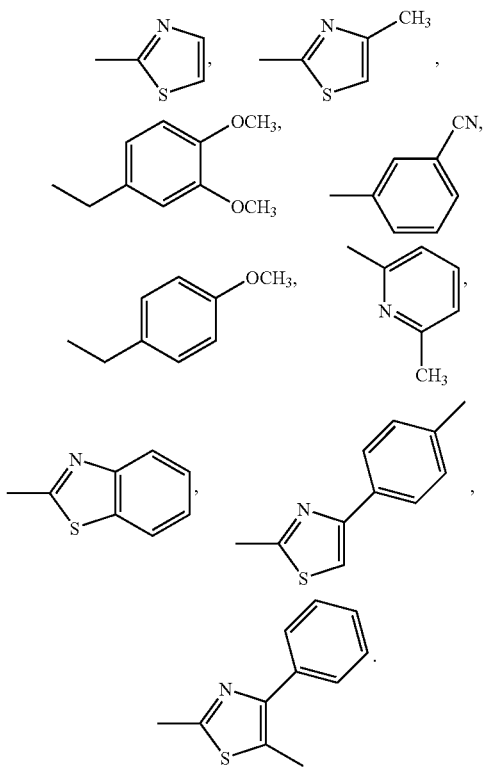

In still more specific embodiments, $R_4'$ is

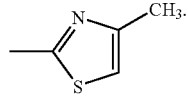

In some embodiments, $R_4$ and $R_4'$ are both alkyl.
In some embodiments, $R_4$ and $R_4'$ are both ethyl.
In some embodiments, $R_1$ and $R_1'$ are both hydrogen.
In some embodiments, $Z_2$ is $NR_4''$, and $R_4''$ is $C(O)CH_3$.
In some embodiments, $Z_1$, $Z_2$, $Z_3$, and $Z_4$ are $CR_6R_6'$, n is 0 or 1, X is S, Y is O, $R_1$ and $R_1'$ are hydrogen, $R_2$ is CN, and $R_3$ is $CF_3$.

In some embodiments, $R_6$ and $R_6'$ are both hydrogen.
In some embodiments, $Z_1$, $Z_2$, $Z_3$, and $Z_4$ are $CR_6R_6'$, n is 0 or 1, X is S, Y is O, $R_1$, $R_1'$, and $R_2$ together form

$R_3$ is $CF_3$, and $R_5$ is $NH_2$.

In specific embodiments, $R_6$ and $R_6'$ are both hydrogen.
In some embodiments, $Z_1$, $Z_2$, $Z_3$, and $Z_4$ are $CR_6R_6'$, n is 0 or 1, X is S, Y is O, $R_3$ is $CF_3$, $R_4$ is hydrogen, and $R_4'$ is

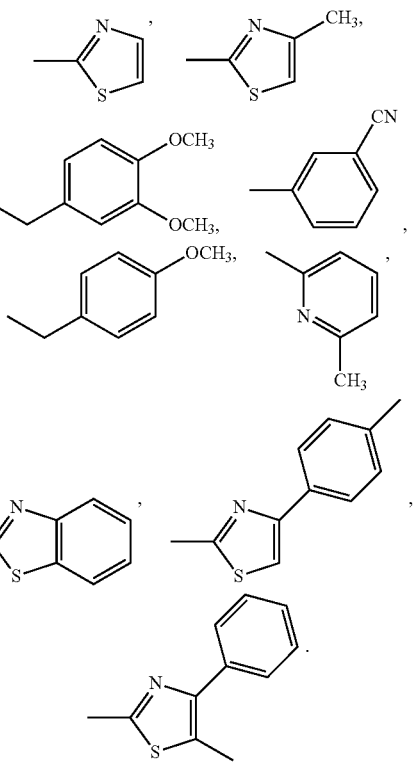

In specific embodiments, $R_6$ and $R_6'$ are both hydrogen.
In some embodiments of the pharmaceutical composition of the invention, the compound is selected from the group consisting of:

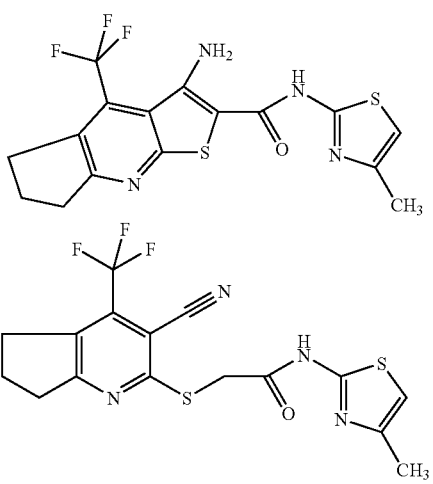

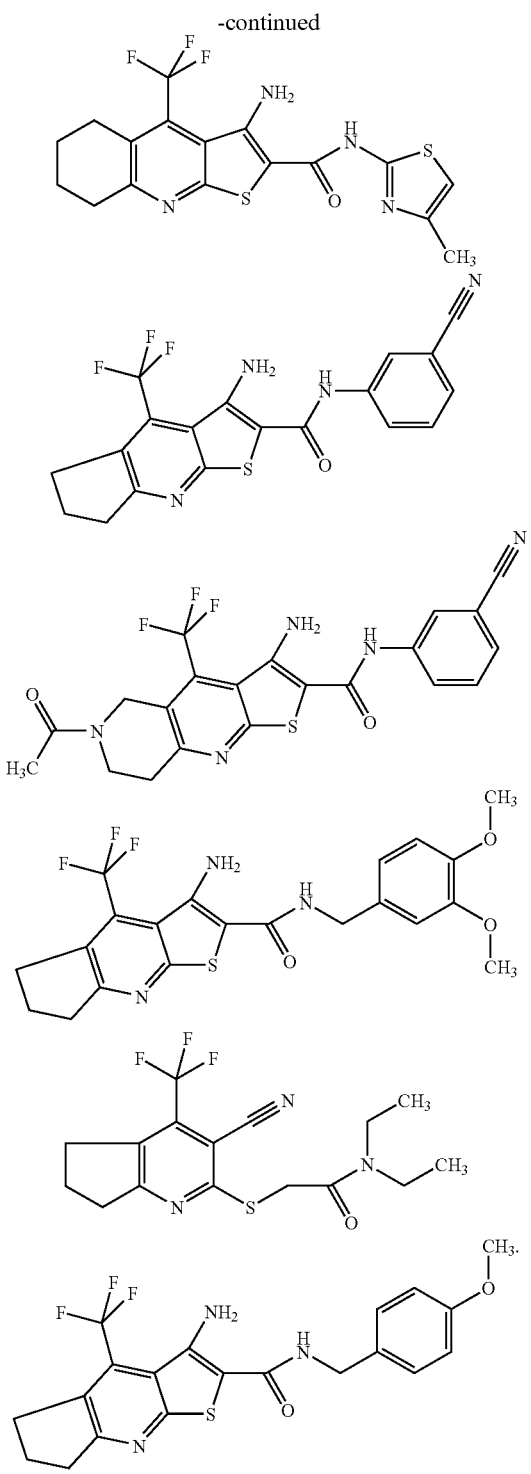

In some embodiments, $R_1$, $R_1'$, $R_2$, $R_3$, $R_4$, $R_4'$, $R_4''$, $R_5$, J, and J' each independently contains 10 or fewer non-hydrogen atoms.

In specific embodiments, $R_1$, $R_1'$, $R_2$, $R_3$, $R_4$, $R_4'$, $R_4''$, $R_5$, J, and J' each independently contains 6 or fewer non-hydrogen atoms.

In another aspect, the invention provides a packaged pharmaceutical comprising any of the above pharmaceutical compositions and instructions for using the composition to inhibit the unfolded protein response in a mammalian host.

In still another aspect, the invention provides methods for inhibiting the unfolded protein response in a mammalian host, comprising administering to the mammalian host in need thereof a therapeutically-effective amount of a pharmaceutical composition of the invention.

In another aspect, the invention provides methods for inhibiting IRE1 in a mammalian host, comprising administering to the mammalian host in need thereof a therapeutically-effective amount of a pharmaceutical composition of the invention.

In yet another aspect, the invention provides methods for treating or preventing a disorder associated with the unfolded protein response in a mammalian host, comprising administering to the mammalian host in need thereof a therapeutically-effective amount of a pharmaceutical composition of the invention.

In some embodiments, the disorder is characterized by uncontrolled cell growth under conditions of hypoxia or ER stress.

In some embodiments, the disorder is selected from the group consisting of cancer, autoimmune disorders, and diabetes.

In some specific embodiments, the cancer is selected from the group consisting of multiple myeloma, cervical cancer, brain cancer, pancreatic cancer, head and neck cancers, prostate cancer, breast cancer, soft tissue sarcomas, primary and metastatic liver cancer, primary and metastatic lung cancer, esophageal cancer, colorectal cancer, lymphoma, and leukemia.

In some embodiments, the cancer is a solid tumor.

In some specific embodiments, the solid tumor is a sarcoma, a carcinoma, or a lymphoma.

In some specific embodiments, the autoimmune disorder is selected from the group consisting of diabetes, lupus, rheumatoid arthritis, psoriasis, multiple sclerosis, and inflammatory bowel disease.

In some specific embodiments, the inflammatory bowel disease is selected from the group consisting of ulcerative colitis and Crohn's disease.

In some embodiments, the autoimmune disorder is rheumatoid arthritis.

In some embodiments, the disorder is cancer, and the method further comprises administration of a chemotherapeutic agent.

In some specific embodiments, the chemotherapeutic agent is selected from the group consisting of bevacizumab, bortezomib, cetuximab, erlotinib, gemcitabine, cisplatin, oxaliplatin, etoposide, adriamycin, taxol, and thalidomide.

The details of various aspects of the invention are set forth in the accompanying drawings and the description below. Other features, objects, and advantages of the invention will be apparent from the description and claims.

LISTING OF DRAWINGS

FIG. 1 is a schematic of the unfolded protein response (UPR) signaling pathway.

FIG. 2A is a schematic of a fusion protein in which unspliced XBP-1 is fused in frame with luciferase. Under hypoxia or ER stress, IRE1 splices a 26 nt sequence in XBP-1 causing a translational frameshift that allows read through of a stop codon, resulting in the production of an XBP-1-luciferase fusion protein. FIG. 2B shows the fold change in luciferase activity (RLU), detected after 24 hours of exposure to hypoxia, when HT1080 cells stably expressing the IRE1 reporter are allowed to reoxygenate.

Figure 5A:
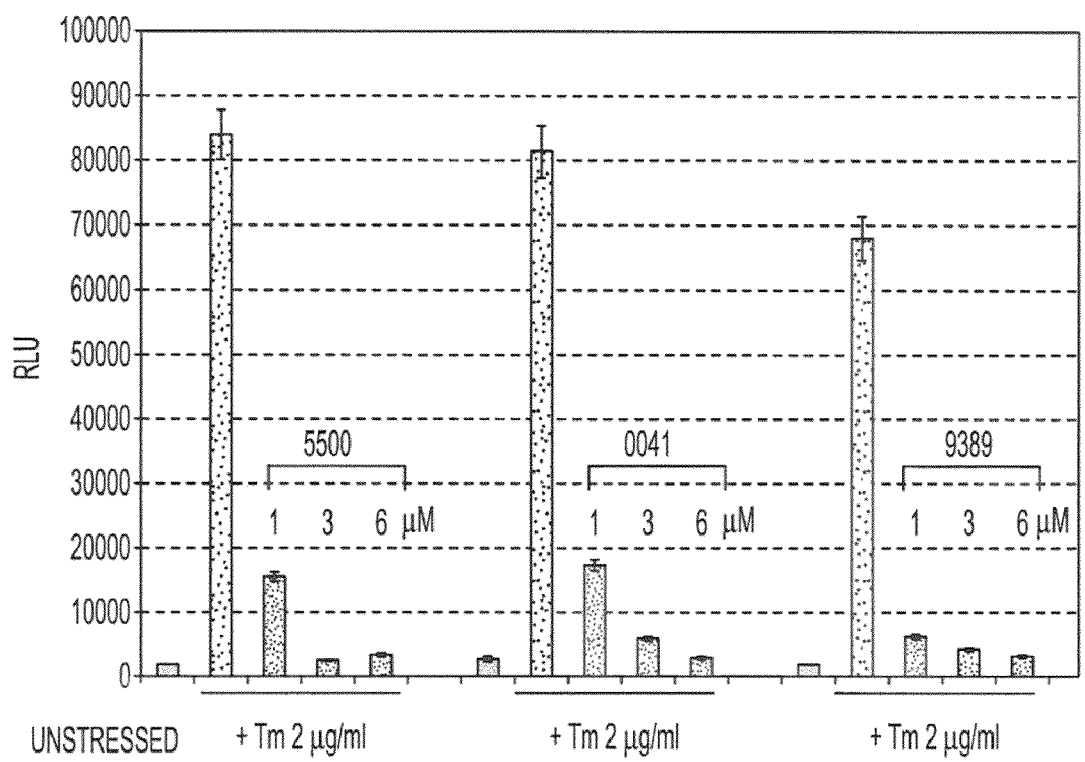
Figure 5B:
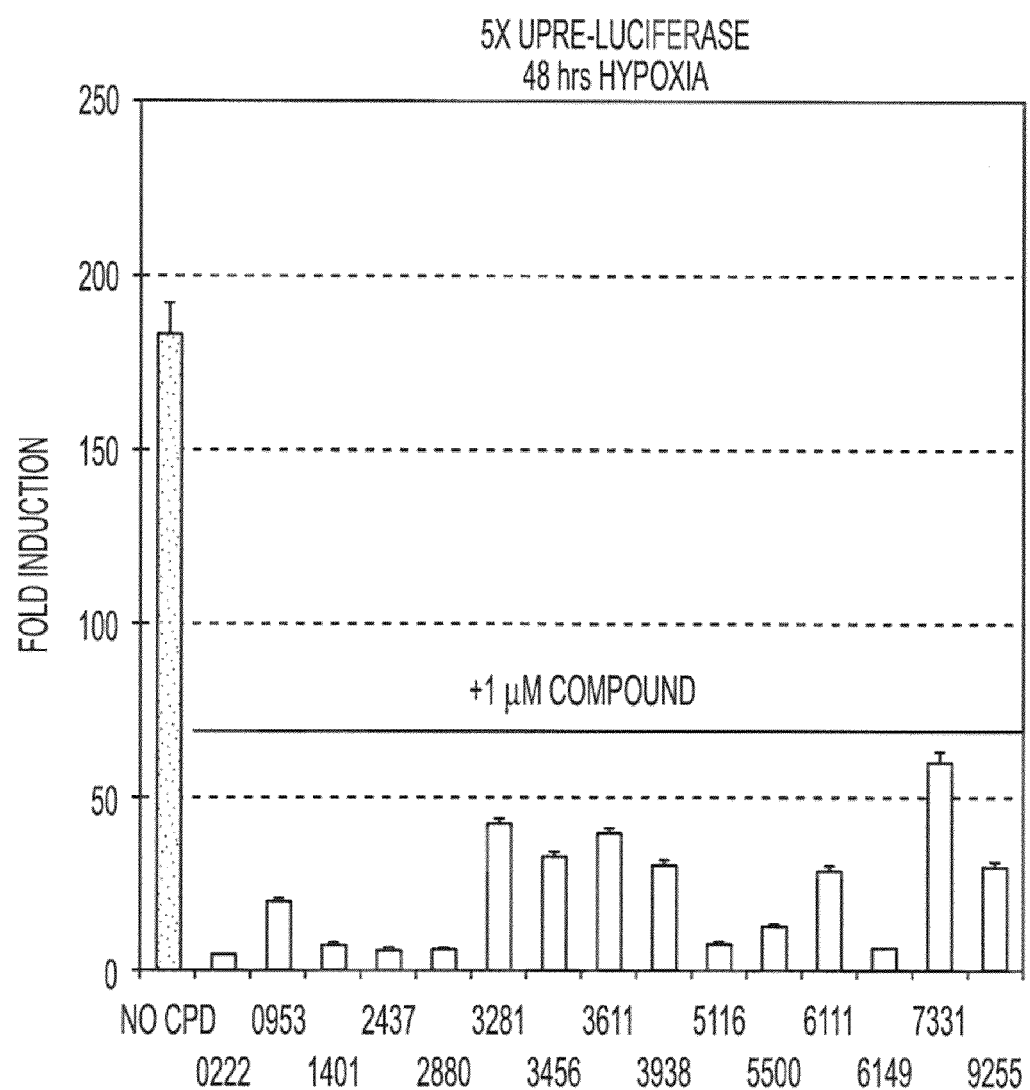

FIG. 5A shows examples of individual compounds tested at 1 uM, 2 uM and 6 uM for inhibition of tunicamycin-(Tm) induced transactivation of a 5 repeat XBP-1 promoter element (5×-UPRE)-luciferase reporter construct transiently transfected into HT1080 cells. FIG. 5B shows individual compounds tested for inhibition of hypoxia (48 hours) induced transactivation of the same UPRE-luciferase report construct transiently transfected into HT1080 cells.

Figure 6A:
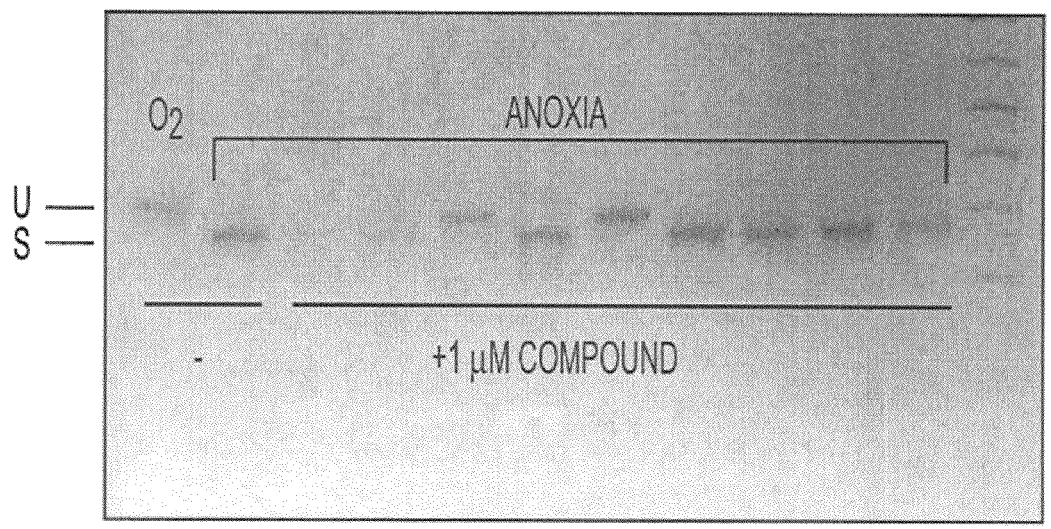
Figure 6B:
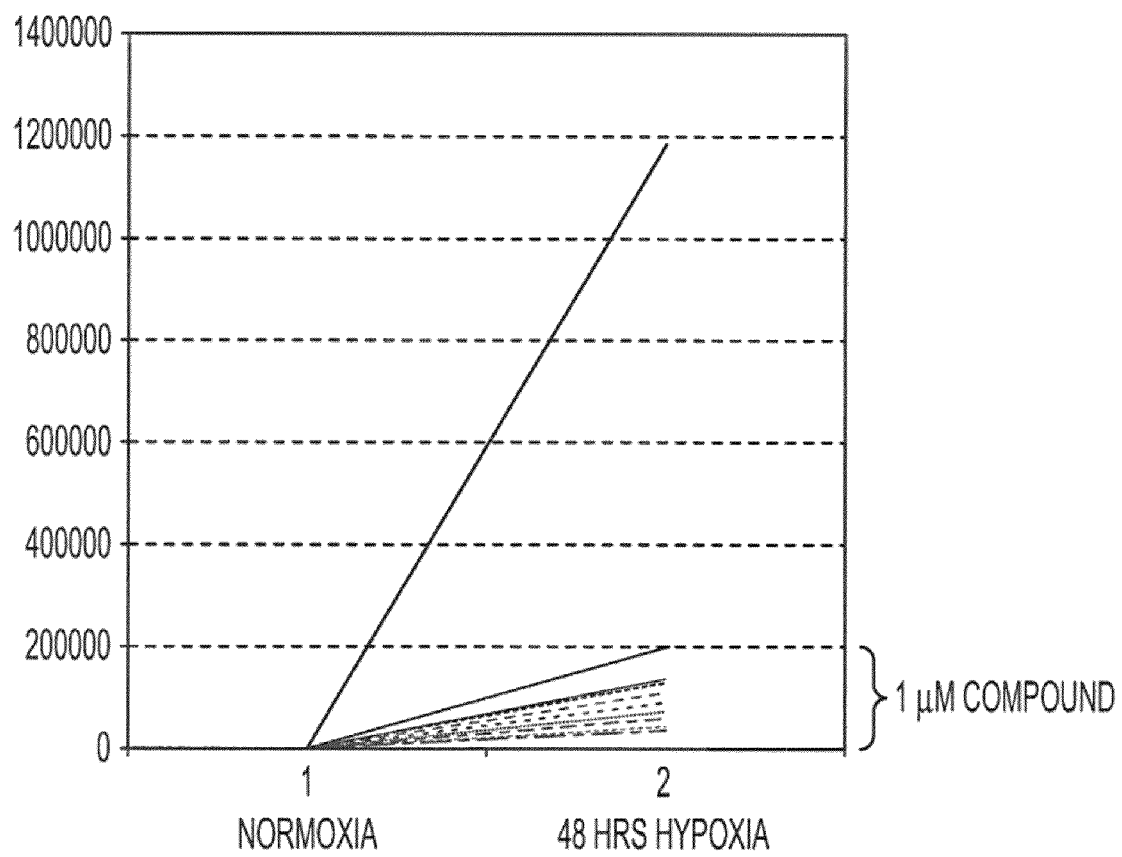

FIG. 6A shows XBP-1 expression as determined by RT-PCR in HT1080 cells treated with hypoxia in the presence of various candidate inhibitors compounds. FIG. 6B shows the inhibition of XBP-luciferase reporter activity in hypoxia by the inventive irestatins. HT1080 fibrosarcoma cells stably expressing the Xbp-luciferase reporter were treated with 1 µM of each Irestatin or left untreated, and incubated in hypoxia (0.01% of oxygen) for 48 hours at 37° C. Cells were harvested, lysed in reporter lysis buffer, and assayed for luminescence using a luminometer.

Figure 7A:
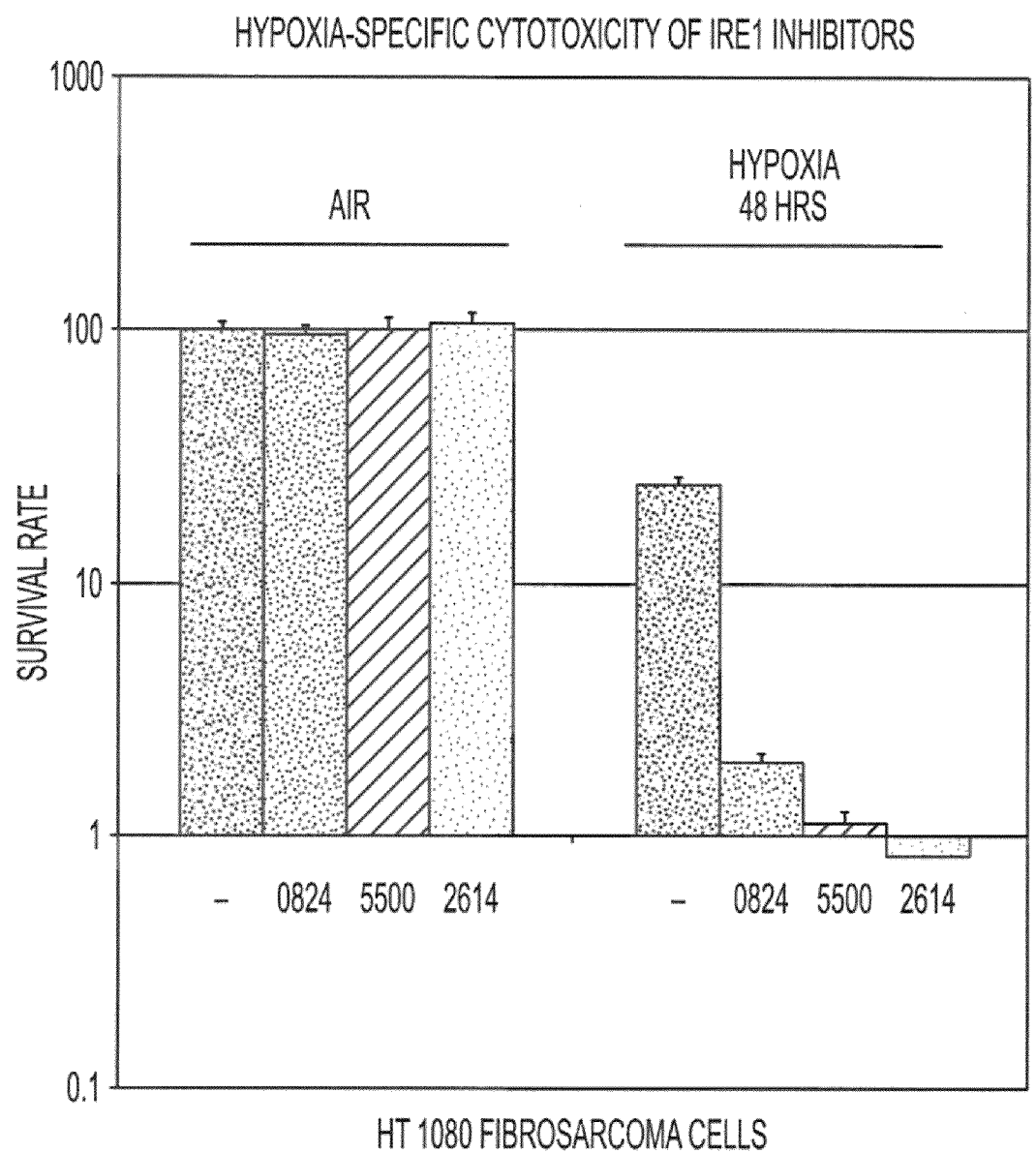
Figure 7B:
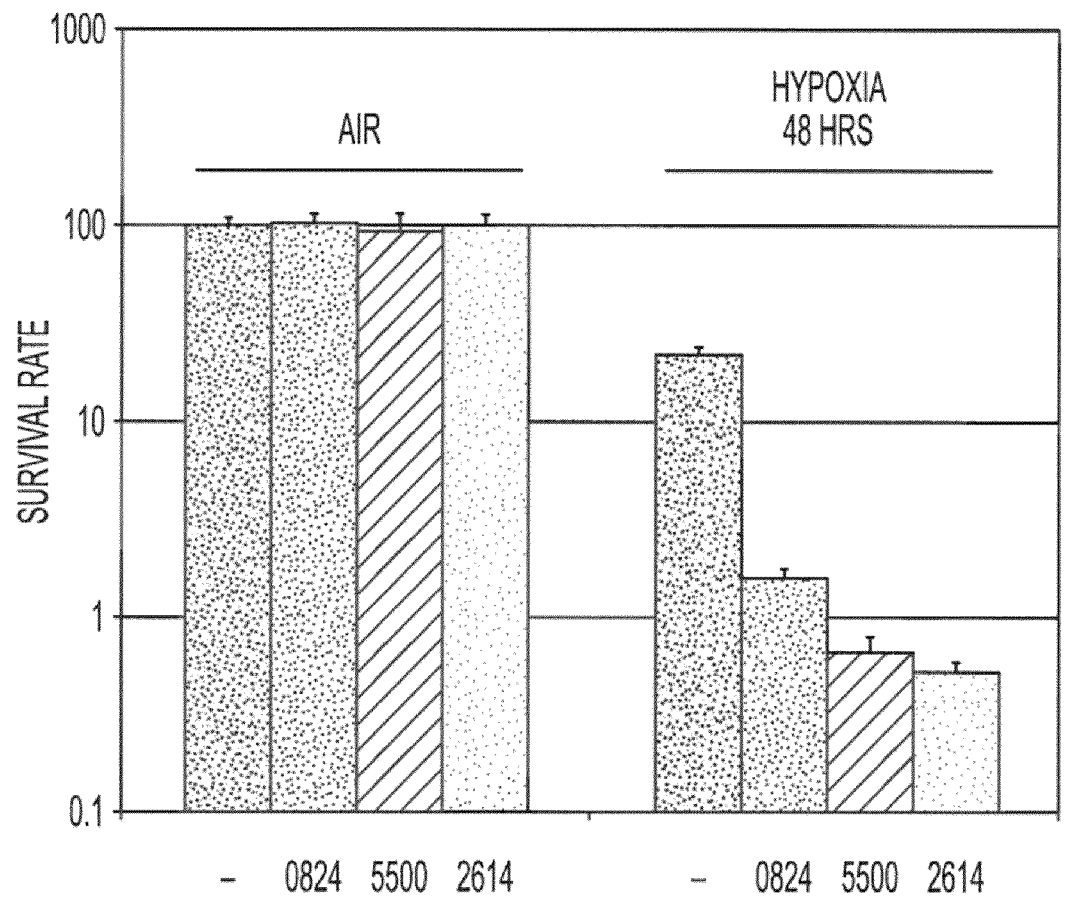
Figure 7C:
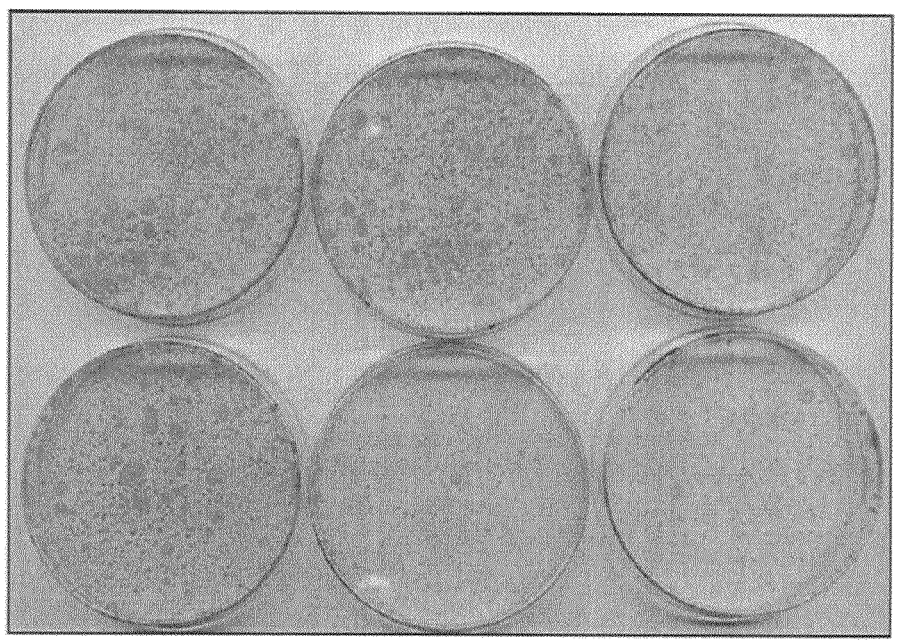

FIGS. 7A and B show the hypoxia-specific cytotoxicity of candidate IRE1 inhibitors on HT1080 sarcoma cells and Mia-PACA-2 cells, respectively, as determined in a clonogenic survival assay. FIG. 7C shows the inhibition of hypoxia survival of human tumor cells by candidate IRE1 inhibitors.

Figure 8:
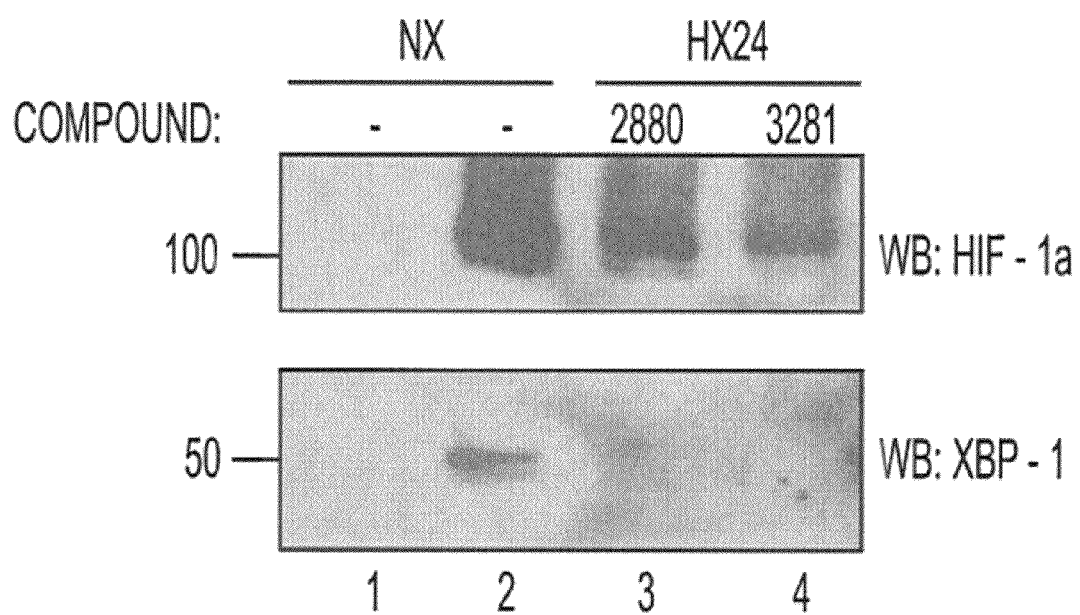

FIG. 8 shows the inhibition of IRE1-mediated XBP-1 splicing in hypoxia by the inventive irestatins.

Figure 9A:
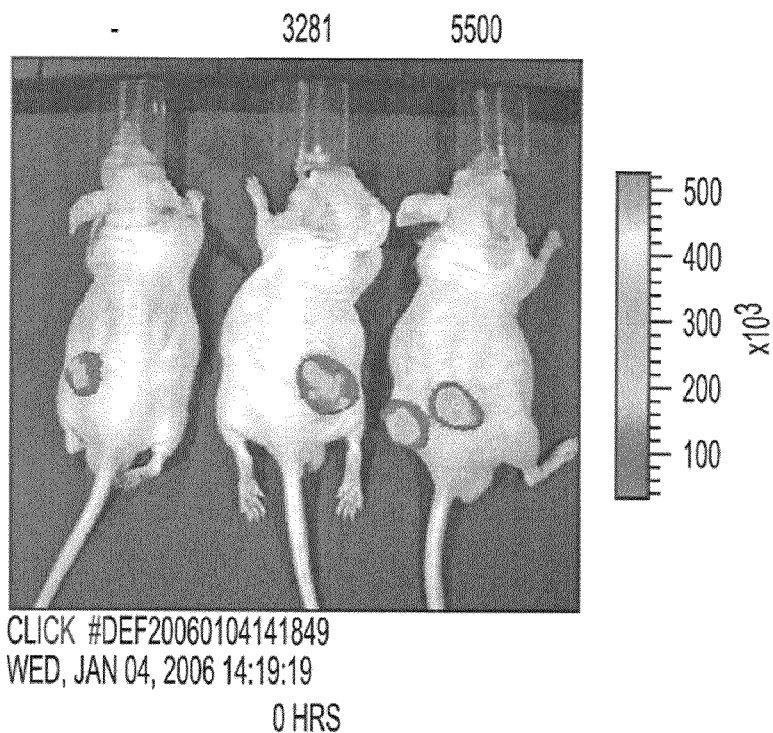
Figure 9B:
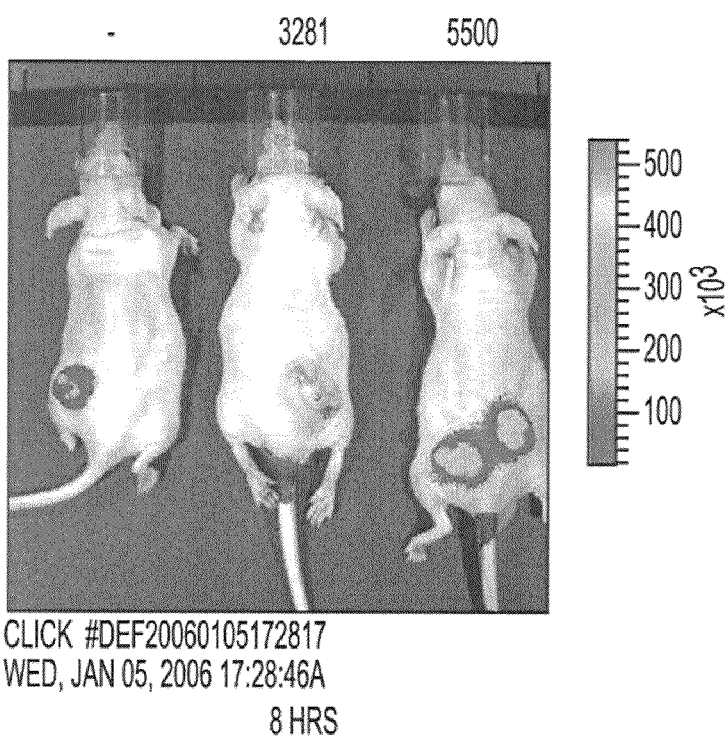
Figure 9C:
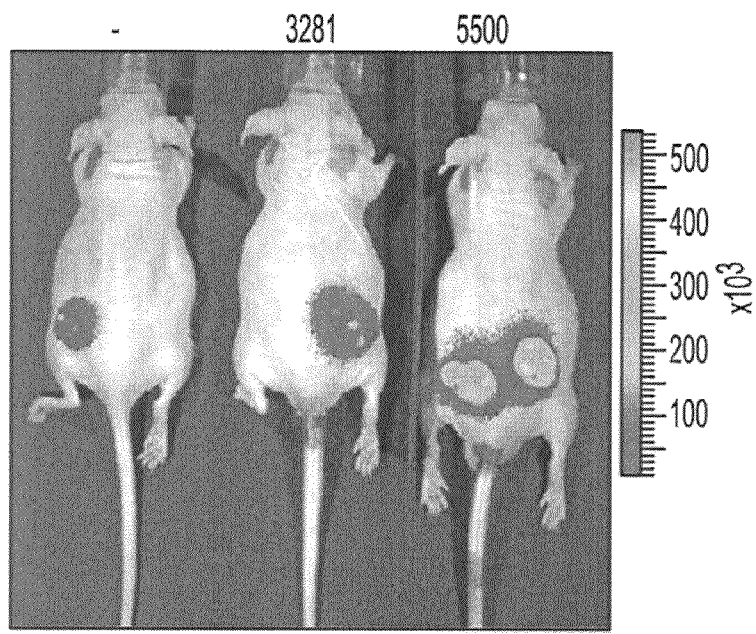
Figure 9D:
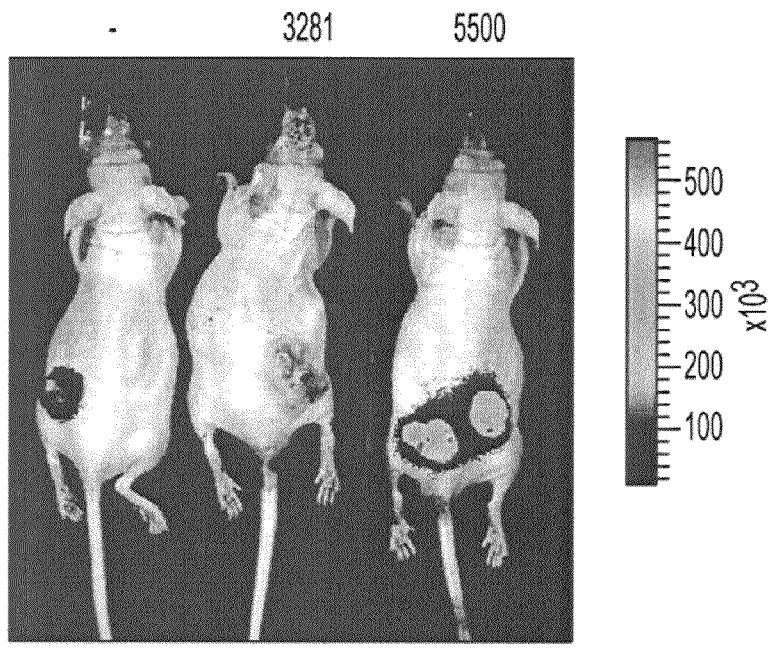

FIGS. 9A-D illustrate the effects of administration of two different potential irestatins to nude mice implanted with HT1080 cells stably expressing XBP-1s-luciferase. FIG. 9A shows bioluminescent activity prior to injection, FIG. 9B shows activity 8 hours after injection, FIG. 9C shows activity 24 hours after injection, and FIG. 9D shows activity 8 hours after a second injection of the potential irestatins.

Figure 10:
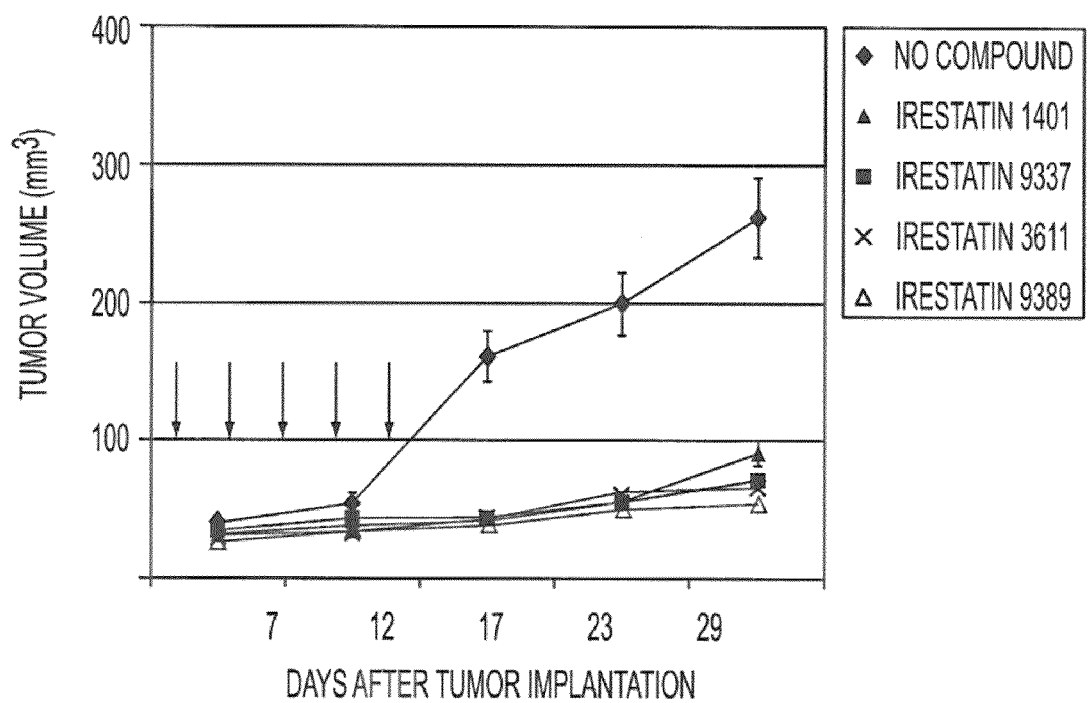

FIG. 10 shows the ability of the inventive irestatins to inhibit tumor growth in vivo in a mouse model. Dose: 60 mg/kg ip bolus injection every 48 hours. 5 total doses. 5-7 tumors per group. PANC1 pancreatic adenocarcinoma cell line.

FIG. 11 shows the inhibitory effects of Irestatin 9389 on the IRE1α/XBP-1 pathway.

FIG. 12 shows the inhibitory effects of Irestatin 9389 on the endonuclease function of IRE1α.

FIG. 13 shows that exposure to irestatin 9389 induces apoptosis and impairs cell survival under hypoxia and ER stress.

FIG. 14 shows the in vivo antitumor activity of irestatin 9389.

Figure 15:
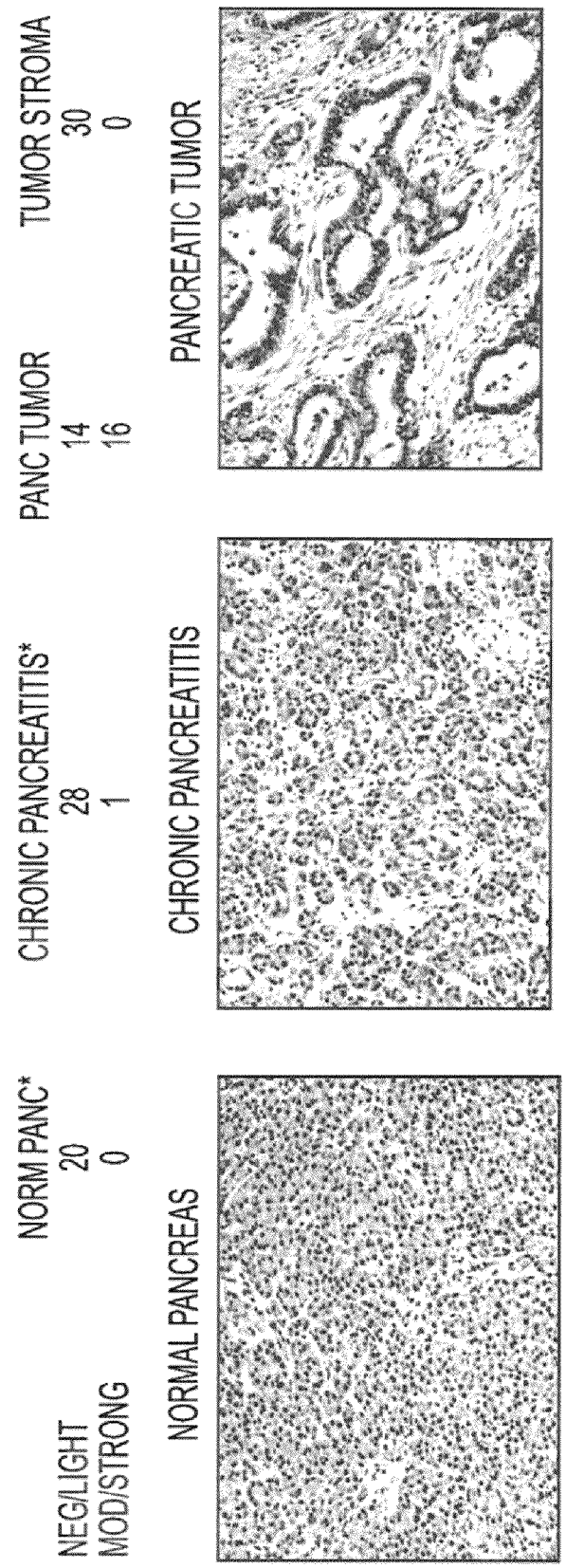

FIG. 15 shows expression of XBP-1s in human pancreas tissue specimens.

Figure 16:
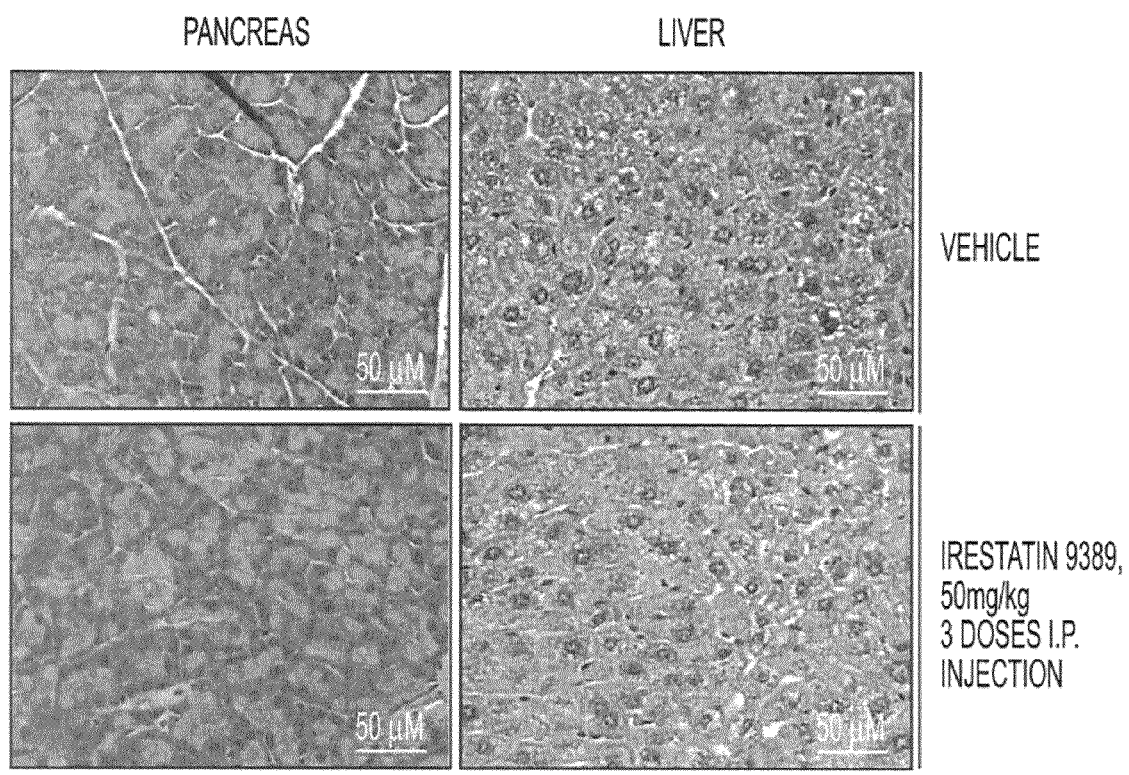

FIG. 16 shows histopathological analysis of mouse pancreas and liver tissues.

DETAILED DESCRIPTION OF THE INVENTION

Before further description of the invention, certain terms employed in the specification, examples and appended claims are, for convenience, collected here.

The term "alkoxy" refers to an alkyl group, in certain specific embodiments, a lower alkyl group, having an oxygen attached thereto. Representative alkoxy groups include methoxy, ethoxy, propoxy, tert-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, cycloalkyl, heterocyclyl, aryl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

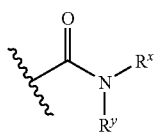

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

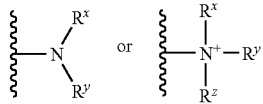

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

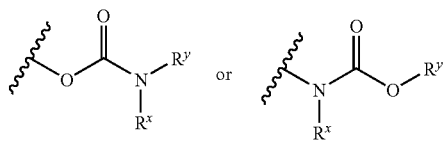

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group —$OCO_2$—$R^4$, wherein $R^4$ represents a hydrocarbyl group.

The term "carboxy", as used herein, refers to a group represented by the formula —$CO_2H$.

The term "ester", as used herein, refers to a group —C(O)O$R^x$ wherein $R^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

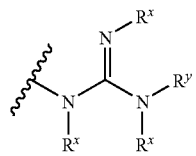

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

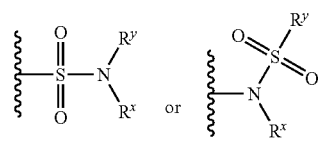

wherein R$^x$ and R$^y$ independently represent hydrogen or hydrocarbyl.

The term "sulfoxide" is art-recognized and refers to the group —S(O)—R$^x$, wherein R$^x$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^x$, wherein R$^x$ represents a hydrocarbyl.

The term "thioalkyl", as used herein, refers to an alkyl group substituted with a thiol group.

The term "thioester", as used herein, refers to a group —C(O)SR$^x$ or —SC(O)R$^x$ wherein R$^x$ represents a hydrocarbyl.

The term "thioether", as used herein, is equivalent to an ether, wherein the oxygen is replaced with a sulfur.

The term "urea" is art-recognized and may be represented by the general formula

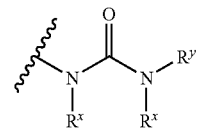

wherein R$^x$ and R$^y$ independently represent hydrogen or a hydrocarbyl.

As outlined above, the present invention provides compounds that are inhibitors of the unfolded protein response, in particular of IRE1 activity, together with compositions comprising such compounds and methods for their use in the treatment of various disorders. Without intending to be bound by theory, IRE1 is responsible for splicing XBP-1 into its active form and therefore reduction of IRE1 activity will in turn lead to a reduction in XBP-1 activity. Conversely, activation of IRE1 will lead to an increase in XBP-1 activity. IRE1 is activated by dimerization and autophosphorylation through its kinase domain. The endonuclease activity of IRE1 depends upon having an intact kinase domain, and to date, XBP-1 is the only described substrate for the endonuclease function of IRE1.

Inhibitors of the Unfolded Protein Response and/or IRE1

In one aspect, the present invention provides novel inhibitor compounds, including inhibitors of the unfolded protein response and/or IRE1 activity, referred to herein as irestatins. In certain embodiments, the compounds are represented by structural formula (I):

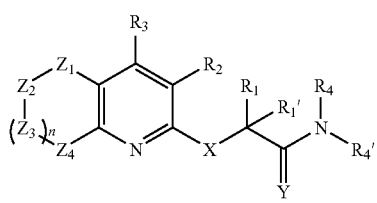

or a pharmaceutically acceptable derivative or prodrug thereof, wherein:

X is O, S, or N—$R_4''$;

Y is O or S;

$Z_1$, $Z_2$, $Z_3$, and $Z_4$ are independently $C(R_6)(R_6')$ or $NR_4''$, provided that only one of $Z_1$, $Z_2$, $Z_3$, and $Z_4$ at a time is N—$R_4''$;

n is 0-2;

$R_1$, $R_1'$, $R_6$, and $R_6'$ are independently hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and are optionally substituted with 1-3 J groups;

$R_2$ is alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

$R_3$ is alkyl, alkenyl, alkynyl, aralkyl, alkoxy, aryloxy, aralkoxy, cycloalkyl, cycloalkenyl, cycloalkoxy, haloalkyl, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

$R_1$, $R_1'$, and $R_2$ taken together may form

wherein $R_5$ is hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

$R_4$, $R_4'$, and $R_4''$ are independently hydrogen, alkyl, alkenyl, alkynyl, aryl, aralkyl, aralkenyl, cycloalkyl, cycloalkenyl, cycloalkoxy, heterocyclyl, heterocyclylalkyl, heteroaryl, heteroaralkyl, formate, formamide, acyl, phosphoryl, sulfonyl, or sulfonamido and are optionally substituted with 1-3 J groups, wherein $R_4$ and $R_4'$ taken together with the N atom to which they are attached complete a cyclic structure having from 4 to 8 atoms in the ring;

J is alkyl, alkenyl, alkynyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J' groups; and J' is alkyl, alkenyl, alkynyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

provided that when X is S and Y is O;

$R_1$ and $R_1'$ are hydrogen and $R_2$ is CN or $R_1$, $R_1'$, and $R_2$ together form

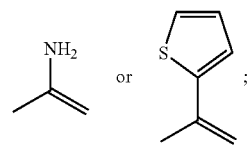

$Z_1$, $Z_3$, and $Z_4$ are $CH_2$, and $Z_2$ is $CH_2$, $NC(O)CH_3$, $CHCH_3$, $CHCH_2CH_3$, $CHCH(CH_3)_2$, $CHCH_2CH(CH_3)_2$, or CH-phenyl;

and $R_3$ is $CH_3$, $CF_3$, i-Bu, Br, C(O)OEt, or CH=CH-phenyl;

then $R_4$ and $R_4'$ are not both hydrogen or ethyl; $R_4$ and $R_4'$ taken together with the N atom to which they are attached do not form a tetrahydroisoquinoline or N-methylpiperazine; and when $R_4$ is hydrogen, $R_4'$ is not $C_{1-4}$ alkyl; $CH_2COOH$; unsubstituted cyclohexyl; unsubstituted naphthyl; unsubstituted adamantyl;

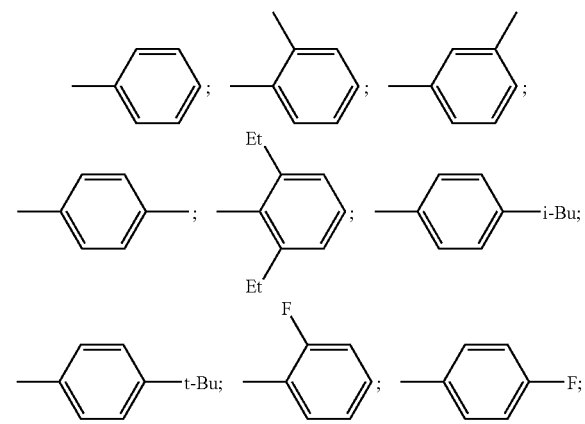

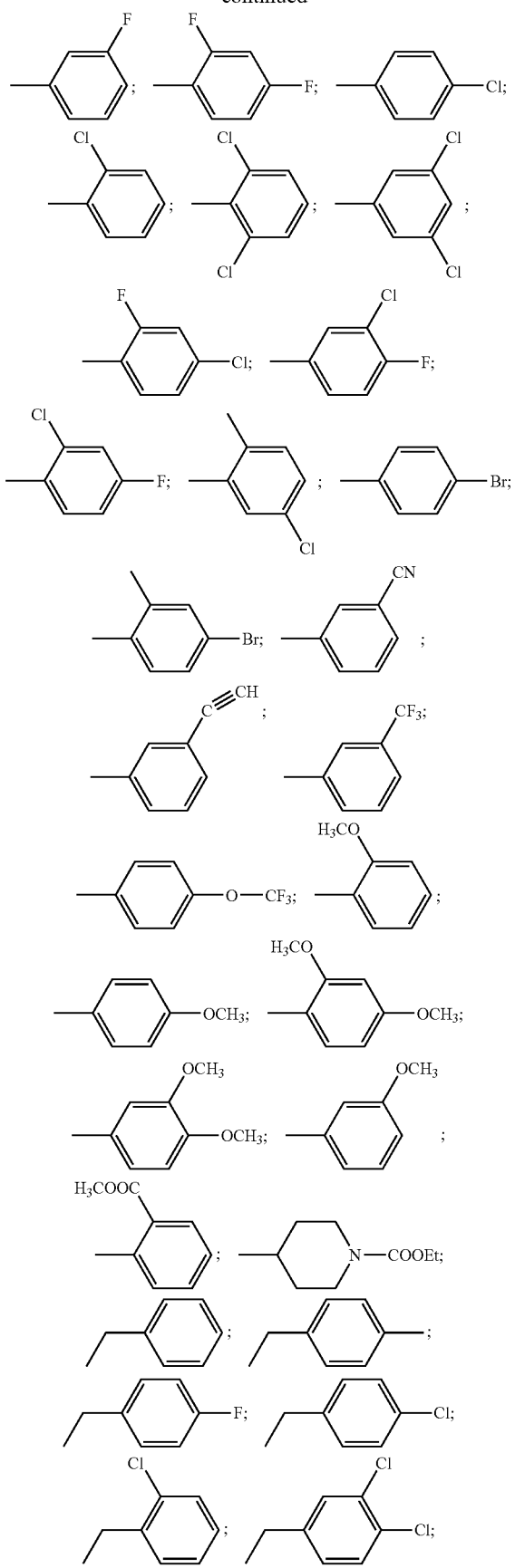
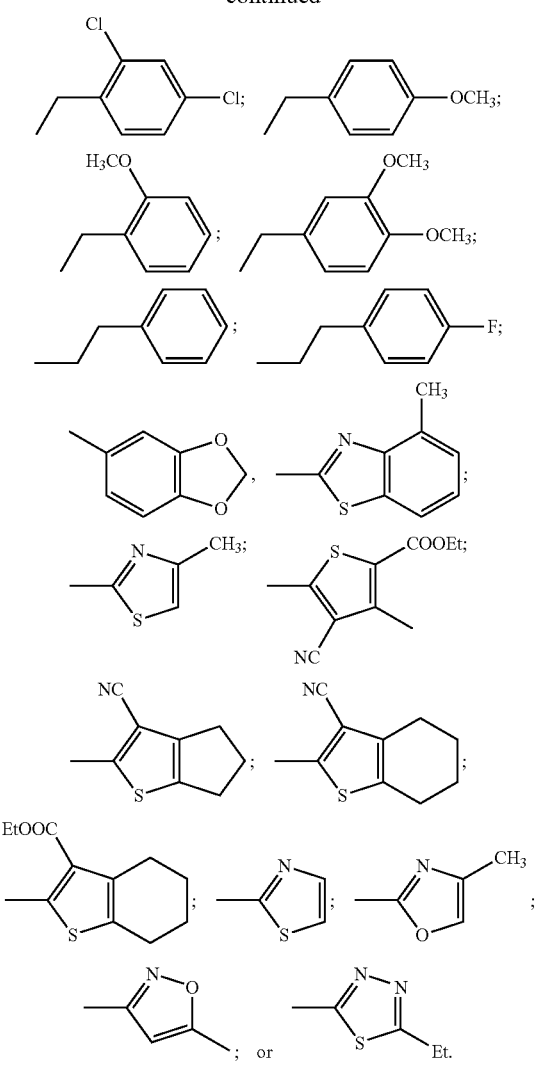

In some embodiments of the invention, $Z_1$, $Z_2$, $Z_3$, and $Z_4$ are $C(R_6)(R_6')$, and n is 0 or 1.

In some embodiments, $R_6$ and $R_6'$ are both hydrogen.

In some embodiments, X is S.

In some embodiments, Y is O.

In some embodiments, $R_3$ is alkyl or haloalkyl.

In other embodiments, $R_3$ is $CF_3$.

In some embodiments, $R_1$ and $R_1'$ are both hydrogen.

In some embodiments, $R_1$ and $R_1'$ are both hydrogen, and $R_2$ is CN.

In some embodiments, $R_1$, $R_1'$, and $R_2$ together form

and in more specific embodiments, $R_5$ is $NH_2$.

In some embodiments, $R_4$ is hydrogen, and $R_4'$ is an optionally substituted aryl, heteroaryl, aralkyl, or heteroaralkyl.

In specific embodiments, $R_4'$ is an optionally substituted

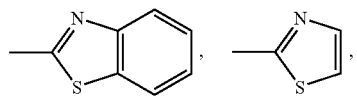

pyridinyl, phenyl, or benzyl.

In even more specific embodiments, $R_4'$ is substituted with one or two $CH_3$, $CH_2CH_3$, CN, $OCH_3$, or phenyl groups.

In still more specific embodiments, $R_4'$ is

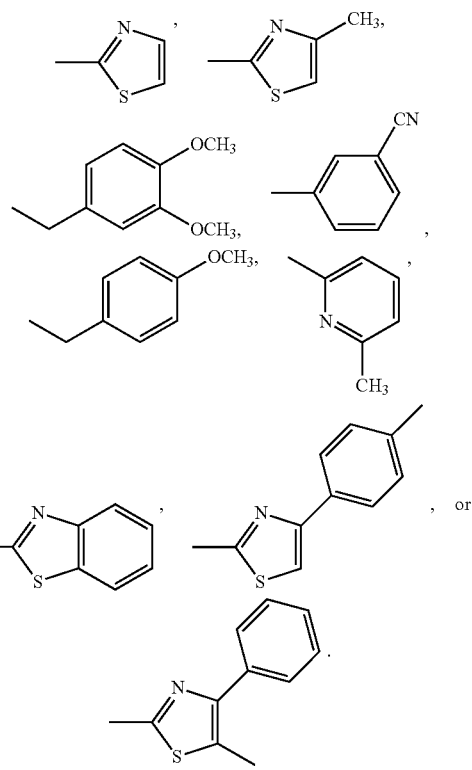

In even more specific embodiments, $R_4'$ is

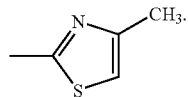

In some embodiments, $R_4$ and $R_4'$ are both alkyl.
In more specific embodiments, $R_4$ and $R_4'$ are both ethyl.
In some embodiments, $Z_2$ is $NR_4''$; and $R_4''$ is $C(O)CH_3$.
In some embodiments, $Z_1$, $Z_2$, $Z_3$, and $Z_4$ are $CR_6R_6'$, n is 0 or 1, X is S, Y is O, $R_1$ and $R_1'$ are hydrogen, $R_2$ is CN, and $R_3$ is $CF_3$.
In specific embodiments, $R_6$ and $R_6'$ are both hydrogen.
In some embodiments, $Z_1$, $Z_2$, $Z_3$, and $Z_4$ are $CR_6R_6'$, n is 0 or 1, X is S, Y is O, $R_1$, $R_1'$, and $R_2$ together form

$R_3$ is $CF_3$, and $R_5$ is $NH_2$.
In specific embodiments, $R_6$ and $R_6'$ are both hydrogen.
In some embodiments, $Z_1$, $Z_2$, $Z_3$, and $Z_4$ are $CR_6R_6'$, n is 0 or 1, X is S, Y is O, $R_3$ is $CF_3$, $R_4$ is hydrogen, and $R_4'$ is

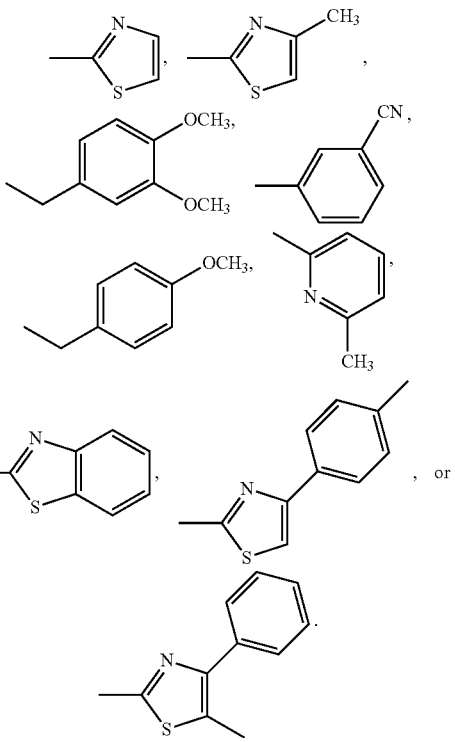

In specific embodiments, $R_6$ and $R_6'$ are both hydrogen.
In some embodiments, $R_1$, $R_1'$, $R_2$, $R_3$, $R_4$, $R_4'$, $R_4''$, $R_5$, J, and J' each independently contains 10 or fewer non-hydrogen atoms.

In specific embodiments, $R_1$, $R_1'$, $R_2$, $R_3$, $R_4$, $R_4'$, $R_4''$, $R_5$, J, and J' each independently contains 6 or fewer non-hydrogen atoms.

In certain embodiments, the compounds of the invention do not include the following compounds:

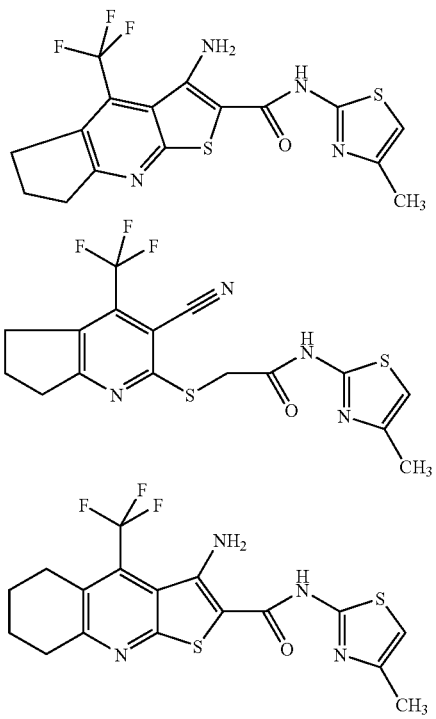

-continued

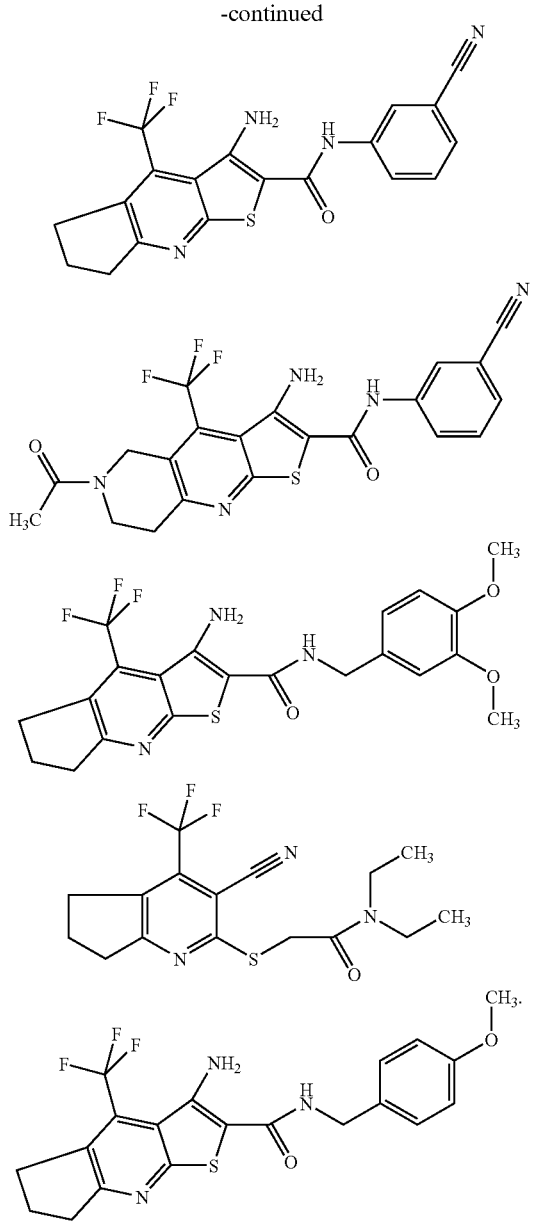

When a particular stereochemical or geometric isomer is specified in a structure, or when a particular isomeric purity is indicated, the particular form can be obtained by asymmetric synthesis, synthesis from optically pure precursors, or by resolution of racemates or other mixtures of stereochemical or geometric isomers. Resolution of racemates or other mixtures may also be accomplished, for example, by conventional methods such as crystallization in the presence of a resolving agent, or chromatography, using, for example a chiral HPLC column.

As used herein, the compounds of the invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention, which, upon administration to a recipient, is capable of providing or provides (directly or indirectly) a compound of the invention.

Accordingly, this invention also provides prodrugs of the compounds of the invention, which are derivatives that are designed to enhance biological properties such as oral absorption, clearance, metabolism, or compartmental distribution. Such derivations are well known in the art.

As the skilled practitioner realizes, the compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism, or alter rate of excretion.

Certain derivatives and prodrugs are those that increase the bioavailability of the compounds of the invention when such compounds are administered to an individual (e.g., by allowing an orally administered compound to be more readily absorbed into the blood), have more favorable clearance rates or metabolic profiles, or enhance delivery of the parent compound to a biological compartment (e.g., the brain or lymphatic system) relative to the parent species. Examples of prodrugs include derivatives in which a group that enhances aqueous solubility or active transport through the gut membrane is appended to the structure.

In some embodiments, the compounds of the invention are provided in the form of pharmaceutically acceptable salts. Compounds containing an amine may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

Compounds of the instant invention that are acidic in nature may accordingly react with any number of inorganic and organic bases to form pharmaceutically acceptable base salts. Specific bases include the mineral bases, such as NaOH and KOH, but one of skill in the art would appreciate that other bases may also be used. See Ando et al., *Remington: The Science and Practice of Pharmacy*, 20th ed. 700-720 (Alfonso R. Gennaro ed.), 2000.

The pharmaceutically acceptable addition salts of the compounds of the invention may also exist as various solvates, such as with water, methanol, ethanol, dimethylformamide, and the like. Mixtures of such solvates may also be prepared. The source of such solvate may be from the solvent of crystallization, inherent in the solvent of preparation or crystallization, or adventitious to such solvent.

Synthesis of the Inhibitors of the Unfolded Protein Response

The compounds of the invention may be synthesized using conventional synthetic chemical techniques. Advantageously, these compounds are synthesized from readily available starting materials. Compound 9389 (Table 1), and structurally-related compounds, may be synthesized using, for example, the following synthetic scheme:

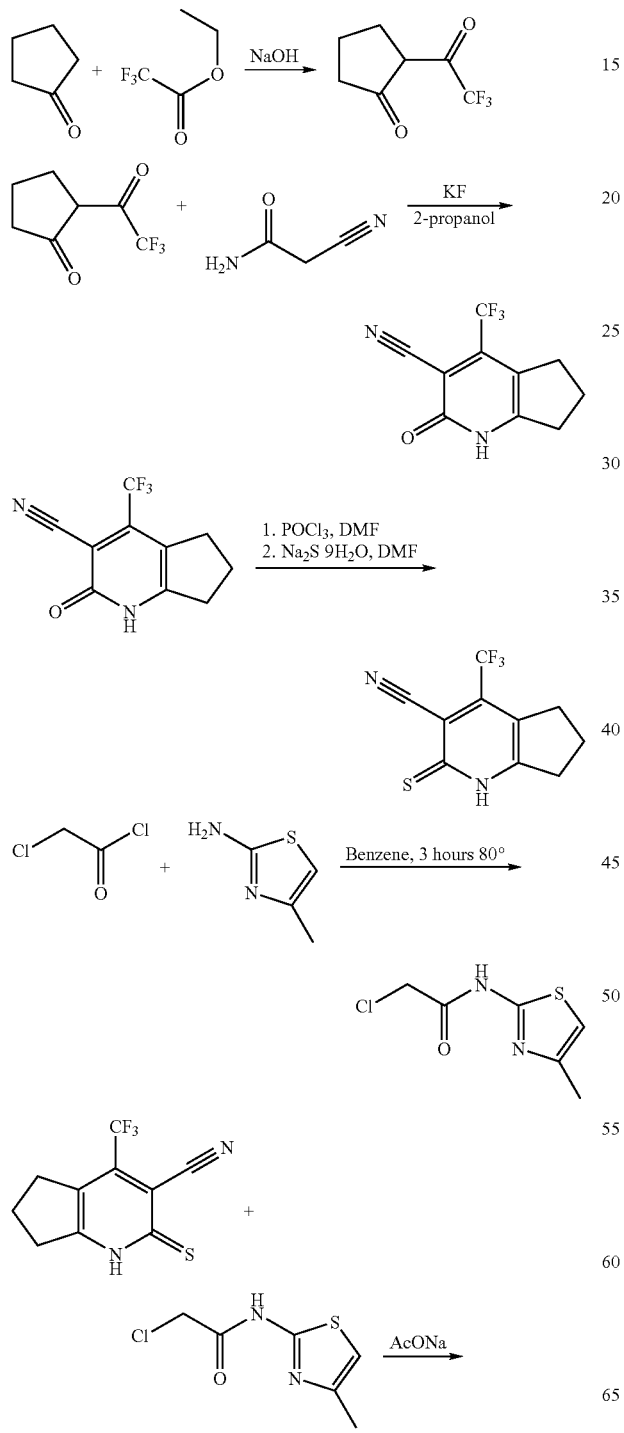

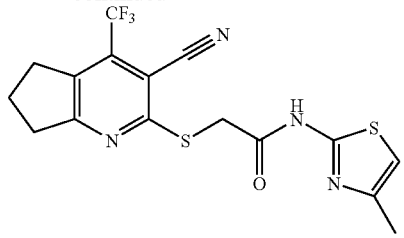

9389

See, e.g., *J. Am. Chem. Soc.* 75:4753 (1953); *Russian Chemical Bulletin* 50(4):669-672 (2001); *Khimiya Geterotsiklicheskikh Soedinenii* (9)1233-7 (1987); Awad et al., *Phosphorus, Sulfur and Silicon and the Related Elements* 57(3-4):293-301 (1991); Geronikaki et al., *Molecules* 8(6):472-9 (2003).

Variants of the above structure may be synthesized, for example, using the following commercially available amines:

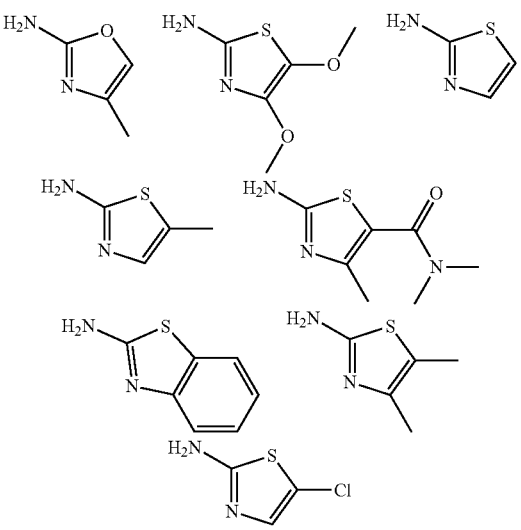

Similar approaches may be used to introduce the following exemplary groups at the $R_4'$ position of formula (I):

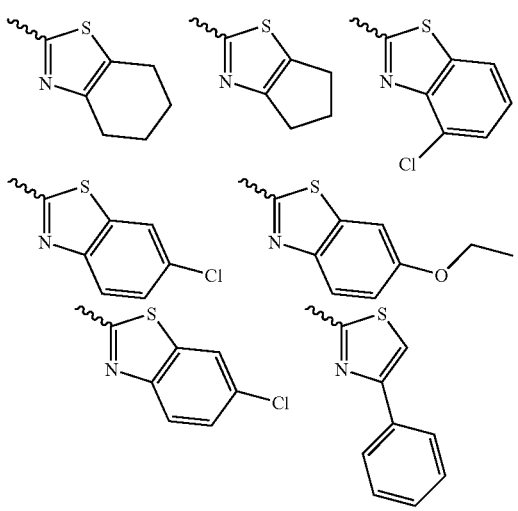

Further variation in the bicyclic ring of compound 9389 and structurally-related compounds is provided, for example, by substitution of

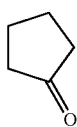

in the above reaction scheme with other suitable reagents. Variation at the position of —CF$_3$ in compound 9389 and structurally-related compounds may likewise be provided by appropriate substitution of starting materials, as would be understood by the skilled artisan.

Ring closure of compound 9389 and structurally-related compounds according to the following scheme provides compound 5500 and structurally-related compounds:

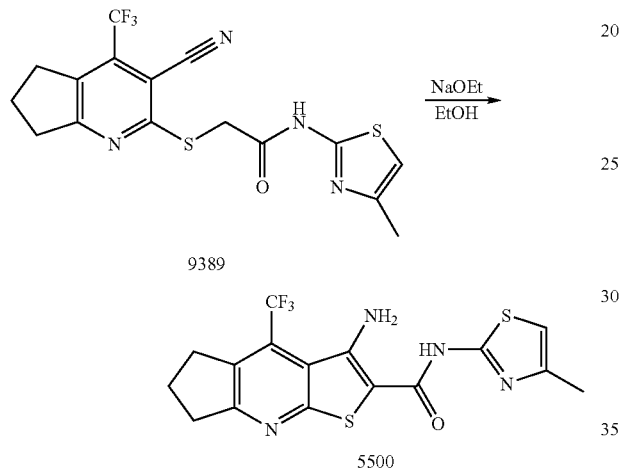

Further variation in these compounds may be provided, for example, by chemical modification of the extracyclic amino group of compound 5500.

As can be appreciated by the skilled artisan, the synthetic methods disclosed herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and methodologies useful in synthesizing the inhibitor compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995). The compounds may be synthesized using solution-phase or solid-phase techniques. See, for example, Merrifield, *J. Am. Chem. Soc.* 85:2149-2154 (1963).

Pharmaceutical Compositions

In another aspect, the compounds of the invention may be administered as a pharmaceutical compositions containing, for example, a compound of structural formula (I) and a pharmaceutically acceptable carrier, wherein formula (I) is:

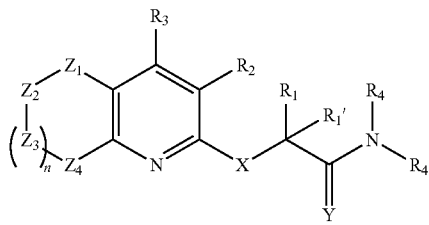

(I)

or a pharmaceutically acceptable derivative or prodrug thereof, wherein:

X is O, S, or N—R$_4$";

Y is O or S;

Z$_1$, Z$_2$, Z$_3$, and Z$_4$ are independently C(R$_6$)(R$_6$') or NR$_4$", provided that only one of Z$_1$, Z$_2$, Z$_3$, and Z$_4$ at a time is N—R$_4$";

n is 0-2;

R$_1$, R$_1$', R$_6$, and R$_6$' are independently hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and are optionally substituted with 1-3 J groups;

R$_2$ is alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

R$_3$ is alkyl, alkenyl, alkynyl, aralkyl, alkoxy, aryloxy, aralkoxy, cycloalkyl, cycloalkenyl, cycloalkoxy, haloalkyl, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

R$_1$, R$_1$', and R$_2$ taken together may form

wherein R$_5$ is hydrogen, alkyl, alkenyl, alkynyl, aryl, aralkyl, alkoxy, aryloxy, aralkoxy, cycloalkyl, cycloalkenyl, cycloalkoxy, heterocyclyl, heterocyclyloxy, heterocyclylalkyl, heteroaryl, heteroaralkyl, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J groups;

R$_4$, R$_4$', and R$_4$" are independently hydrogen, alkyl, alkenyl, alkynyl, aryl, aralkyl, aralkenyl, cycloalkyl, cycloalkenyl, cycloalkoxy, heterocyclyl, heterocyclylalkyl, heteroaryl, heteroaralkyl, formate, formamide, acyl, phosphoryl, sulfonyl, or sulfonamido and are optionally substituted with 1-3 J groups, wherein R$_4$ and R$_4$' taken together with the N atom to which they are attached complete a cyclic structure having from 4 to 8 atoms in the ring;

J is alkyl, alkenyl, alkynyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J' groups; and J' is alkyl, alkenyl, alkynyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

and a pharmaceutically acceptable carrier.

In specific embodiments, the substituents of formula (I) are defined as described above.

In more specific embodiments, the compositions of the invention comprise the following compounds:

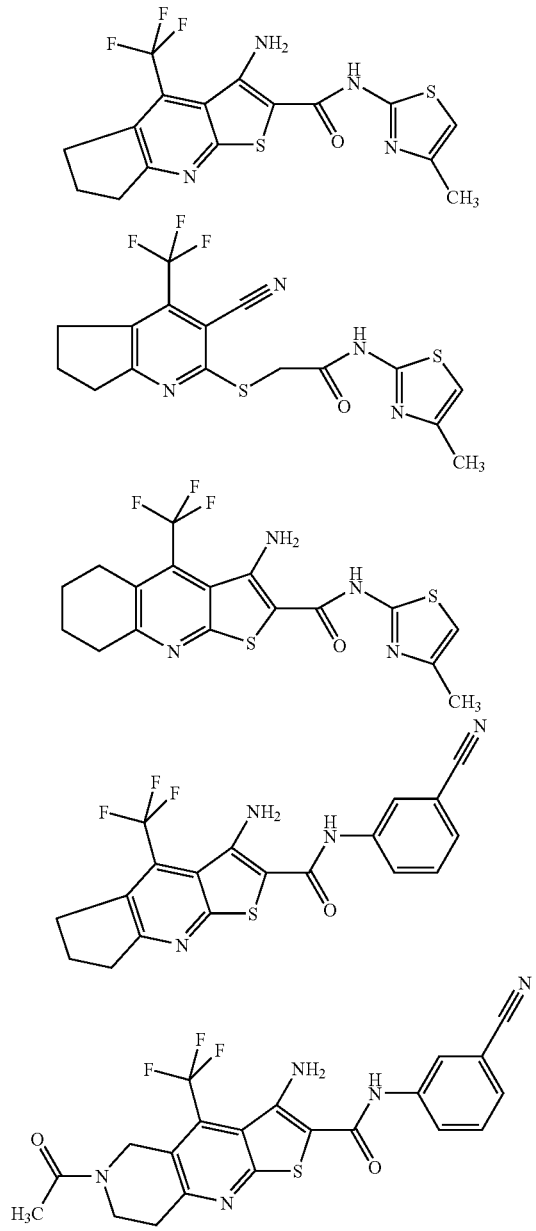

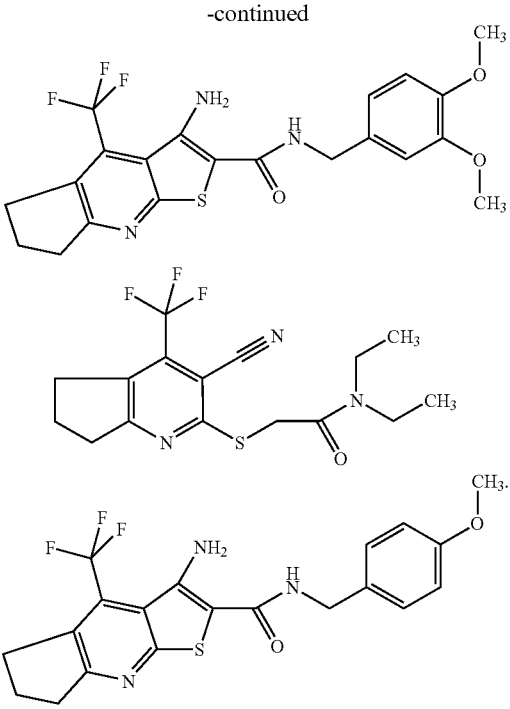

Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See *Remington: The Science and Practice of Pharmacy*, 20th ed. (Alfonso R. Gennaro ed.), 2000.

A pharmaceutical composition containing a compound of the instant invention may be administered to a host by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations of the present invention may conveniently be presented in unit dosage form and may be prepared by any methods well known in the art of pharmacy. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, in some embodiments from about 5 percent to about 70 percent, and in more specific embodiments from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions may be formulated for delivery via a catheter, stent, wire, or other intraluminal device. Delivery via such devices may be especially useful for delivery to the bladder, urethra, ureter, rectum, or intestine.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound of this invention, excipients such as lactose, talc, silicic acid, aluminum hydroxide, calcium silicates, and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers may also be used to increase the flux of the compound across the skin. The rate of such flux may be controlled by either providing a rate controlling membrane or dispersing the compound in a polymer matrix or gel.

Ophthalmic formulations, eye ointments, powders, solutions, and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

In certain embodiments, the present invention provides compositions comprising at least one compound provided in Table 1 below, or an analog, derivative, or functional equivalent thereof. As detailed below, the compounds shown in Table 1, and others, have been found to be inhibitors of IRE1 activity and to possess potent, hypoxia-specific, cytotoxicity. As further detailed below, the inventive compositions may also comprise, or may be used in combination with, one or more known cytotoxic, vascular targeting agents or chemotherapeutic agents including, but not limited to, Xeloda™ (capecitabine), Paclitaxel™, FUDR (fluorouridine) Fludara™ (fludarabine phosphate), Gemzar™ (gemcitabine), methotrexate, cisplatin, carboplatin, adriamycin, avastin, tarceva, taxol, tamoxifen, Femora, temezolamide, cyclophosphamide, Erbitux, and Sutent.

In certain embodiments, the inventive compositions comprise at least one compound having a structure shown in Table 1 below, together with analogs of such compounds. As described in detail below, the inventors have demonstrated that these and related compounds (referred to herein as irestatins) may be effectively employed to inhibit the activity of the unfolded protein response and/or IRE1. As described above, and as will be appreciated by those of skill in the art, the structures of Table 1, and analogs thereof, may be synthesized using techniques known in the art, for example using variations of the synthetic schemes described above.

TABLE 1

| Compound identification no. | Structure |
|---|---|
| 0953 | 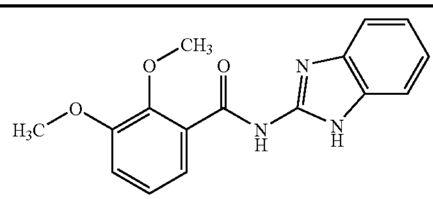 |
| 1401 | 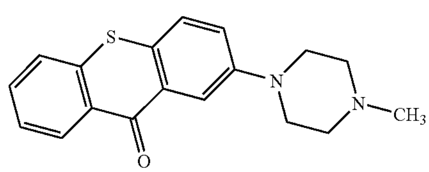 [SMILES: CN1CCN(c2ccc3sc4ccccc4c(=O)c3c2)CC1] |
| 6149 | 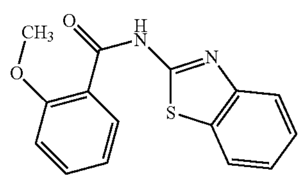 [SMILES: COc1ccccc1C(=O)Nc1nc2ccccc2s1] |
| 6159 | 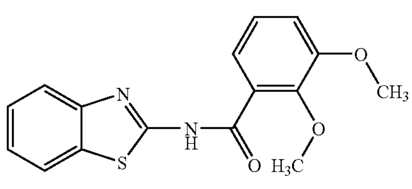 [SMILES: COc1cccc(C(=O)Nc2nc3ccccc3s2)c1OC] |
| 0222 | 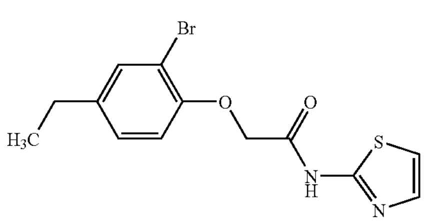 [SMILES: CCc1ccc(OCC(=O)Nc2nccs2)c(Br)c1] |

TABLE 1-continued

| Compound identification no. | Structure |
|---|---|
| 0824 | 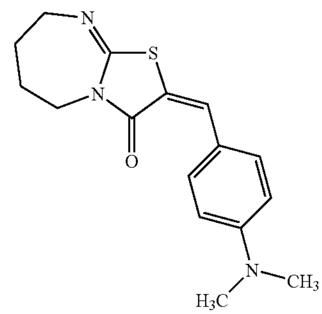 [SMILES: CN(C)c1ccc(/C=c2/sc3n(c2=O)CCCCN=3)cc1] |
| 3281 | 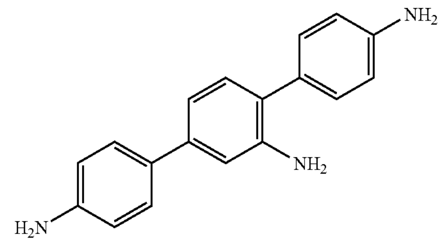 [SMILES: Nc1ccc(-c2ccc(-c3ccc(N)cc3)c(N)c2)cc1] |
| 5500 | 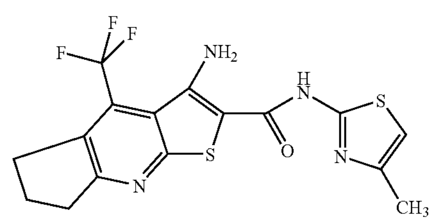 [SMILES: Cc1csc(NC(=O)c2sc3nc4c(c(C(F)(F)F)c3c2N)CCC4)n1] |
| 2614 | 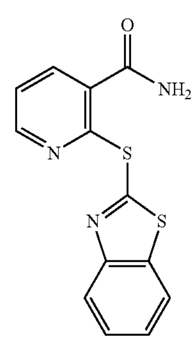 [SMILES: NC(=O)c1cccnc1Sc1nc2ccccc2s1] |
| 3611 | 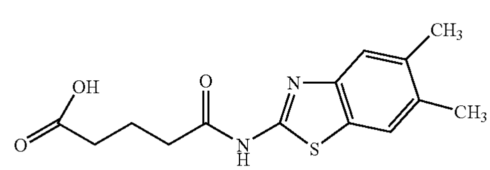 [SMILES: Cc1cc2nc(NC(=O)CCCC(=O)O)sc2cc1C] |

TABLE 1-continued

| Compound identification no. | Structure |
|---|---|
| 9389 | (structure) |
| 7546 | (structure) |
| 9255 | (structure) |
| 9337 | (structure) |
| 5116 | (structure) |
| 2880 | (structure) |
| 8710 | (structure) |
| 8731 | (structure) |

Packaged Pharmaceuticals

The pharmaceutical compositions of the invention may usefully be provided as packaged pharmaceuticals. The compositions are thus included in a container, package, or dispenser, either alone or as part of a kit with labels and instructions for administration. The packaged pharmaceuticals may in some cases further comprise additional therapeutics for use in combination with the provided composition. Such therapeutics may include, e.g., one or more chemotherapeutic agents.

Use of the Compounds and Compositions

The invention further provides methods for using the compounds and compositions described herein. In one aspect, the pharmaceutical compositions of the invention are used in methods for inhibiting the unfolded protein response and/or IRE1 in a mammalian host. Accordingly, the methods comprise administering to the mammalian host in need thereof a therapeutically-effective amount of a pharmaceutical composition as described above.

The host receiving treatment according to the disclosed methods is any mammal in need of such treatment. Such mammals include, e.g., humans, ovines, bovines, equines, porcines, canines, felines, non-human primate, mice, and rats. In certain specific embodiments, the host is a human. In certain other specific embodiments, the host is a non-human mammal. In some embodiments, the host is a farm animal. In other embodiments, the host is a pet.

In yet another aspect, the pharmaceutical compositions of the invention are used in methods for treating or preventing a disease associated with the unfolded protein response in a mammalian host. Such methods may comprise, for example, administering to the mammalian host in need thereof a therapeutically-effective amount of a pharmaceutical composition as described above.

By "therapeutically effective amount" is meant the concentration of a compound that is sufficient to elicit the desired therapeutic effect (e.g., treatment or prevention of a disorder associated with the unfolded protein response, etc.). It is generally understood that the effective amount of the compound will vary according to the weight, gender, age, and medical history of the host. Other factors that influence the effective amount may include, but are not limited to, the severity of the patient's condition, the disorder being treated, the stability of the compound, and, if desired, another type of therapeutic agent being administered with the compound of the invention. A larger total dose may be delivered by multiple administrations of the agent. Methods to determine efficacy and dosage are known to those skilled in the art. See, e.g., Roden, *Harrison's Principles of Internal Medicine*, Ch. 3, McGraw-Hill, 2004.

Actual dosage levels of the active ingredients in the pharmaceutical compositions of the invention may be varied so as to obtain an amount of the active ingredient that is effective to achieve the desired therapeutic response for a particular patient, composition, and mode of administration, without being toxic to the patient.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

If desired, the effective daily dose of the active compound may be administered as one, two, three, four, five, six, or more sub-doses administered separately at appropriate intervals throughout the day, optionally, in unit dosage forms. In certain embodiments of the present invention, the active compound may be administered two or three times daily. In specific embodiments, the active compound is administered once daily.

The preferred frequency of administration and effective dosage will vary from one individual to another and will depend upon the particular disease being treated and may be determined by one skilled in the art. However, it is contemplated that effective dosages of the inventive inhibitors may range from as low as about 1 mg per day to as high as about 1000 mg per day, including all intermediate dosages therebetween. More preferably, effective dosages may range from about 10 mg per day to about 100 mg per day, including all intermediate dosages therebetween. The inventive compositions may be administered in a single dosage, or in multiple, divided dosages.

In yet another aspect, the pharmaceutical compositions of the invention are used in methods for treating or preventing particular disorders. The methods comprise, for example, administering to the mammalian host in need thereof a therapeutically-effective amount of a pharmaceutical composition as described above. In this regard, the disorder may include, for example, cancer, autoimmune disorders, and diabetes.

Compositions that contain one or more of the disclosed inhibitors may be effectively employed in the treatment of cancers, particularly those cancers characterized by the presence of moderate to severe hypoxia. Non-limiting examples of such cancers include solid tumors and secretory cell malignancies, including multiple myeloma. Cancers that may be effectively treated employing the inventive compositions include, for example, cervix, brain, pancreas, breast, head and neck, and prostate cancers, and soft tissue sarcomas. Other disorders that may be effectively treated employing the inventive compositions include, but are not limited to, B cell autoimmune disorders (such as rheumatoid arthritis) and diabetes. In particular embodiments, the cancer is selected from the group consisting of multiple myeloma, cervical cancer, brain cancer, pancreatic cancer, head and neck cancers, prostate cancer, breast cancer, soft tissue sarcomas, primary and metastatic liver cancer, primary and metastatic lung cancer, esophageal cancer, colorectal cancer, lymphoma, and leukemia.

In other particular embodiments, the cancer is a solid tumor, such as, for example, a sarcoma, a carcinoma, or a lymphoma.

In some embodiments, the disorder is an autoimmune disorder selected, for example, from the group consisting of diabetes, lupus, rheumatoid arthritis, psoriasis, multiple sclerosis, and inflammatory bowel disease.

In some embodiments, the disorder is an inflammatory bowel disease selected, for example, from the group consisting of ulcerative colitis and Crohn's disease.

In some embodiments, the disorder is rheumatoid arthritis.

The present invention also provides methods for inhibiting IRE1 activity and/or XBP-1 expression in a cell, together with methods for modulating (for example inhibiting) cell survival, growth and/or proliferation under hypoxic conditions. For example, such methods may be employed to inhibit the growth, survival and/or proliferation of tumor cells, such as cells in solid tumors. Such methods, which comprise contacting the cell with one or more of the compounds disclosed herein, may be carried out in vitro, in vivo or ex vivo.

In one aspect, the invention provides a composition comprising a small molecule compound that is capable of inhibiting IRE1 activity.

In another aspect, the invention provides a composition comprising at least one compound selected from the group consisting of:

(a) compounds having a structure provided in Table 1;
(b) compounds that are salts of the structures provided in Table 1;
(c) compounds that are analogs or a compound of (a) or (b).

In some embodiments, the composition further comprises a physiologically acceptable carrier.

In some embodiments, the composition is formulated for administration by injection.

In some embodiments, the composition further comprises a known chemotherapeutic agent.

In another aspect, the invention provides a method for inhibiting the activity of IRE1 in a cell, comprising contacting the cell with any one of the above compositions.

In another aspect, the invention provides a method for inhibiting the growth and/or proliferation of a tumor cell comprising contacting the cell with any one of the above compositions.

In still another aspect, the invention provides a method for the treatment of a disorder in a patient, comprising administering to the patient any one of the above compositions.

In some of the method embodiments, the disorder is characterized by unwanted cell growth under conditions of hypoxia or ER stress.

In some of the method embodiments, the disorder is selected from the group consisting of cancer; autoimmune disorders; and diabetes.

In some of the method embodiments, the disorder is a cancer selected from the group consisting of multiple myeloma; cervical cancer; brain cancer; pancreatic cancer; head and neck cancers; prostate cancer; breast cancer; and soft tissue sarcomas.

In some of the method embodiments, the disorder is rheumatoid arthritis. In some of the method embodiments, the composition is administered in combination with a known therapeutic agent.

The inventive compounds also encompass analogs of the structures provided in Table 1 and other structures. In certain embodiments, such analogs comprise structural modifications that increase potency and stability, and/or reduce unwanted side effects in mammals. Such analogs will generally possess substantially the same inhibitory properties and/or substantially the same therapeutic activity as the corresponding structure shown in Table 1 and other structures. Preferably such analogs possess an ability to inhibit the unfolded protein response and/or IRE1 activity at a level that is at least 90%, more preferably 95% and preferably 100% of the level of the corresponding structure of Table 1. In certain embodiments, such analogs demonstrate at least 95% inhibition of IRE1 reporter activation as determined in the assay described below.

The inventive compositions comprising inhibitors of the unfolded protein response and/or IRE1 activity may be employed to inhibit abnormal cell proliferation in a patient. For example, the instant compositions may be used to effectively treat, or prevent, disorders such as, but not limited to, cancers, including: solid tumors, such as cervix, brain, pancreas, head and neck, breast, and prostate cancers; soft tissue sarcomas; secretory cell malignancies, including multiple myeloma; B cell autoimmune disorders, such as rheumatoid arthritis; and diabetes. Such methods involve administering an effective amount of one or more of the inventive compositions to a patient in need thereof.

As used herein, a "patient" refers to any warm-blooded animal, including, but not limited to, a human. Such a patient may be afflicted with disease or may be free of detectable disease. In other words, the inventive methods may be employed for the prevention or treatment of disease. The inventive methods may be employed in conjunction with other known therapies, such as those currently employed for the treatment of cancer. For example, the inventive compositions may be administered before, during or after, radiotherapy, photodynamic therapy, surgery and/or treatment with known chemotherapeutic agents such as, but not limited to, those discussed above.

In general, the inventive compositions may be administered by injection (e.g., intradermal, intramuscular, intravenous, intratumoral or subcutaneous), intranasally (e.g., by aspiration), orally, transdermally or epicutaneously (applied topically onto skin). In one embodiment, the compositions of the present invention are injected into a tumor.

As described above, for use in therapeutic methods, the inventive compositions may additionally contain a physiologically acceptable carrier, such as a buffer, solvent, diluent or aqueous medium. While any suitable carrier known to those of ordinary skill in the art may be employed in the compositions of this invention, the type of carrier will vary depending on the mode of administration. For parenteral administration, such as subcutaneous, intravenous, intravascular or intraperitoneal injection, the carrier preferably comprises water, saline, alcohol, a fat, a wax or a buffer. For oral administration, the inventive compositions may be formulated, for example in a tablet, time-release capsule or other solid form, and any of the above carriers or a solid carrier, such as mannitol, lactose, starch, magnesium stearate, sodium saccharine, talcum, cellulose, glucose, sucrose and magnesium carbonate, may be employed. Other components, such as buffers, stabilizers, antibacterial and antifungal agents, isotonic and absorption delaying agents, and the like, may be included in the inventive compositions. The inventive compositions may be provided in single dose or multi-dose containers.

Such compositions may be prepared using techniques well known to those of skill in the art. In certain embodiments, the inventive compositions are prepared as sterile injectables, either as liquid solutions or suspensions; solid forms suitable for use in preparing solutions or suspensions upon the addition of a liquid prior to injection; or as emulsions.

The compounds of the present invention may also be formulated into a composition in a neutral or salt form. Pharmaceutically acceptable salts include the acid addition salts (formed, for example with any free amino groups present), which are formed with inorganic acids such as, hydrochloric or phosphoric acids, or such organic acids as acetic, oxalic, tartaric, or mandelic acids and the like. Salts formed with any free carboxyl groups can also be derived from inorganic bases, such as sodium, potassium, ammonium, calcium or ferric hydroxides, and such organic bases as isopropylamine, trimethylamine, histidine, procaine and the like.

As described above, the methods of the invention may in some embodiments be used for treating or preventing cancer. Such methods may, in certain embodiments, further comprise administration of a chemotherapeutic agent. Chemotherapeutic agents that may be coadministered with pharmaceutical compositions of the instant invention include: alemtuzumab, aminoglutethimide, amsacrine, anastrozole, asparaginase, bcg, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, streptozocin, sunitinib, suramin, tamoxifen, temozolomide, teniposide, testosterone, thalidomide, thioguanine, thiotepa, titanocene dichloride, topotecan, tositumomab, trastuzumab, tretinoin, vatalanib, vinblastine, vincristine, vindesine, and vinorelbine.

Other useful chemotherapeutic agents for combination with the compounds of the present invention include MDX-010; MAb, AME; ABX-EGF; EMD 72 000; apolizumab; labetuzumab; ior-t1; MDX-220; MRA; H-11 scFv; Oregovomab; huJ591 MAb, BZL; visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; Prostate cancer antibody; H22xKi-4; ABX-MAI; Imuteran; and Monopharm-C.

These chemotherapeutic agents may be categorized by their mechanism of action into, for example, the following groups: anti-metabolites/anti-cancer agents, such as pyrimidine analogs (e.g., 5-fluorouracil, floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (e.g., actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (e.g., L-asparaginase, which systemically metabolizes L-asparagine and deprives cells which do not have the capacity to synthesize their own asparagine); antiplatelet agents; antiproliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (e.g., trastuzumab and others listed above); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (e.g., cortisone, dexamethasone, hydrocortisone, methylpednisolone, prednisone, and prenisolone); growth factor signal transduction kinase inhibitors; mitochondrial dysfunction inducers and caspase activators; chromatin disruptors.

The pharmaceutical compositions of the instant invention may be coadministered with chemotherapeutic agents either singly or in combination. Many combinatorial therapies have been developed, including but not limited to those listed in Table 2.

TABLE 2

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |
| CEV | Cyclophosphamide, Etoposide, Vincristine |

TABLE 2-continued

Exemplary combinatorial therapies for the treatment of cancer.

| Name | Therapeutic agents |
|---|---|
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP (Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |

TABLE 2-continued

Exemplary combinatorial therapies for the treatment of cancer.

| Name | Therapeutic agents |
|---|---|
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |

TABLE 2-continued

Exemplary combinatorial therapies for the treatment of cancer.

| Name | Therapeutic agents |
|---|---|
| "8 in 1" | Methylprednisolone, Vincristine, Lomustine, Procarbazine, Hydroxyurea, Cisplatin, Cytarabine, Dacarbazine |

In addition to conventional chemotherapeutics, the inhibitors described herein may also be used with antisense RNA, RNAi, or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Combination therapies comprising the inhibitors of the instant invention and a conventional chemotherapeutic agent may be advantageous over combination therapies known in the art because the combination allows the conventional chemotherapeutic agent to exert greater effect at lower dosage. In a specific embodiment, the effective dose ($ED_{50}$) for a chemotherapeutic agent, or combination of conventional chemotherapeutic agents, when used in combination with an epoxide inhibitor of the instant invention is at least 2 fold less than the $ED_{50}$ for the chemotherapeutic agent alone, and even more preferably at 5-fold, 10-fold, or even 25-fold less. Conversely, the therapeutic index (TI) for such chemotherapeutic agent or combination of such chemotherapeutic agent when used in combination with an epoxide inhibitor of the instant invention can be at least 2-fold greater than the TI for conventional chemotherapeutic regimen alone, and even more preferably at 5-fold, 10-fold, or even 25-fold greater.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

Examples

Example 1

Involvement of XBP-1 in Hypoxia and Tumor Growth

We have demonstrated that UPR related genes represent a major class of genes that are transcriptionally induced under hypoxia, that XBP-1 is activated during hypoxia in a HIF-1 independent manner, and that cell survival and apoptosis under hypoxia was mediated by XBP-1 (Romero L., et al. Cancer Res. 64:5943-5947, 2004). We have demonstrated that XBP-1 is essential for tumor growth. We implanted spontaneously transformed XBP-1 wild-type and knockout mouse embryonic fibroblasts (MEFs) as tumor xenografts into SCID mice and found that XBP-1 knockout MEFs were completely unable to grow as tumors. Furthermore, tumor growth was dependent upon the spliced form of XBP-1. We transfected spliced XBP-1 (XBP1s) into XBP-1 knockout MEFs and were able to restore the growth rate of these tumors back to that of the wild-type cells. We also transfected a mutant form of unspliced XBP-1 (XBP1u) in which the splice site was deleted. Transfection of this construct resulted in expression of an "unspliceable" form of XBP-1. Reintroduction of XBP1u into an XBP-1 null background was not able to restore tumor growth. These studies indicate that the spliced (activated) form of XBP-1 is a critical component of tumor growth. We obtained similar results using HT1080 cells overexpressing mutants of IRE1 in which either the kinase domain was deleted (IRE1ΔC) or both the kinase and endonuclease domain were deleted (IRE1ΔEn). Both of these deletion mutants were found to be defective in XBP-1 splicing and transactivation of a UPRE reporter.

Furthermore, we observed that tumor growth was impaired in tumor cells expressing IRE1 deletion mutants or an XBP-1 dominant negative (overexpression of mutant XBP-1 in which the transactivation domain was deleted). Conversely, hypoxia survival was increased and tumor growth was accelerated when the spliced form of XBP-1 was overexpressed. Taken together, these data strongly indicate that XBP-1 is an important regulator of tumor growth.

To further investigate the role of XBP-1 on tumor growth, we have developed an HT1080 cell line in which XBP-1 expression was regulated using a tetracycline inducible XBP-1 shRNA expression vector. In these cells, XBP-1 expression was inhibited in the presence of doxycycline, allowing us to determine the effect of inhibiting XBP-1 on an established tumor. In these experiments, doxycycline was added into the drinking water of tumor bearing mice when the tumors reached a size of 50-100 $mm^3$. In the presence of doxycycline, there was a significant delay in the growth of these tumors as compared to the controls. We observed even greater tumor growth delay with constitutive inhibition of XBP-1 by shRNA. We also obtained similar results when XBP-1 was inhibited in a dominant negative manner in both an inducible and constitutively expressed manner. From these experiments, we concluded that XBP-1 plays a critical role in tumor growth and inhibition of XBP-1 is a may therefore be an effective therapeutic strategy.

To validate the clinical significance of XBP-1 as a potential therapeutic target in pancreatic tumors, we performed immunohistochemical analysis on 30 pancreatic tumor specimens taken from consecutive surgical specimens, 30 surrounding stroma samples, 29 chronic pancreatitis samples, and twenty normal pancreas samples. We have previously reported on the oxygenation status of a subset of these pancreatic tumors and found that they were extremely hypoxic while the normal adjacent pancreas was well-oxygenated (Koong A., et al. Int. J. Radiat. Oncol. Biol. Phys. 48:919-922, 2000). Because they are so profoundly hypoxic, pancreatic tumors are ideal tumors for the development of hypoxia targeted therapies. For these studies, we generated an affinity purified peptide antibody that was specific for the spliced form of human XBP-1. The strongest XBP1s expression was observed in the pancreatic tumor with minimal expression in the surrounding stroma or normal pancreas.

Collectively, these data demonstrate that the spliced form of XBP-1 (XBP1s) is essential for tumor growth, important for survival during hypoxia, and overexpressed in human pancreatic tumors. These observations strongly indicate that inhibition of XBP-1 is a promising therapeutic strategy.

Example 2

Identification of Inhibitors of XBP-1 Splicing

A high throughput screen for small molecule inhibitors of IRE1 activity was developed as detailed below. The sequence for XBP-1 is described in, for example, Liou, H-C. et al. *Science* 247:1581-1584, 1990; and Yoshimura, T. et al. *EMBO J.* 9:2537-2542, 1990. The amino acid sequence for unspliced XBP-1 protein is provided in SEQ ID NO: 1, with corresponding cDNA sequence being provided in SEQ ID NO: 3. The amino acid sequence for the spliced form is provided in SEQ ID NO: 2.

Figure 1:
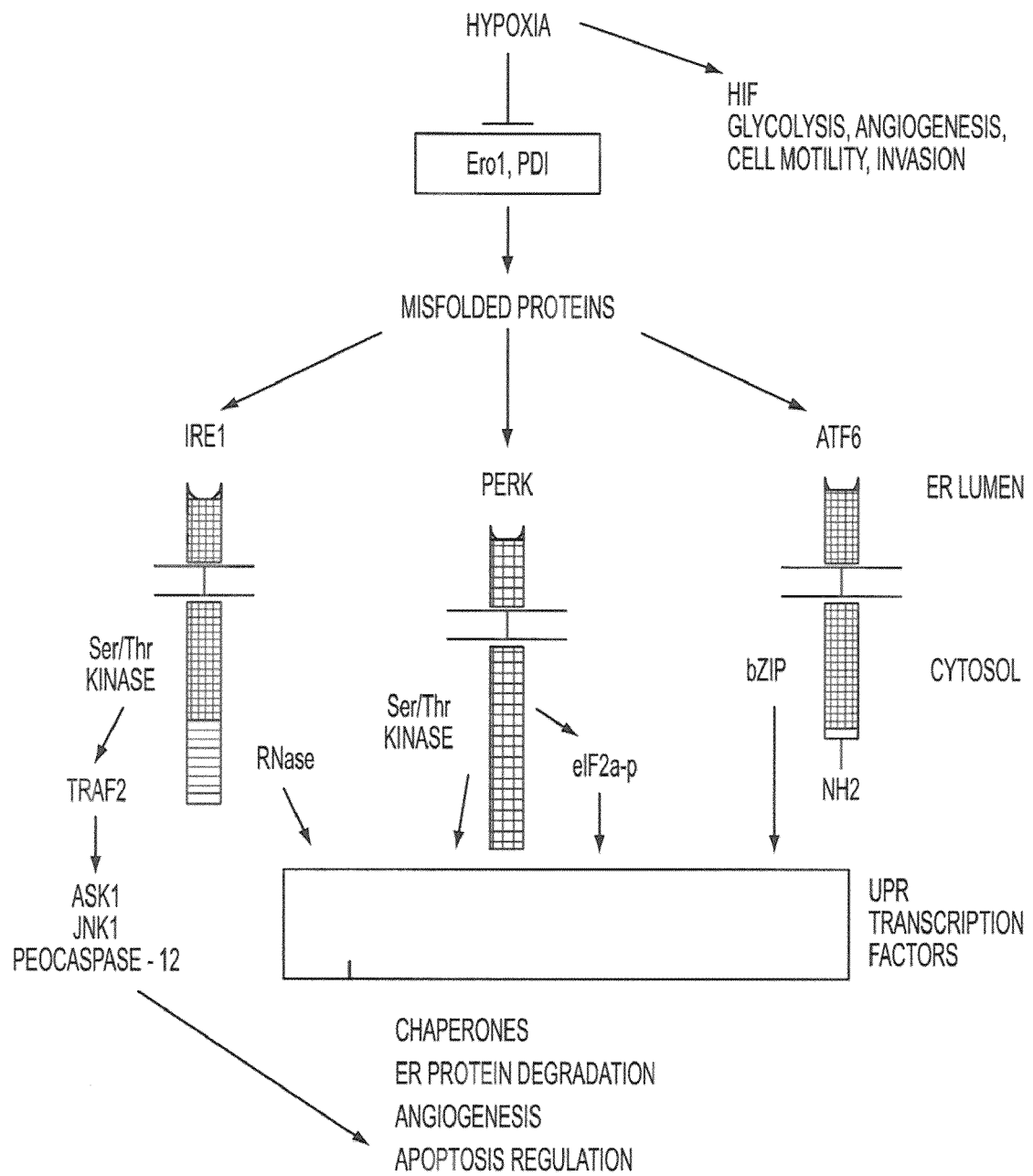
Figure 2A:
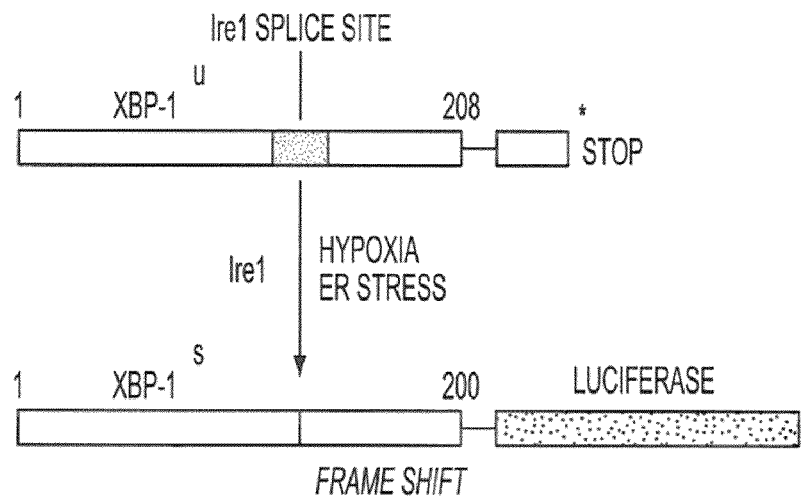
Figure 2B:
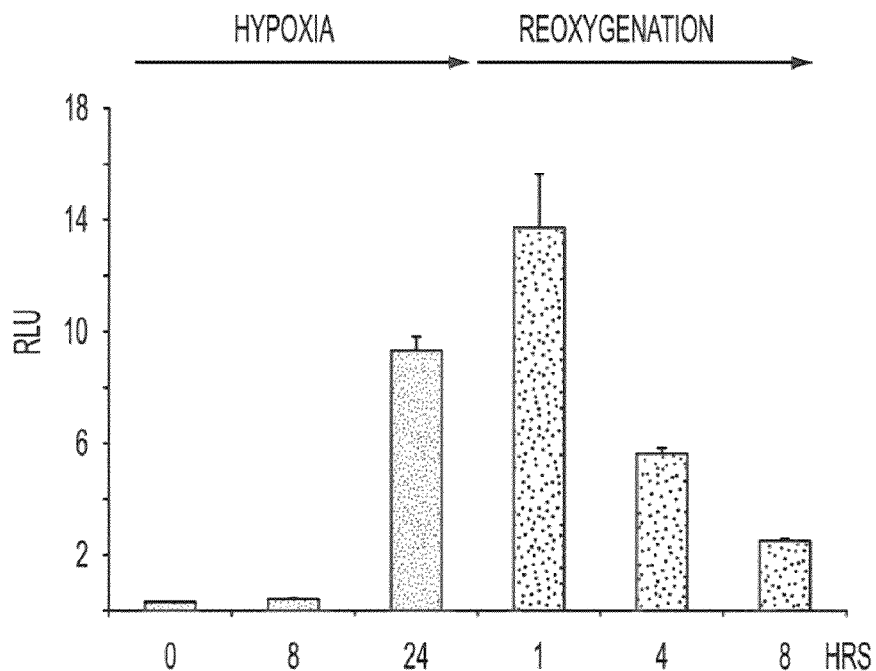

As shown in FIG. 2A, we developed a reporter construct in which luciferase was fused downstream and in frame with the unspliced form of XBP-1, containing the IRE-1 splice site. In the unspliced form, no luciferase is translated because of an endogenous stop codon. However, during hypoxia and ER stress, a 26 nt sequence is spliced out by IRE1 resulting in a frame-shift and read-through of the stop codon (Iwawaki et al., *Nat. Med.* 10:98-102, 2004). This results in production of an XBP1-luciferase fusion protein in which luciferase activity is detected only when XBP-1 is spliced by IRE1. This construct was stably transfected into HT1080 cells (human fibrosarcoma cell line). As shown in FIG. 2B, luciferase activity, detected after 24 hours of exposure to hypoxia, rapidly decreases when the HT1080 cells are allowed to reoxygenate, demonstrating that XBP-1 splicing is tightly controlled and largely restricted to hypoxic/ER stress conditions.

These tumor cells were used to screen a 66,000 chemically diverse small molecule library for inhibitors of XBP-1 splicing (Stanford High Throughput Facility compound library, which contains compounds from: SPECS & BioSPECS (Wakefield R.I.), Chembridge (San Diego, Calif.), and ChemRx libraries (Discovery Partners International, San Diego, Calif.)). In this screen, we used two drugs, tunicamycin ("Tm") (which blocks protein glycosylation) and thapsigargin ("Tg") (an inhibitor of ER Ca-ATPase) that cause ER stress to activate the IRE1 reporter.

Specifically, HT1080 fibrosarcoma cells stably transfected with the unspliced XBP-1-luciferase reporter construct (3000/well) were plated onto a solid white 384 well microplate with a multidrop dispenser (40 µL per well). The plates were then placed into an automated incubator. After 24 hours of growth, a mixture of tunicamycin (1 µg/ml) and thapsigargin (100 nM) inducers were added, and candidate compounds were then added to the plates. After 24 hours, luciferase reagent (10 µl) was added to each well and the plates were read in a Molecular Devices Analyst GT (0.2 second read per well). Compounds that blocked IRE1 activation showed reduced levels of luciferase activity compared to control wells.

Compounds were selected for further investigation on the basis of their ability to block IRE1 reporter activation. In order to be selected, a compound must have demonstrated >95% inhibition of the reporter. Using this selection criteria, we selected the top 400 compounds for further testing. In this group, we performed a secondary screen comparing the ability of these compounds to inhibit IRE1-regulated luciferase activity without having an effect on CMV-regulated luciferase activity. From this analysis, we selected 58 compounds and repeated the IRE1 reporter screen on each compound individually.

Figure 3:
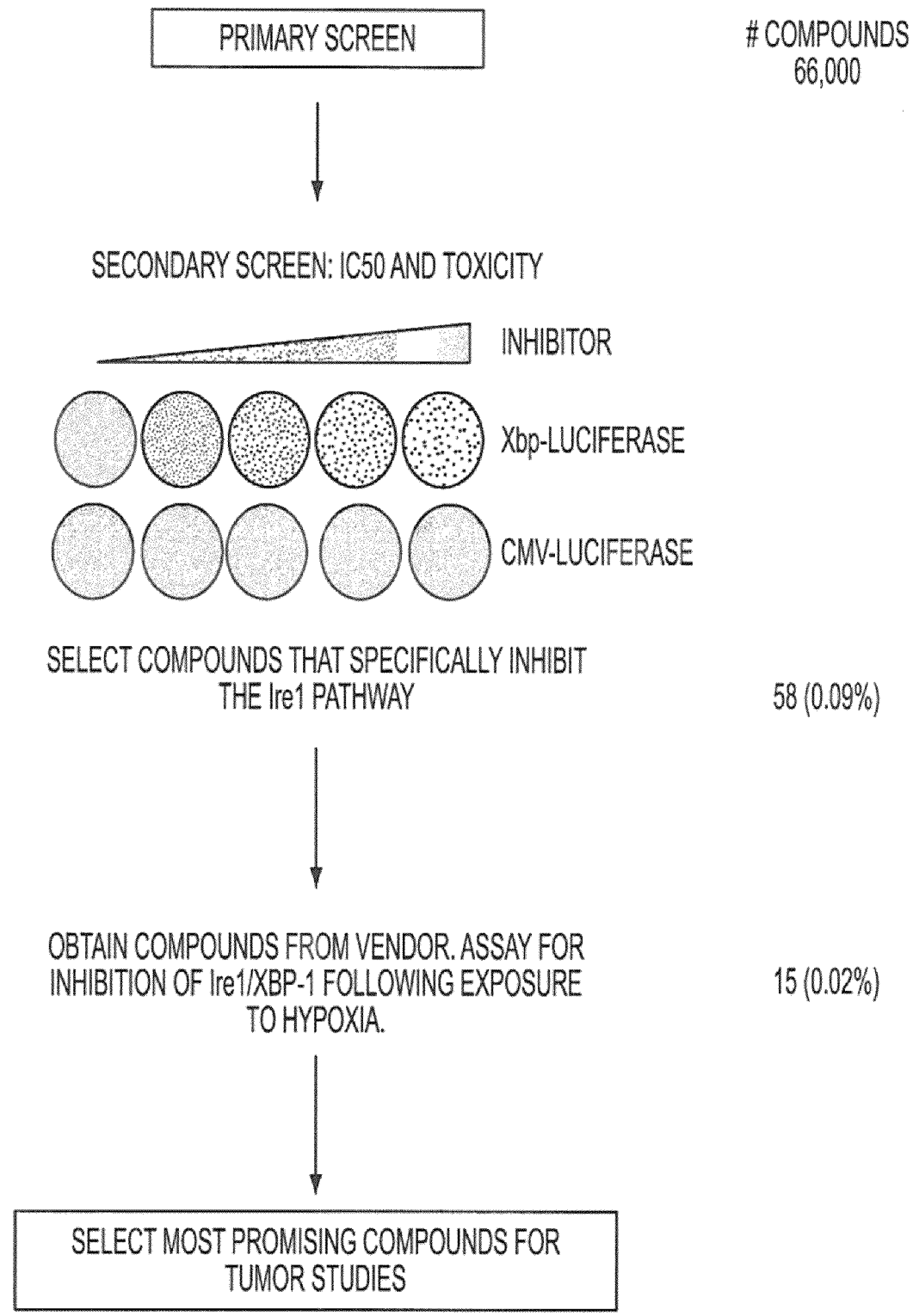
FIG. 3 is a schematic of an initial screen of a 66,000 small molecule library for specific inhibitors of XBP-1.

This resulted in 38 compounds that were then tested individually in five separate cell based assays including the following: 1) >95% inhibition of hypoxia-activated XBP1-luciferase reporter; 2) >95% inhibition of tunicamycin activated XBP1-luciferase reporter; 3) >95% inhibition of hypoxia induced UPRE-luciferase reporter (multimer of unfolded protein response element which XBP-1 can transactivate); 4) >95% inhibition of tunicamycin induced UPRE-luciferase reporter; and 5) inhibition of XBP-1 splicing by RT-PCR. To qualify for further testing, each compound must have satisfied 4/5 of the conditions described above. A total of 18 compounds, referred to as candidate irestatins, met these criteria and were identified for further testing as described below. The structure of each of these compounds is shown in Table 1, above. A schematic of this screen is shown in FIG. 3.

Figure 4:
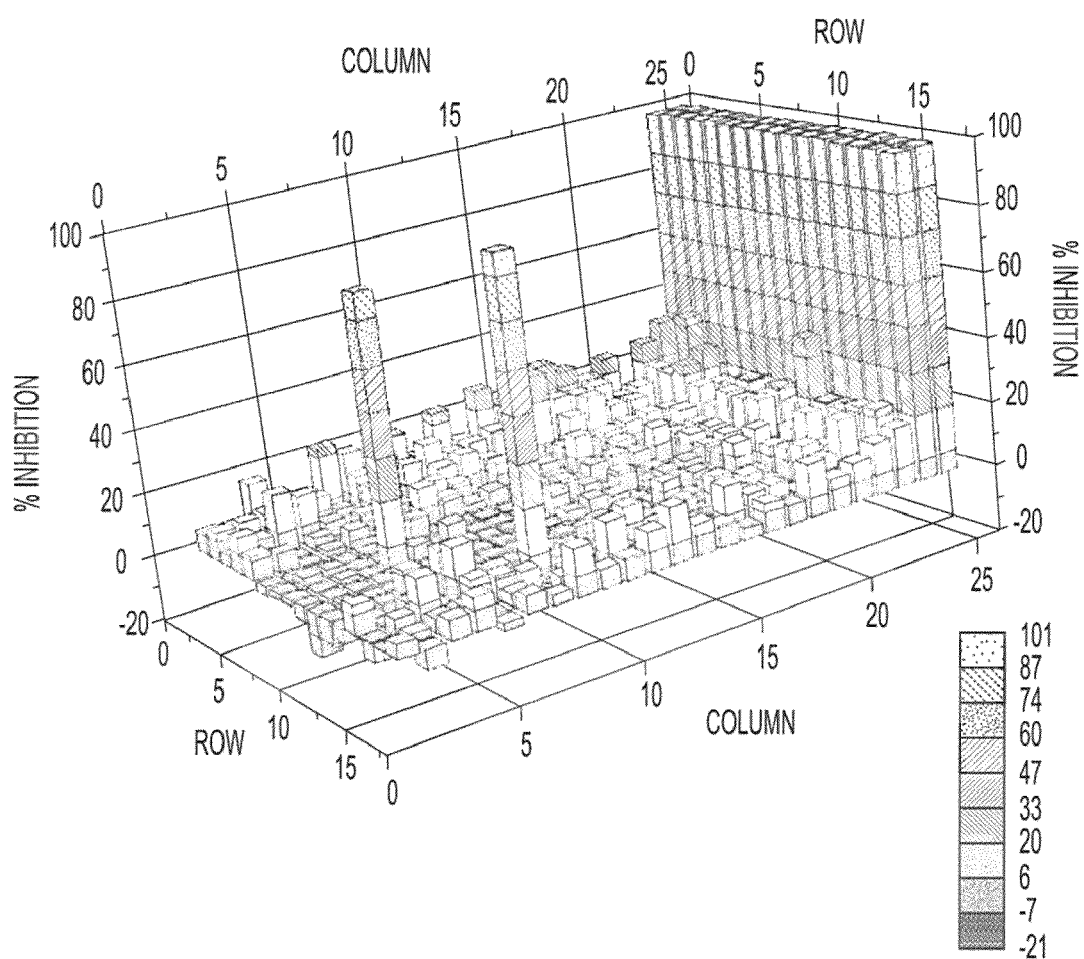
FIG. 4 shows a "heat map" view of a single plate from the primary screen for inhibitors of XBP-1.

A "heat map" view of a single plate from the primary screen is shown in FIG. 4. HT1080 cells stably expressing the XBP1-luciferase construct described above were plated in 384 well format (4,000 cells/well) and a different compound was added robotically into each individual well. Compounds were selected for further testing based upon demonstrating >95% inhibition of luciferase activity. The two lanes on the far left of FIG. 4 were negative controls (tunicamycin/thapsigargin alone) and the two lanes on the far right were positive controls (media alone).

FIG. 5A shows examples of compounds that were tested individually at 1 uM, 2 uM and 6 uM for inhibition of a UPRE-luciferase reporter following exposure to tunicamycin (Tm). In these studies, the luciferase reporter was under the control of 5 repeats of the XBP-1 promoter element (5×-UPRE). FIG. 5B shows compounds that were tested for inhibition of hypoxia (48 hours) induced transactivation of the same UPRE-luciferase report construct transiently transfected into HT1080 cells. More specifically, HT1080 fibrosarcoma cells transiently transfected with a luciferase reporter under the control of 5 repeats of the XBP-1 promoter element (5×-UPRE) were treated with 1 µM of each irestatin or left untreated, and incubated in normoxia or hypoxia (0.1% oxygen) for 48 hrs at 37° C. Cells were harvested, lysed in reporter lysis buffer, and assayed for luminescence using a luminometer. Fold induction is calculated as the luminesence in hypoxia divided by the normoxic luminescence value. The irestatin used is identified by a four-digit number below each bar.

Individual testing of the most promising compounds for inhibition of endogenous XBP-1 splicing (FIG. 6A) was also performed. In this assay, HT1080 cells were treated with hypoxia in the presence of various compounds and XBP-1 was amplified by RT-PCR. Not every compound inhibited XBP-1 splicing in this assay. Under aerobic conditions, only the unspliced form of XBP-1 XBP-1u) was detectable (lane 1). The spliced form of XBP-1 (XBP-1s) was detectable under hypoxia (lane 2). The ability of each individual compound to inhibit XBP-1 splicing was variable. In this set of compounds, only two were effective inhibitors of XBP-1 splicing (lanes 5 and 7). Interestingly, two compounds (lanes 3 and 4) resulted in inhibition of both the spliced and unspliced forms of XBP-1.

FIG. 6B shows the results of studies in which HT1080 fibrosarcoma cells stably expressing the XBP-luciferase reporter were treated with 1 uM of each irestatin or left untreated, and incubated in hypoxia (0.01% oxygen) for 48 hrs at 37° C. Cells were harvested, lysed in reporter lysis buffer, and assayed for luminescence using a luminometer.

Several of the candidate irestatins were tested in a hypoxia clonogenic survival assay. FIG. 7A is an example of some of the candidate irestatins that demonstrated selective sensitization of HT1080 cells to hypoxia. HT1080 fibrosarcoma cells stably were treated with 1 uM of the indicated irestatin or left untreated, and incubated in hypoxia (0.01% oxygen) for 48 hrs at 37° C. Cells were harvested and counted, and allowed to form colonies under normal oxygen tension. Survival rate is expressed as the fraction of colonies formed divided by the total number of cells seeded for each condition. For all experiments, cells were plated in triplicate, and all experiments were repeated at least three times. These experiments were repeated using MiaPaCa2 cells in place of the HT1080 fibrosarcoma cells. As shown in FIG. 7B, the three compounds shown in FIG. 7A also sensitized MiaPaca2 cells to hypoxia, indicating that even though the screen was performed in HT1080 cells, the results may be generalized to other cell types.

FIG. 7C shows results of experiments demonstrating that candidate irestatins inhibit survival of human tumor cells in hypoxia. PANC1 pancreatic adenocarcinoma cells were treated with 1 uM of the indicated irestatin or left untreated, and incubated in hypoxia (0.01% oxygen) for 48 hrs at 37° C. Cells were harvested and counted, and allowed to form colonies under normal oxygen tension. After 10-11 days, colony formation was analyzed by staining with crystal violet.

FIG. 8 shows the results of studies in which HT1080 fibrosarcoma cells were treated with 1 uM of each Irestatin or left untreated, and incubated in hypoxia (0.01% oxygen) for 24 hrs at 37° C. Cells were harvested, lysed, and analyzed by Western blot using anti-XBP-1 antisera (lower panel) or anti-HIF-1 antisera (top panel) to confirm hypoxia exposure. The results confirm that the tested irestatins inhibit IRE1 signaling and XBP-1 splicing during hypoxia.

Example 3

Inhibition of XBP-1 Splicing in Tumors by Inhibitors of IRE1 Activity

Several nude mice were implanted with HT1080 cells stably expressing a XBP-1s-luciferase construct and XBP-1 activation was examined using bioluminescence imaging. Imaging was performed using the In Vivo Imaging System (IVIS, Xenogen Corporation, Alameda, Calif.) in the Stanford Center for Innovation in In Vivo Imaging (SCI3). This device consists of a cooled CCD camera mounted on a light-tight specimen chamber. In these experiments, two different potential irestatins (3281 & 5500) were injected IP into nude mice implanted with HT1080 stably expressing XBP1s-luciferase (described in FIG. 2A). We estimated that injecting mice at a concentration of 50 mg/kg (no apparent toxicity) was within a 10-fold range of the in vitro drug concentrations used (assuming uniform distribution and ignoring excretion/metabolism) for the above described cell culture assays.

As shown in FIGS. 9A-D, XBP-1 splicing activity was undetectable 8 hrs after irestatin 3281 injection and became detectable within 16 hrs later. Following a second injection, XBP-1 splicing was again inhibited after 8 hrs. These data strongly indicate that this compound had a direct effect on the inhibition of XBP-1 splicing, and may be effectively employed in the treatment of solid tumors. A second candidate irestatin (5500) was tested in the same manner and did not have any affect on XBP-1 splicing, at least at the time points assayed.

Example 4

Inhibition of Tumor Growth In Vivo by Inhibitors of IRE1 Activity

The ability of inhibitors of the inventive inhibitors of IRE1 activity to inhibit tumor growth in vivo was examined in a mouse model as follows.

PANC1 pancreatic adenocarcinoma cells were implanted subcutaneously into nude mice. Mice were then given a bolus injection of one of the inventive irestatins (1401, 9337, 3611 or 9389) at a dose of 60 mg/kg every 48 hours for a total of 5 doses, with 5-7 tumors being treated per group. As shown in FIG. 10, significant tumor growth was observed in untreated mice, but not in mice treated with the irestatins. These results indicate that the inventive irestatins may be effectively employed to inhibit tumor growth in vivo.

Example 5

Identification and Characterization of Potent Inhibitors of the IRE1α/XBP-1 Pathway To date, the contribution of IRE1α to hypoxia tolerance and tumorigenesis has not been directly addressed and remains poorly understood. In this study, we employed a reverse chemical genetics approach to investigate the role of IRE1α in tumor growth. The use of small molecules to study protein function allows for the rapid and selective targeting of individual functions of multifunctional proteins, and serves as a powerful complement to conventional genetic strategies. Soderholm et al., *Nat Chem Biol* 2: 55-58 (2006). Indeed, genetic deletion in mice of IRE1α or XBP-1 causes embryonic lethality (Reimold et al., *Genes Dev* 14: 152-157 (2000); Harding et al., *Mol Cell* 7: 1153-1163 (2001)), and PERK and XBP-1 are required for the correct development of secretory organs such as the liver, pancreas and salivary gland (Lee et al., *Embo J* 24: 4368-4380 (2005); Zhang et al., *Cell Metab* 4: 491-497 (2006)). Thus, the UPR is necessary for the survival of tissues exposed to physiological levels of ER stress during fetal and postnatal development. The identification of small-molecule inhibitors provides an alternate strategy to inactivate IRE1α, enabling a functional analysis of this core UPR component in diverse cell types, including transformed cells cultured under hypoxia. This approach can also yield potential drug leads that may be utilized to address whether inactivation of a core UPR component can be tolerated in animals and applied as an antitumor strategy.

Materials and Methods

IRE1α Inhibitor Screen

As described above in Example 2, HT1080 fibrosarcoma cells stably expressing the XBP-luciferase reporter were plated in a 384 well microplate (4000 cells/well). After 24 hours, cells were treated with a mixture of tunicamycin (4 µg/ml) and thapsigargin (0.4 µM), followed by the addition of one compound per well (10 µM). We screened a total of 66,000 diverse molecules obtained from Specs, Chembridge and ChemRX. Twenty-four hours post-induction, BriteGlo luciferase substrate (10 µl) was added to each well and the signal intensity determined in a plate reader (0.2 s read per well). Hits were determined as compounds that significantly (>75%) inhibited activation of the XBP-luciferase signal by ER stress. We retested 431 compounds from the initial screen, and selected 58 compounds for additional analysis, including calculation of IC50 values and inhibition of a CMV-luciferase reporter. A total of 12 molecules, including irestatin 9389, exhibited potent and specific inhibition of IRE1α and were further characterized.

Plasmids, Cell Lines and Antibodies

The human fibrosarcoma cell line HT1080 and myeloma cell line RPMI-8226 were obtained from American Type Culture Collection (ATCC, Manassas, Va.). Cells were maintained at 37° C. with 5% $CO_2$ in DMEM (HT1080) or RPMI 1640 media (RPMI-8226 cells) supplemented with 10% fetal bovine serum and 1% penicillin-streptomycin antibiotics. Rabbit polyclonal antisera raised against human XBP-1 and phospho-IRE1α were a gift from Dr. Fumihiko Urano (University of Massachusetts, Worcester, Mass.). Additional antibodies were obtained from the following commercial sources: Grp78 (Stressgen); IRE1α, ATF6, and CHOP/GADD153 (Santa Cruz Biotechnology, Santa Cruz, Calif.); Flag M2 monoclonal (Sigma, St. Louis, Mo.); cleaved caspase 3, JNK1 and phospho-JNK1 (Cell Signaling Technologies, Danvers, Mass.); HIF-1α (Novus Biologicals, Littleton, Colo.); (hypoxyprobe and anti-pimonidazole antibody kits (Chemicon, Temecula, Calif.).

To generate the XBP-luciferase reporter, N-terminally Flag-tagged, unspliced human XBP-1 (amino acids 1-208) was amplified by PCR using Pfx polymerase (Invitrogen, San Diego, Calif.). The PCR product was digested with EcoRI and BamHI, and subcloned into pEGFP-N1 (Clontech, Mountain View, Calif.) to generate pFlag-XBP1(1-208)-EGFP. This plasmid was subsequently digested with BamHI and Not I to remove EGFP. Firefly luciferase containing BamHI and Not I sites was amplified by PCR and subcloned downstream of XBP-1 such that luciferase is translated only in the 'spliced' reading frame. All constructs were verified by sequencing.

Immunoblotting

Cells ($2 \times 10^6$) were cultured in 10-cm dishes, collected using a cell scraper at 4° C., and lysed by addition of 150 µl cell lysis buffer [50 mM Tris pH 7.4, 150 mM NaCl, 10% glycerol, 0.5% Triton X-100. 0.5% NP-40, 2 mM $Na_3VO_4$, 20 mM beta-glycerophosphate, 10 mM NaF, 1 mM DTT, 1 mM PMSF). Lysates were centrifuged for 5 min at 10,000×g, and proteins (~40 µg) were resolved by SDS-PAGE followed by semi-dry transfer to nitrocellulose membranes. Membranes were blocked in TBS-5% milk supplemented with 0.1% Tween-20. The blots were then probed overnight with relevant antibodies, washed, and incubated for 2 hours with species-specific secondary antibodies conjugated to horseradish peroxidase. After washing in block solution, immunoreactive material was detected by enhanced chemiluminescence (SuperSignal West Dura Extended, Pierce, Inc., Rockville, Ill.).

Reporter Assays

HT1080 cells stably expressing the XBP-luciferase construct were grown in 60 mm dishes to 60-70% confluency. Following hypoxia treatment, cells were washed twice with PBS, lysed in 400 µl× reporter lysis buffer (RLB) (Promega, Madison Wis.) for 30 min at 24° C. Lysates (100 µl) were mixed with an equal volume of luciferase substrate (Promega), and assayed using a luminometer. For 5×-UPRE-luciferase reporter assays, cells were co-transfected with the appropriate reporter plasmid and a control plasmid (pSV40-beta-gal) using Lipofectamine 2000 (Invitrogen, San Diego, Calif.). Twenty-four hours after transfection, fresh media was added, and cells were treated with Tm or shifted to hypoxia. After treatment, cells were lysed in 1×RLB and analyzed for luciferase activity as described above. Beta-galactosidase activity was determined using the beta-galactosidase enzyme assay system (Promega).

Northern Blots

Cells were cultured in 10 cm plates, harvested, and total RNA recovered with Trizol (Invitrogen, San Diego, Calif.). Total RNA (10 µg) was resolved on a 1% agarose-formaldehyde gel. $^{32}$P-labeled probes were prepared using the Rediprime II random-prime labeling kit (GE-Amersham, Buckinghamshire, UK). The primers used to PCR amplify probes are as follows. $P58^{IPK}$: 5'GTGGCCCCCGGCTC-CGTGACCAGCCGGCTGGGCTCGGTA 3' (SEQ ID NO: 4); 5' ACGCTTCAGTATTATCATTCT-TCAACTTTGACGCAGCTTT 3' (SEQ ID NO: 5). DER-1: 5' GTCGGACATCGGAGACTGGTTCAGGAG-CATCCCGGCGAT 3' (SEQ ID NO: 6); 5'TCCTACTGGGCAGCCAGCGGTA-CAAAAACTGAGGGTGTGG 3' (SEQ ID NO: 7). Blots were incubated with probe overnight, washed three times in 2×SSC/0.2% SDS, dried, and exposed to a phosphorimager screen overnight. Images were analyzed using ImageQuant software (Molecular Dynamics).

Ribonuclease Assay

The in vitro ribonuclease assays were carried out using purified IRE1α-cyto essentially as described. Gonzalez and Walter, Methods Mol Biol 160: 25-36 (2001); Gonzalez et al., Embo J 18: 3119-3132 (1999). For each reaction, 5 µg purified IRE1α-cyto was incubated with 300 ng of fluorescein-labeled RNA stem-loop substrate at 37° C. in a total volume of 300 µl. Aliquots (50 µl) were withdrawn at the indicated times and mixed with an equal volume of stop solution. Id. Reactions were analyzed by SDS-PAGE using 10-20% acrylamide gradient gels. The sequence for the hXBP-1 3' RNA stem-loop substrate is as follows: 5'CAGCACUCAGAC-UACGUGCACCUCUGCAGCAGGUGCAGGCCCAGUU G 3' (SEQ ID NO: 8). For the RNAse A cleavage assay, 300 ng of labeled XBP-1 RNA substrate were incubated with 1 ng bovine RNAse A (Sigma) in the presence of RNAsin (40 units), irestatin 9389 (2 µM) or DMSO vehicle control at 30° C. for the indicated times.

Mouse Immunohistochemistry and Histopathology

Tumor-bearing mice were injected i.p. with hypoxyprobe (50 mg/kg) 1 hour prior to sacrifice. Mice were euthanised under anesthesia by cervical dislocation, and tumors were surgically resected, embedded in OCT compound (Sakura Tissue Tek), and frozen at −80° C. Tumors were sectioned at 8 µm, fixed in 4% paraformaldehyde, and blocked in PBS-4% BSA. Tissue sections were incubated overnight in block solution containing antisera specific for hypoxyprobe (1:250) and cleaved caspase-3 (1:400). Slides were washed three times with block solution and incubated for 2 hours at room temperature with anti-mouse Alexa 488 or anti-rabbit Alexa 594 (Invitrogen, San Diego, Calif.). Slides were washed five times in block solution, and coverslips mounted with Permount supplemented with DAPI.

Complete blood counts (CBC's) and clinical chemistry panels were performed on blood obtained by cardiac puncture after euthanasia with $CO_2$. Gross necropsies were performed, all major viscera were harvested, fixed in 10% buffered neutral formalin, routinely processed for paraffin embedding, and stained with hematoxylin and eosin (H&E). Sections were analyzed by a board-certified veterinary pathologist (DMB).

Clonogenic Survival Assays

For hypoxia survival assays, cells were grown in 60 mm dishes until reaching at 50-70% confluence and shifted to hypoxia (0.1% $O_2$) for 48 hrs. Cells were trypsinized, counted using a hemocytometer, and replated in triplicate at 1,000-20,000 cells per plate in normal culture medium. After 10-12 days of growth under normal oxygen conditions, colonies were stained with 0.2% crystal violet in ethanol and counted. Survival values are expressed as the number of colonies divided by the total number of cells seeded for each condition, normalized to the plating efficiency under normal oxygen conditions. At least three independent experiments were performed.

Tumor Xenografts

Female 4-6 week-old SCID (B6.CB17) mice supplied by Stanford University Animal Facility were housed in the same facility (American Association of Laboratory Animal Care-approved) with 12 hour light cycles. Food and water were provided ad libitum. All experiments were approved by the institutional care and use committee. The potential toxicities of irestatin 9389 were examined in SCID mice injected i.p. once daily over 4 consecutive days with increasing doses of irestatin 9389 or vehicle control. A dosing regimen of 50-60 mg/kg, equal to 75% of the LD50 value, resulted in robust inhibition of IRE1α function without apparent toxicity. For xenografts, $2 \times 10^6$ HT1080 fibrosarcoma cells were resuspended in 50-75 μl PBS and injected s.c. in the dorsal flanks of host mice. When the implanted tumors reached a mean volume of 150 mm$^3$, mice were randomly assigned into different treatment groups. Mice were dosed by i.p. bolus injection with either vehicle (50% DMSO, 20% cremophor EL, 30% ethanol) or irestatin 9389 (50 mg/kg). Tumors (6-8 per group) were measured every 2-4 days with calipers. Tumor volume was calculated using the formula $[(W^2 \times L) \, 0.52]$ where W=width and L=length.

In Vivo Bioluminescence Imaging

HT1080 fibrosarcoma cells ($2 \times 10^6$) stably expressing the XBP-luciferase reporter were implanted s.c. into severe combined immune deficient (SCID) mice. Ten minutes prior to imaging, mice were injected i.p. with D-luciferin (150 mg/kg) solubilized in PBS. Optical bioluminescence imaging was performed using the IVIS charged-coupled device camera system (Caliper Life Sciences, Hopkinton, Mass.). Mice were imaged for 1-4 minutes per acquisition scan. Signal intensities were analyzed using Living Image software (Caliper).

Results and Discussion

FIG. 11 shows the identification of Irestatin 9389 as a potent inhibitor of the IRE1α/XBP-1 pathway. A. XBP-luciferase reporter construct. Firefly luciferase was inserted downstream of the IRE1α splice site in human XBP-1 to enable the conditional translation of luciferase under ER stress in an IRE1α-dependent manner. B. Selective inhibition of the XBP-luciferase reporter by irestatin 9389. HT1080 human fibrosarcoma cells stably expressing the XBP-luciferase reporter or CMV-luciferase were cultured in the presence of Tm (4 μg/ml) and Tg (0.4 μM) and irestatin 9389 at the indicated concentrations. After 24 hours, luciferase activity was analyzed in an automated plate reader. For each cell line, values are expressed as the percent inhibition of the median for Tm/Tg-treated wells, corrected for background. C. Structure of irestatin 9389. D. XBP-luciferase reporter assay. HT1080 cells stably expressing the XBP-luciferase reporter were exposed to Tm (4 μg/ml) for 24 hours or hypoxia (0.1% oxygen) for 24 or 48 hours, in the presence of DMSO or irestatin 9389 (1 μM) as indicated. Values are expressed as the fold increases over uninduced levels. E. 5x-UPRE reporter assay. HT1080 cells were co-transfected with 5x-UPRE luciferase and SV40-beta-gal reporter plasmids, followed by exposure to Tm or hypoxia as in D. For each condition, luciferase activity is normalized to beta-galactosidase expression levels as an internal control for transfection efficiency. F. Western immunoblot analysis of XBP-1s. HT1080 cells were left untreated (lane 2) or exposed to Tm (4 μg/ml) for 20 hours in the presence of DMSO vehicle (lane 1) or the indicated irestatins (2 μM; lanes 3-6). Cell lysates were resolved by SDS-PAGE and immunoblotting using antisera specific for XBP-1s (top panel) or actin and GAPDH (bottom panel) as loading controls. G. Irestatin 9389 blocks the accumulation of XBP-1s under hypoxic conditions. HT1080 cells were treated with DMSO or exposed to irestatin 9389 (2 μM; lane 3) in normoxia (N) or under hypoxia for 24 hours (H 24; lanes 2,3). Cells were harvested, lysed, and analyzed by immunoblotting with antisera specific for HIF-1α (top), XBP-1s (middle) or actin (bottom). H. Northern blot analysis of XBP-1s transcription targets. Cells were exposed to Tm (4 μg/ml) or hypoxia for 24 hours (H 24) in the absence or presence of irestatin 9389 (2 μM). Total RNA was analyzed by Northern blotting using radiolabeled probes specific for P58$^{IPK}$ or DER-1. Total rRNA is shown as loading control.

FIG. 12 shows that irestatin 9389 inhibits the endonuclease function of IRE1α. A. Irestatin 9389 does not modulate the expression of Grp78. HT1080 cells were exposed to DMSO vehicle (lane 1), irestatin 9389 (2.5 μM; lane 2) for 16 hours or Tm (5 μg/ml; lane 3) for 8 hours. Following treatments, cells were harvested, lysed, and analyzed by immunoblotting using anti-Grp78 antibody (top) or anti-actin (bottom) as a loading control. B. Effect of irestatin 9389 on IRE1α expression and kinase function. HT1080 cells were preincubated for 16 hours with either vehicle or irestatin 9389 (2.5 μM), followed by addition of Tm (5 μg/ml) for the indicated times. Cell lysates were analyzed by Western immunoblotting using anti-IRE1α (bottom) or anti-phospho-IRE1α antibodies (top). C. Effect of irestatins on JNK1 activation under ER stress. HT1080 cells were untreated (lane 1), exposed to TNF-α (10 ng/ml, 10 min), or Tm (4 μg/ml, 1.5 hrs) (lanes 3-8) following a 2 hour preincubation in the presence of vehicle (lane 3) or the indicated irestatins (2.5 μM; lanes 4-8). Lysates were analyzed by Western blot using antisera specific for phospho-JNK1 (top) or total JNK1 (bottom). D. Purification of IRE1α-cytosolic. 6x-His-IRE1α-cyto containing the IRE1α kinase and endonuclease was expressed in bacteria (lane 1) and isolated by Nickel resin affinity chromatography to >95% purity (lane 2). E. IRE1α endonuclease assay. Fluorescein end-labeled RNA minisubstrate (300 ng) corresponding to the downstream (3') human XBP-1 intron-exon cleavage site was incubated in the absence (lanes 1-3) or presence (lanes 4-9) of purified His6-IRE1α-cyto (5 μg), and exposed to either vehicle or irestatin 9389 (2.5 μM). The reactions were stopped at the indicated times and reaction aliquots were resolved by SDS-PAGE and visualized by UV illumination. F. Quantification of RNA cleavage kinetics. Results represent the mean from 3 independent experiments +/-SEM. G. RNAse A activity assay. Labeled XBP-1 RNA minisubstrate (300 ng) was exposed for the indicated times to RNAse A (1 ng) in the presence of either RNAse inhibitor (40 units), irestatin 9389 (2.5 μM), or vehicle only for the indicated times. Samples were analyzed as in (E).

FIG. 13 shows that exposure to irestatin 9389 induces apoptosis and impairs cell survival under hypoxia and ER stress. A. Effect of irestatin 9389 on PERK and ATF6 pathways. HT1080 cells were treated with vehicle alone (lanes 1-4) or 2.5 μM irestatin 9389 (lanes 5-8) and cultured under aerobic conditions for 18 hours (N) or shifted to hypoxia for the indicated times. Protein lysates were analyzed by Western blot analysis using antisera specific for ATF6 (top), CHOP/GADD153 (middle) or actin (bottom). Arrow indicates the cleaved, transcriptionally active form of ATF6. B. Cleavage of caspase-3 in irestatin-treated cells under hypoxia. HT1080 cells were cultured in normoxia (N) or under hypoxia for 36 hours (H 36) in absence or presence of irestatin 9389 (2.5 μM). Arrows indicate proteolytically cleaved caspase-3. C. Colony formation assay. HT1080 cells were treated as in B under normoxia (N) or hypoxia for 48 hours (H 48). Cells were harvested, counted, and allowed to grow under normal culture conditions for 11-12 days. Colonies were visualized with crystal violet staining. D. Quantification of clonogenic survival assay. Values represent the mean+/−SEM from at least 4 independent experiments. E. TUNEL staining of cells treated as in C. F. Quantification of TUNEL-positive cells. Values represent the mean+/−SEM from at least 3 experiments. G. HT1080 tet-off Flag-XBP-1s cells were cultured in the presence or absence of dox (1 μg/ml), followed by lysis and anti-Flag immunoblot. H. Rescue of irestatin-mediated cell death by enforced expression of XBP-1s. Tet-off XBP-1s cells were cultured with or without irestatin 9389 (2.5 μM) in the absence or presence of dox, under hypoxia for 48 hours (H 48). Cells were processed as in C, and colonies were visualized with crystal violet staining. I. Cell proliferation assays. Equal numbers (1×10$^5$) of HT1080 fibrosarcoma (left) or RPMI 8226 myeloma cells (right) were seeded on day 0, and cultured in the presence of vehicle control or irestatin 9389 at the indicated concentrations. Cells were harvested at the indicated times and counted by hemocytometer. Values represent the mean calculated from triplicate experiments +/−SEM.

FIG. 14 shows the in vivo antitumor activity of irestatin 9389. A. Irestatin 9389 impairs IRE1α activity in implanted tumor xenografts. Equal numbers (2×10$^6$) of XBP-luciferase or CMV-luciferase reporter cells were implanted s.c. into SCID mice. After one week, mice were treated with irestatin 9389 (50 mg/kg), followed by optical bioluminescence imaging. B. Inhibition of tumor growth by irestatin 9389. HT1080 s.c. tumor xenografts were established in SCID mice and allowed to reach a mean volume of 150 mm$^3$ before treatment. Irestatin 9389 (50 mg/kg) or vehicle control was administered q 2d by i.p. injection and continued for 2 weeks, for a total of 6 doses. Tumor volumes were calculated based on caliper measurements taken every 3-5 days. Data points represent the mean volume calculated from at least 7 tumors per group, with SEM shown in one direction. Mean mouse weights +/−SEM are shown in bottom graph. C.

Immunohistochemical analysis of tumor xenografts. Tissue sections prepared from cryo-preserved tumors following 3 doses with either vehicle control or irestatin 9389 were immunostained using hypoxyprobe (pimonidazole) or antisera specific for cleaved caspase-3. D. Quantification of tumor immunohistochemistry. At least 8 randomly chosen fields (>300 cells/field) per tumor were scored for pimonidazole and cleaved caspase-3 staining. A minimum of 3 tumors (250-300 mm$^3$ at harvest) were analyzed per treatment group. Values represent mean+/−SEM.

FIG. 15 shows the expression of XBP-1s in human pancreas tissue specimens. Tissues surgically recovered from normal pancreas, chronic pancreatitis, or pancreatic tumors were sectioned and stained using antisera specific for XBP-1s (400× magnification). Images were scored on the basis of staining intensity and quantified as shown in the table.

FIG. 16 shows the histopathological analysis of mouse pancreas and liver tissues. Pancreas and liver specimens recovered from mice treated with three doses of either vehicle (top) or irestatin 9389 (50 mg/kg; bottom) were sectioned and stained with hematoxylin and eosin.

Figure 11A:
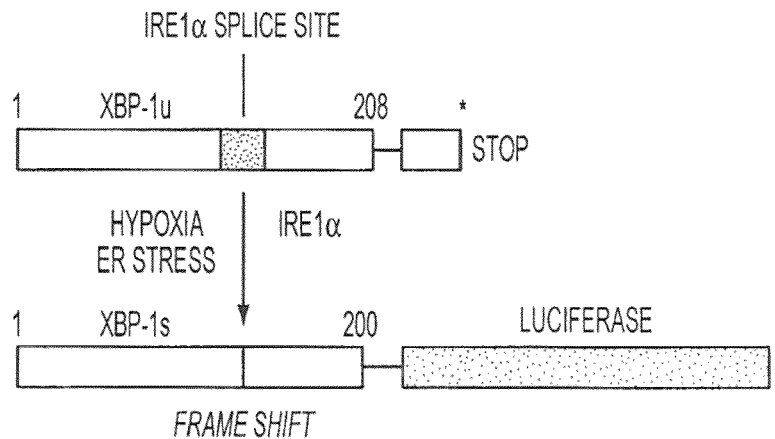
Figure 11B:
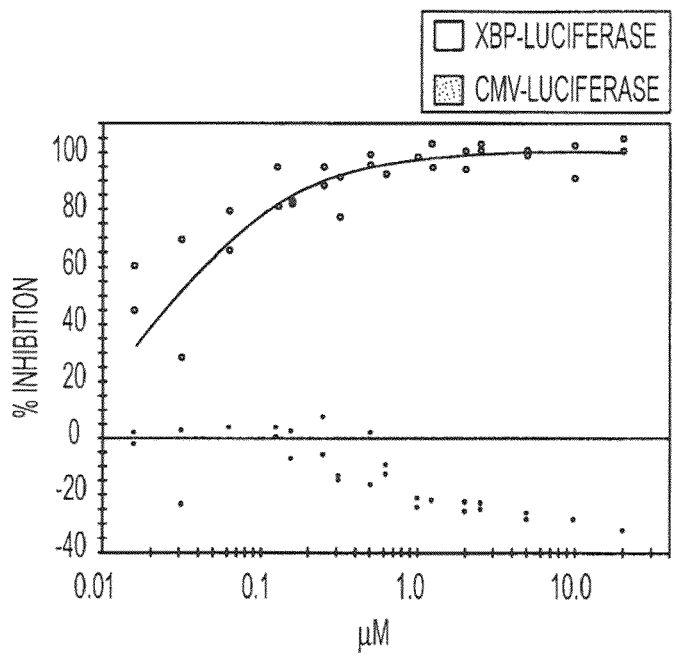
Figure 11C:
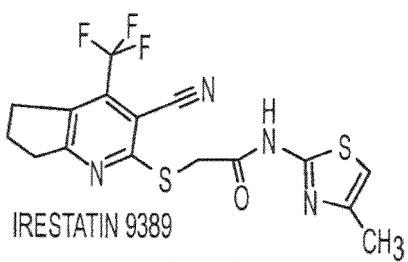

As described above, a HT1080 fibrosarcoma cell line stably expressing a fusion of unprocessed XBP-1 inserted upstream of firefly luciferase has been developed to identify small molecule inhibitors of the IRE1α/XBP-1 signaling module. Under ER stress conditions, IRE1α catalyzes the removal of a 26-nt intronic sequence from the XBP-1 mRNA, introducing a shift in reading frame that allows for the translation of luciferase (FIG. 11A). We screened a chemical library of 66,000 small molecules for inhibitors of XBP-luciferase activity stimulated by incubation of the reporter cell line with a mixture of tunicamycin and thapsigargin, two mechanistically distinct chemical inducers of ER stress. We also utilized a counterscreen consisting of HT1080 cells stably expressing a constitutively-expressed, CMV promoter-driven luciferase construct to exclude agents that caused non-specific inhibition of luciferase activity. We identified 12 molecules, termed irestatins, which consistently inhibited the IRE1α/XBP-1 signaling module without significantly affecting the activity of CMV-luciferase. We pursued several of the most potent irestatins, and describe here in detail our analysis of irestatin 9389, which inhibited XBP-luciferase activity with mean inhibitory concentration (IC50) of ~25 nM (FIG. 11B). The structure of this molecule is shown in FIG. 11C.

Figure 11D:
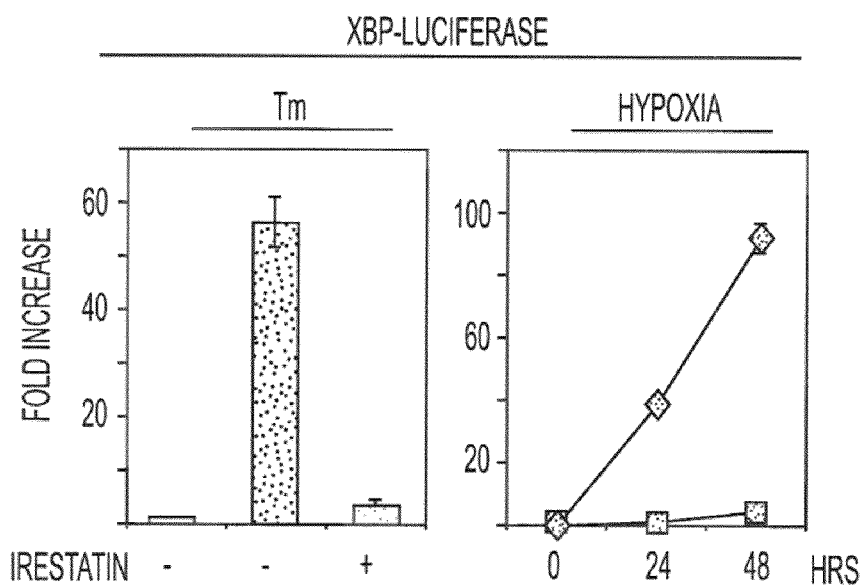

To determine if irestatin 9389 impairs IRE1α/XBP-1 signaling triggered by oxygen deprivation, we cultured XBP-luciferase reporter cells for 24 or 48 hours under hypoxia (<0.1% oxygen) in the absence or presence of irestatin 9389 (1 µM), and then assayed for luciferase activity. As a separate control, cells were also treated with Tm for 24 hours, which increased luciferase activity by 60-fold (FIG. 11D). As expected, exposure to irestatin 9389 inhibited Tm-mediated activation of the reporter by more than 90%. Exposure to irestatin 9389 also diminished activation of the XBP-luciferase reporter under hypoxia for 24 or 48 hours. Whereas control (DMSO-treated) cells increased XBP-luciferase activity by 95-fold after 48 hours of hypoxia, the addition of irestatin 9389 robustly inhibited this response (FIG. 11D, right panel).

Figure 11E:
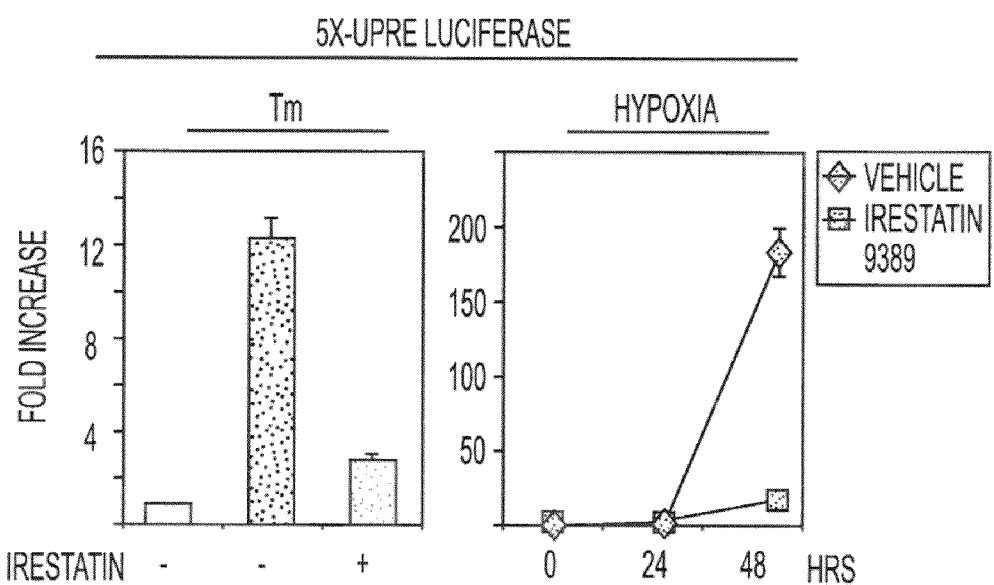
Figure 11F:
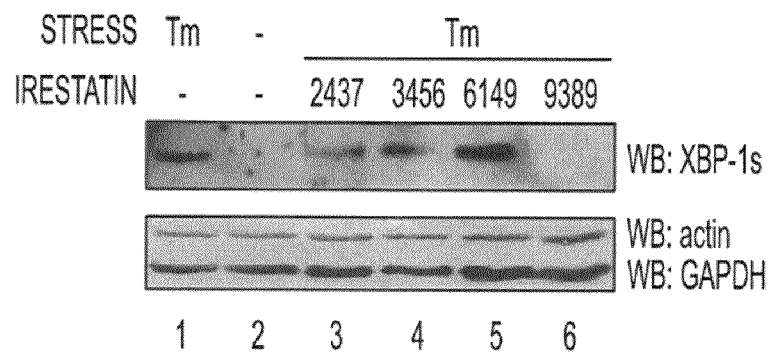
Figure 11G:
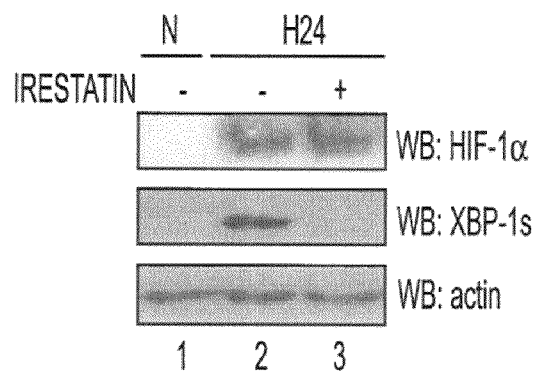

Since these assays employed a chimeric XBP-luciferase substrate, we next determined whether irestatin 9389 could inhibit the function of endogenous XBP-1s. HT1080 cells were transfected with a firefly luciferase reporter under the transcriptional control of 5 tandem repeats of the unfolded protein response element (5×-UPRE), a canonical DNA binding site for XBP-1s identified in the promoter regions of XBP-1 target genes. Yoshida et al., *Molecular & Cellular Biology* 20: 6755-6767 (2000); Yamamoto et al., *Journal of Biochemistry* 136: 343-350 (2004). Following exposure to Tm, luciferase activity increased by ~12-fold over untreated cells, while cells exposed to both Tm and irestatin 9389 exhibited less than a 4-fold induction (FIG. 11E). Irestatin 9389 also robustly inhibited UPRE promoter activity under hypoxic conditions. After 48 hours of hypoxia, vehicle-treated cells increased luciferase activity by 170-fold, while the addition of irestatin 9389 diminished this response by more than 90% (FIG. 11E, right panel). In support of these findings, western immunoblot analysis demonstrated that irestatin 9389 blocked the accumulation of XBP-1s following treatment with Tm, while structurally unrelated irestatin candidates exhibited little or no effect (FIG. 11F, lanes 3-5). Similarly, irestatin 9389 decreased levels of XBP-1s following 24 hours of hypoxia (FIG. 11G), while the expression of HIF-1α, a hypoxia-inducible transcription factor that functions independently of the UPR (Romero-Ramirez et al., *Cancer Research* 64: 5943-5947 (2004)), was not affected by irestatin 9389 (FIG. 11G, top panel).

Figure 11H:
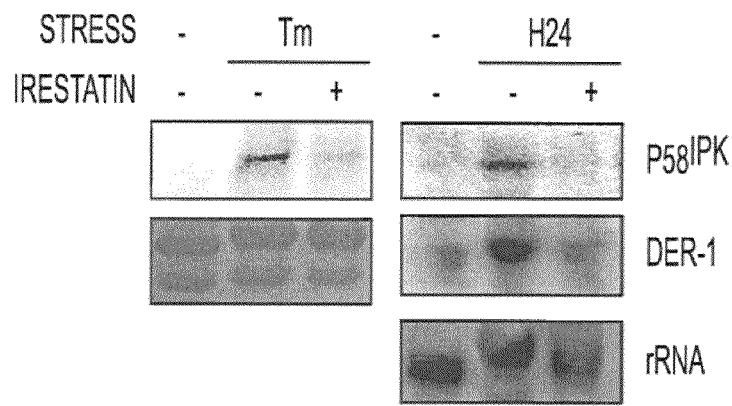

Gene expression profiling studies have identified several XBP-1-dependent target genes that are transcriptionally induced during ER stress. Lee et al., *Molecular & Cellular Biology* 23: 7448-7459 (2003). These include the DnaJ/Hsp40-like gene P58$^{IPK}$ and DER-1, a component of the ERAD pathway. Oda et al., *J Cell Biol* 172: 383-393 (2006). To analyze the effect of irestatin 9389 on the expression of these genes, HT1080 cells were treated with Tm or cultured under hypoxia for 24 hours, followed by isolation of total RNA and Northern blot analysis. Expression of these key UPR genes increased significantly (>5-fold) under hypoxia or following treatment with Tm, while the addition of irestatin 9389 fully inhibited this response (FIG. 11H). We conclude that irestatin 9389 specifically blocks the production or accumulation of XBP-1s following ER stress and diminishes the expression of its downstream effectors.

Figure 12A:
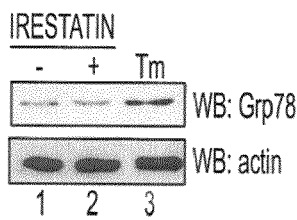
Figure 12B:
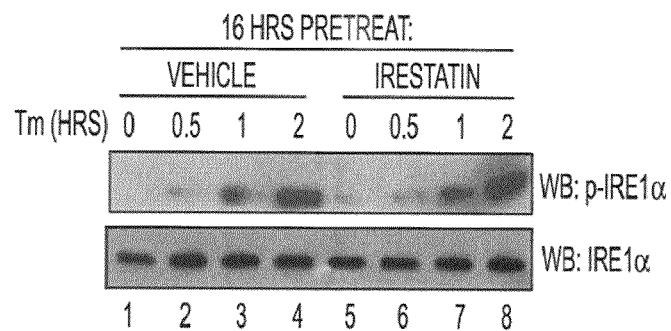

We next sought to determine the mechanism by which irestatin 9389 inhibits IRE1α/XBP-1 function. We first examined if irestatin 9389 deregulates the expression of Grp78, thereby increasing the fraction of Grp78-bound IRE1α and raising the activation threshold for IRE1α. Liu et al., *Journal of Biological Chemistry* 277: 18346-18356 (2002); Zhou et al., *Proc Natl Acad Sci USA* 103: 14343-14348 (2006); Bertolotti et al., *Nat Cell Biol* 2: 326-332 (2000). HT1080 cells were incubated with vehicle or irestatin 9389 (2.5 µM) for 16 hours, followed by western immunoblot analysis using Grp78 antisera. As a positive control, cells were treated with Tm for 8 hours, which robustly induced Grp78 (FIG. 12A, lane 3). In contrast, irestatin 9389 had no effect on Grp78 levels (FIG. 12A) at 16 hours or following longer treatments of 24 or 36 hours (data not shown). Similarly, cells incubated in the presence of irestatin 9389 for 16 hours exhibited no significant changes in the total level of IRE1α, as judged by Western immunoblotting (FIG. 12B, lower panel).

Figure 12C:
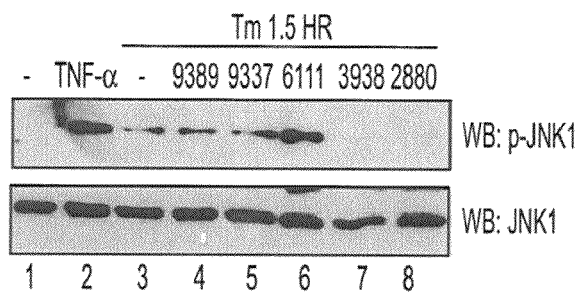

Activation of IRE1α is preceded by ATP binding and autophosphorylation, and the IRE1α kinase is required for endonuclease activity. Tirasophon et al., *Genes & Development* 14:2725-2736 (2000). To determine if irestatin 9389 inhibits the IRE1α kinase, HT1080 cells were preincubated for 16 hours with irestatin or vehicle followed by addition of Tm to induce ER stress. Cells were then harvested at regular intervals, and activation of the IRE1α kinase was assessed by immunoblotting using anti-phospho-IRE1α antisera. In both control and irestatin-treated cells, the addition of Tm triggered a rapid increase in levels of phospho-IRE1α (FIG. 12B). Preincubation with irestatin 9389 also failed to block the phosphorylation of JNK1, a downstream effector of IRE1α kinase signaling (Urano et al., *Science* 287: 664-666 (2000)), during Tm-induced ER stress (FIG. 12C). Interestingly, several structurally unrelated irestatins strongly inhibited the IRE1α-dependent phosphorylation of JNK1 under ER stress (FIG. 12C, lanes 7-8), indicating that mechanistically distinct classes of irestatins were identified by the initial screen.

Figure 12D:
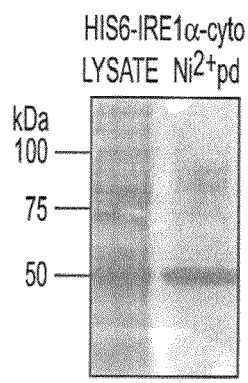
Figure 12E:
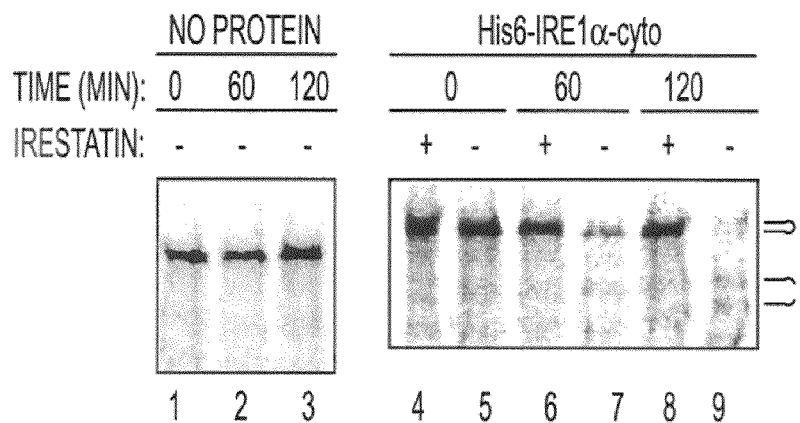
Figure 12F:
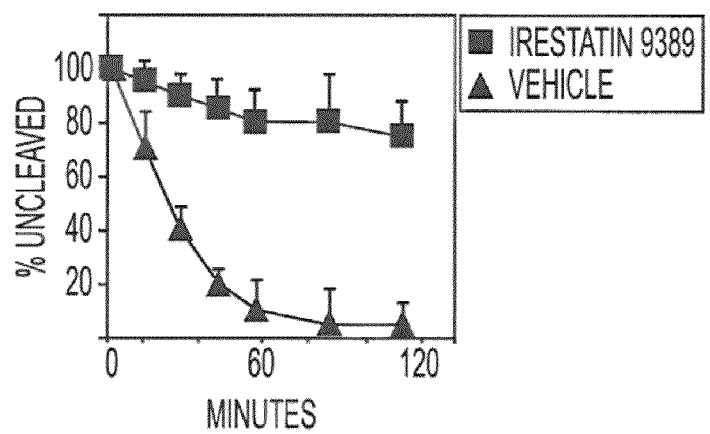
Figure 12G:
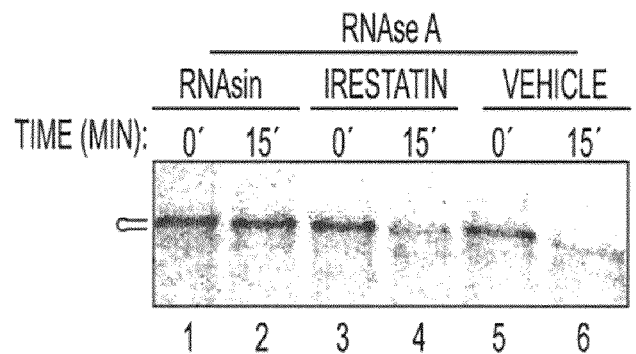

Next we determined whether irestatin 9389 inhibited the endonuclease function of IRE1α. To monitor endonuclease activity, we devised an in vitro ribonuclease assay in which a fluorescein labeled RNA hairpin corresponding to the 3' intron-exon boundary of human XBP-1 serves as a cleavage substrate for the IRE1α nuclease. Because the isolated IRE1α endonuclease lacks significant catalytic activity (Dong et al., *RNA* 7: 361-373 (2001); Nock et al., *Methods Enzymol* 342: 3-10 (2001); D.F. and A.K., unpublished data), we expressed in bacteria and purified the full cytosolic portion of IRE1α (His6-IRE1α-cyto) containing both kinase and endonuclease domains (FIG. 12D). In the presence of ATP and purified His6-IRE1α-cyto, the XBP-1 target RNA sequence was efficiently cleaved, with a mean half-life of 25 minutes (FIG. 12E). Addition of irestatin 9389 (2.5 µM) to the reaction strongly inhibited cleavage (FIG. 12E). However, irestatin is not a general ribonuclease inhibitor, as a >100-fold molar excess of irestatin 9389 failed to inhibit degradation of the XBP-1 3' intronic loop by RNAse A (FIG. 11G). Thus, irestatin 9389 functions as a selective inhibitor of the IRE1α endoribonuclease without impairing IRE1α kinase function.

Figure 13A:
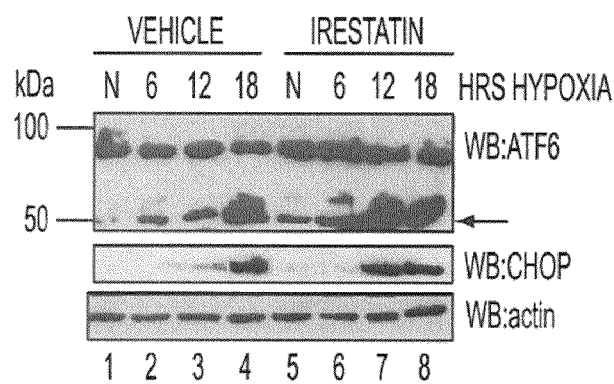
Figure 13B:
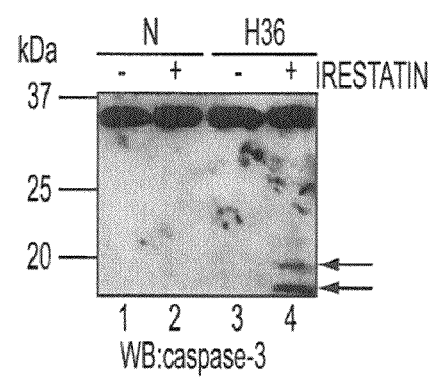

Activation of IRE1α alleviates ER stress through the splice-activation of XBP-1 and by the co-translational cleavage of mRNAs encoding secreted proteins. Hollien and Weissman, *Science* 313: 104-107 (2006). To assess the impact of inhibiting IRE1α signaling on the cellular response to ER stress, we performed a kinetic analysis of the two other major UPR pathways, ATF6 and PERK, in hypoxic cells exposed to irestatin 9389. Treatment of hypoxic cells with irestatin 9389 significantly increased the proteolytic cleavage of ATF6 into its transcriptionally active 50 kDa form (FIG. 13A, top). Likewise, the expression of CHOP/GADD153, a downstream target of the PERK-ATF4 signaling module, was increased in irestatin-treated cells following exposure to hypoxia for 6-12 hours (FIG. 13A, middle panel). As persistent activation of the PERK-ATF4-CHOP signaling module triggers apoptotic cell death (McCullough et al., *Molecular & Cellular Biology* 21: 1249-1259 (2001); Yamaguchi and Wang, *Journal of Biological Chemistry* 279: 45495-45502 (2004); Marciniak et al., *Genes & Development* 18: 3066-3077 (2004); Boyce et al., *Science* 307: 935-939 (2005)), we also examined the activation of caspase-3, the major apoptotic effector caspase, in irestatin-treated cells. Whereas vehicle-treated cells exhibited minimal activation of caspase-3 after 36 hours of hypoxia, exposure to irestatin 9389 stimulated cleavage of caspase-3 (FIG. 13B, lanes 3-4). This effect was specific to hypoxia-stressed cells, as irestatin 9389 had no effect on caspase-3 processing in cells cultured under normal oxygen conditions (FIG. 13B, lanes 1-2). Taken together, these findings indicate that irestatin 9389 overwhelms the adaptive capacity of the UPR, leading to initiation of programmed cell death.

Figure 13C:
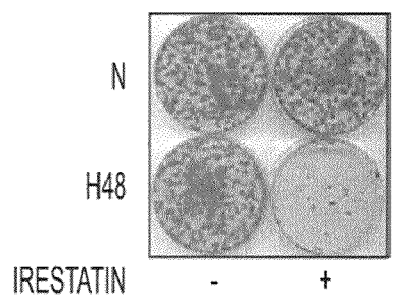
Figure 13D:
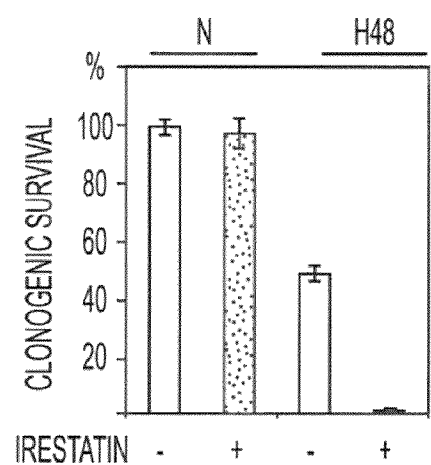
Figure 13E:
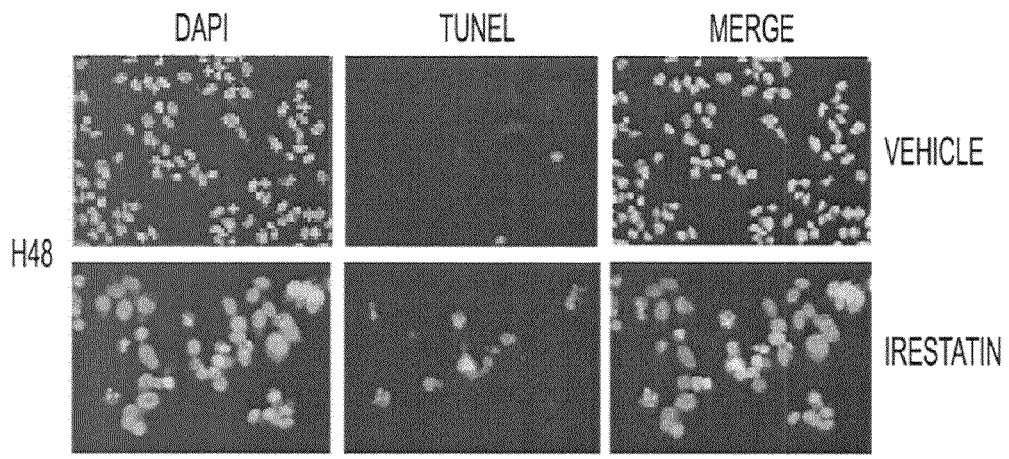
Figures 13F, 13G:
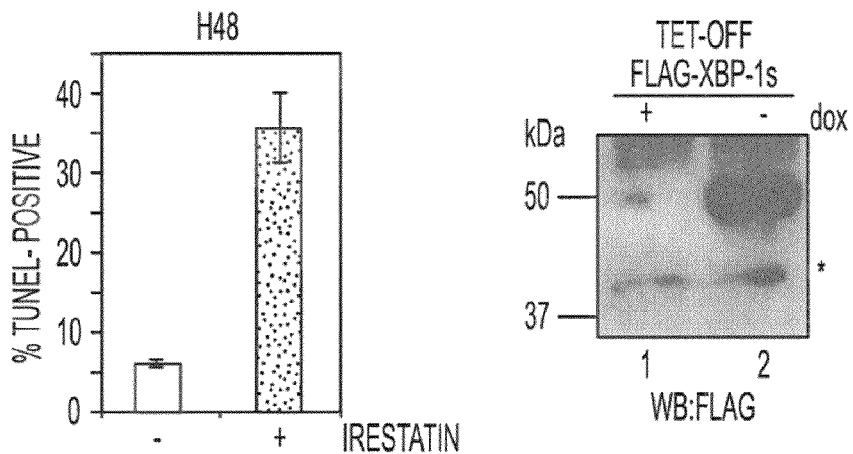

We corroborated these biochemical findings using colony formation assays as an indicator of cell viability. Addition of irestatin 9389 (2.5 µM) to the culture medium had a negligible effect on the survival of HT1080 cells cultured under normal oxygen conditions (FIG. 13C). However, in cells cultured under hypoxia for 48 hours, irestatin 9389 strongly inhibited colony formation (FIG. 13D). Exposure of hypoxic cells to irestatin 9389 for a shorter duration (hours 40-48 of hypoxia) also resulted in a 8-fold decrease in the rate of colony formation (data not shown). Consistent with the increased activation of caspase-3, treatment with irestatin 9389 significantly increased the proportion of hypoxic cells undergoing programmed cell death, as indicated by TUNEL-positive cells under hypoxia (FIG. 13E). After 48 hours of hypoxia, only 6% of vehicle-treated cells were TUNEL-positive, as compared with 35% of irestatin-treated cells (FIG. 13F).

Figure 13H:
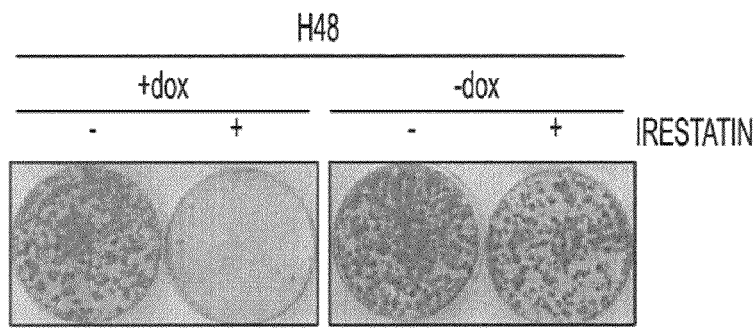
Figure 13I:
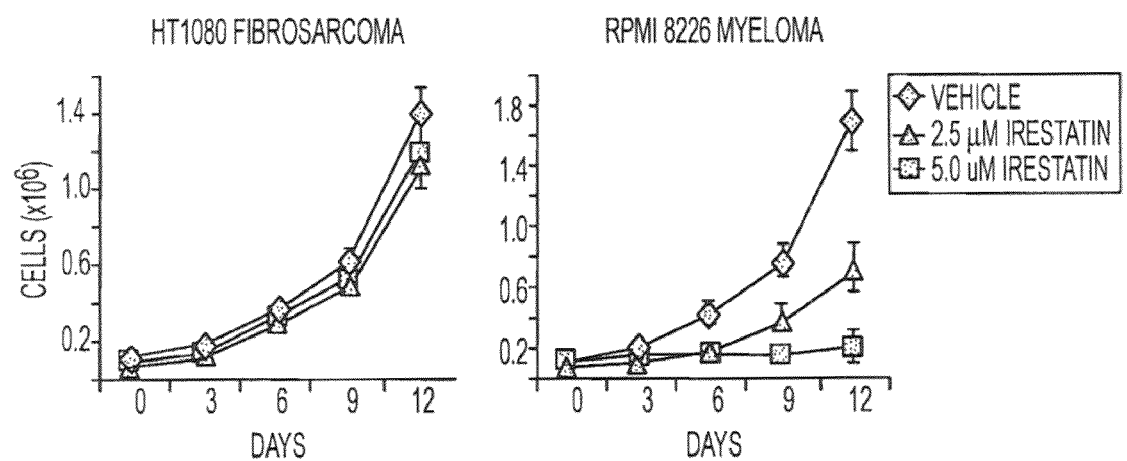

To determine if the irestatin-mediated inhibition of IRE1α/XBP-1s pathway accounts for decreased viability under hypoxia, we generated a cell line in which Flag-tagged XBP-1s is expressed under the control of a tetracycline-regulated promoter. Cells cultured in the presence of doxicycline (dox, 1 µg/ml) do not express Flag-XBP-1s, while removal of dox restores robust expression of Flag-XBP-1s (FIG. 13G). In the presence of both dox and irestatin 9389 (2.5 µM), we again observed a significant (~60 fold) decrease in viability following exposure to hypoxia for 48 hours. In contrast, the same concentration of irestatin 9389 had a minimal effect on the survival of hypoxic cells expressing Flag-XBP-1s (FIG. 13H). Thus, inhibition of the IRE1α/XBP-1s signaling module, and not an off-pathway effect of the irestatin, is primarily responsible for the poor survival of irestatin-treated tumor cells under hypoxia. Importantly, exposure to irestatin 9389 also strongly inhibited the growth of the myeloma cell line RPMI 8226, a secretory plasmacytoma, in a dose-dependent manner (FIG. 13I, right panel). In contrast, exposure to the same concentrations of irestatin 9389 had a negligible effect on the growth rate of HT1080 cells cultured under normal conditions (FIG. 13I, left panel). We conclude that irestatin 9389 selectively impairs the growth and survival of a variety of transformed cell types subjected to mechanistically distinct forms of ER stress.

Figure 14A:
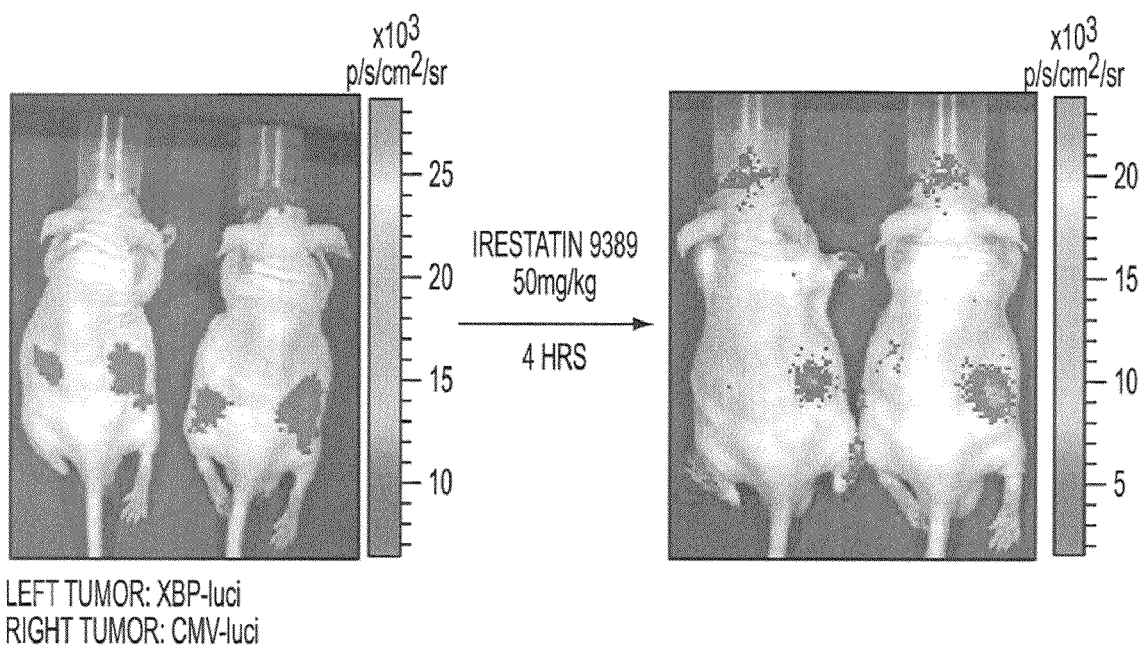

The increased sensitivity of irestatin-treated cells to hypoxic stress in vitro indicate that selective inhibition of IRE1α signaling could impact tumor growth. In support of an active role for IRE1α in tumor growth, we found that >50% (16/30) of surgically resected human pancreatic adenocarcinoma specimens exhibited moderate or strong immunoreactivity for XBP-1s. In contrast, XBP-1s was not detected in normal pancreas specimens (0/20), and infrequently observed in chronic pancreatitis (1/29) (FIG. 15). To explore the effects to irestatin 9389 in vivo, we first established animal dosing parameters using real-time bioluminescence imaging of SCID mice that had been implanted subcutaneously (s.c.) with tumor cells stably expressing the XBP-luciferase reporter. Irestatin 9389 administered in single doses of 50-60 mg/kg robustly inhibited the XBP-luciferase reporter for 6-8 hours after the injection (FIG. 14A). The XBP-luciferase signal returned to basal levels by 24 hours after treatment. A complete blood count and analysis of blood chemistry indicated that 3-4 doses of irestatin 9389 (50 mg/kg), administered every other day, were well tolerated and did not result in significant impairment of kidney, liver, or bone marrow function (Table 3). Although IRE1α has been implicated in glucose tolerance (Lipson et al., *Cell Metab* 4: 245-254 (2006); Ozcan et al., *Science* 306: 457-461 (2004)), we found no significant difference in fasting blood glucose levels between irestatin- and vehicle-treated animals (Table 3). These findings are further supported by histopathological analysis of all major organs, which revealed no significant differences between the vehicle and irestatin treatment groups. (FIG. 16).

TABLE 3

Analysis of blood chemistry and cell composition.
Vehicle-treated or irestatin-treated nude mice were euthanized with carbon dioxide, and a terminal cardiac blood draw performed. Blood was collected using a heparinzed syringe for CBC and clinical chemistries. Based on comparisons with the vehicle control mice, the only lesion that may be related to treatment is a mild leukopenia noted in both treated mice. The degree is mild and histologically, the bone marrow was not impacted.

|  | Vehicle | | Irestatin 9389 | |
| --- | --- | --- | --- | --- |
|  | mean | SEM | mean | SEM |
| Chemistry Panel | | | | |
| Glucose mg/dL | 112.5 | 20.56696 | 124.5 | 7.14 |
| AST IU/L | 107.6 | 22.92408 | 117.775 | 14.25 |
| ALT IU/L | 30 | 10.15513 | 29.4 | 6.68 |
| Total Bilirubin mg/dL | 0.525 | 0.287228 | 0.3 | 0 |
| Cholesterol mg/dL | 102.25 | 8.261356 | 102 | 8.8 |
| Electrolyte Panel | | | | |
| Sodium mM | 151.5 | 2.12132 | 152.25 | 1.89 |
| Potassium mM | 7.875 | 0.388909 | 7.5175 | 0.49 |
| Chloride mM | 116 | 1.414214 | 116.75 | 2.22 |
| Carbon Dioxide mM | 22.55 | 0.777817 | 25.075 | 0.71 |
| Na/K Ratio mM | 19.25 | 1.202082 | 20.325 | 1.36 |
| Anion Gap mM | 20.9 | 0.565685 | 17.975 | 0.71 |
| Complete Blood Count | | | | |
| WBC K/uL | 5.55 | 1.340398 | 5.19 | 1.23 |
| RBC M/uL | 9.8 | 0.583095 | 10.375 | 0.3 |
| HGB gm/dL | 13.75 | 0.818535 | 14.625 | 0.59 |
| HCT % | 43.9 | 2.946184 | 47 | 1.39 |
| Platelets K/uL | 574.5 | 159.9281 | 805.5 | 124.9 |

Figure 14B:
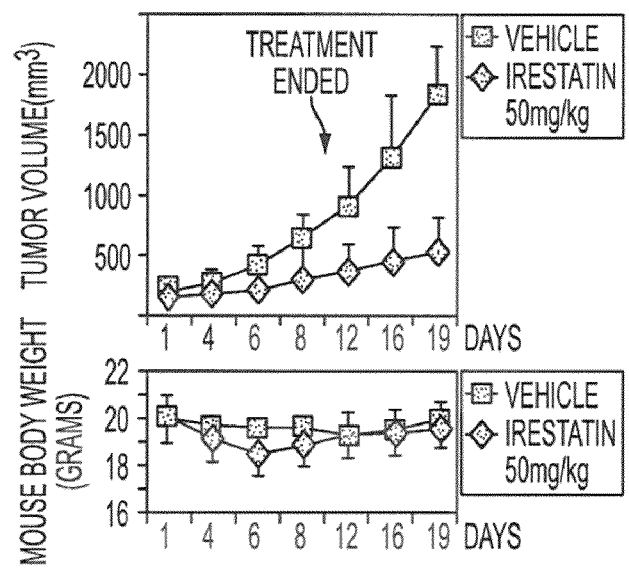

Next, we tested if treatment with irestatin 9389 could have a direct impact on tumor growth. Equal numbers ($2\times10^6$) of HT1080 cells were injected in the flanks of nude mice and allowed to grow for 2 weeks until tumors reached a mean volume of 150 mm. Mice were then randomly assigned into vehicle control or irestatin groups, and dosed by intraperitoneal (i.p.) injection of vehicle or irestatin 9389 (50 mg/kg) every other day for a total of 6 doses. Although this dosing regimen resulted in a transient inhibition of IRE1α, significant cytostatic antitumor effects were soon evident (FIG. 14B). The inhibition of tumor growth continued even after the final injection of irestatin 9389. One week after the last treatment, the mean volume of irestatin-treated tumors was significantly less than vehicle-treated tumors (1790+/−380 $mm^3$ versus 480+/−210 $mm^3$; P<0.01) (FIG. 14B). Irestatin-treated mice did not exhibit significant long-term weight loss compared to vehicle-treated mice (FIG. 14B, top).

Figure 14C:
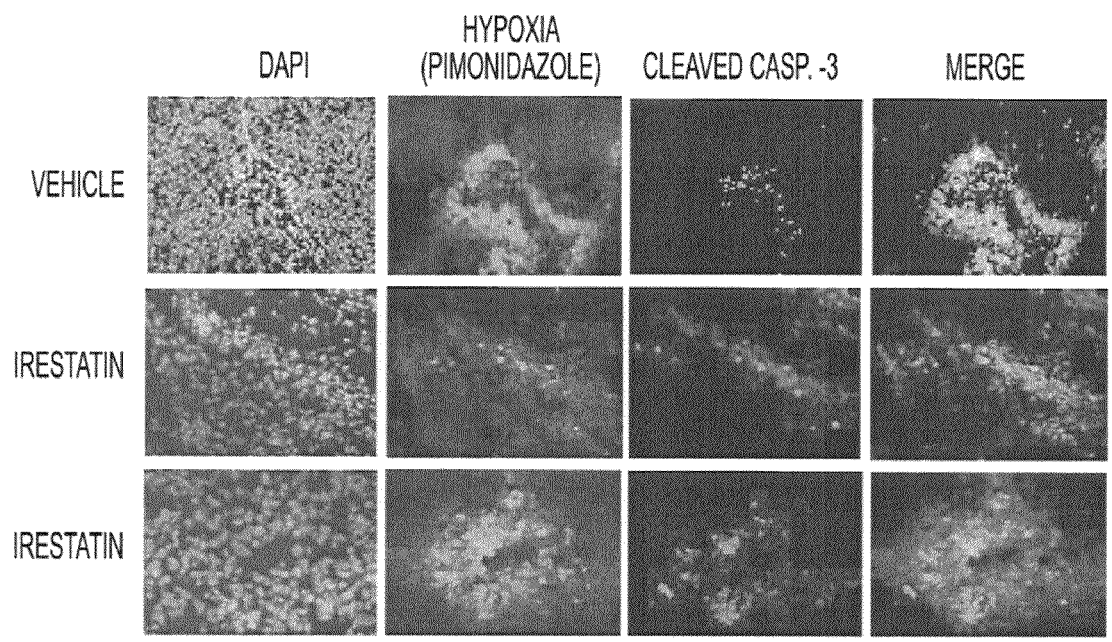
Figure 14D:
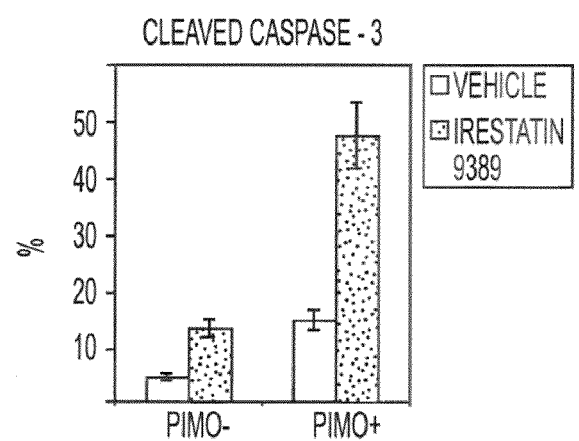

We further examined tumors from control and irestatin-treated mice for differences in cell survival. In tumors treated with three doses of irestatin 9389 (50 mg/kg), we observed a significant increase in cleaved caspase-3, an indicator of apoptosis, relative to vehicle-treated controls (FIG. 14C). The increase in apoptosis was most pronounced in hypoxic tissue regions of tumors, as determined by co-immunoreactivity for pimonidazole adducts (FIG. 14C, bottom panel). Quantitative analysis of immunostained tumor sections indicated that, in vehicle-treated tumors, less than 15% of hypoxic cells were apoptotic, compared to nearly 45% in irestatin-treated tumors (FIG. 14D). Interestingly, some pimonidazole-negative areas also exhibited increased levels of apoptosis following treatment with irestatin 9389, indicating that ER stress or sensitivity to irestatin occurs in tissue regions that are not acutely hypoxic (FIG. 14D). Taken together, these observations indicate that transient intratumoral inhibition of the UPR can potentiate cell death and impair tumor growth.

Severe hypoxia triggers the accumulation of misfolded proteins in the ER (Koumenis et al., *Molecular & Cellular Biology* 22: 7405-7416 (2002)), a potentially lethal condition that is remedied through the action of the UPR. In this study, we sought to determine the function of the IRE1α branch of the UPR in cellular tolerance to hypoxia and tumor growth. We employed a chemical genetic strategy to identify inhibitors of this pathway, and obtained multiple, mechanistically distinct classes of irestatins, including molecules that selectively target either the IRE1α kinase or endonuclease. We found that selective inactivation of the IRE1αendonuclease critically incapacitates the adaptive capacity of the UPR, resulting in increased ER stress and cell death under hypoxia. Irestatins therefore define a novel category of ER stress-selective antitumor agents specifically targeted to the underlying physiological response of tumor cells to the tumor microenvironment.

Several reports have demonstrated an essential role for the UPR in embryonic development, raising the possibility that systemic application of UPR-targeting molecules could cause severe toxicity to normal tissues, particularly those with secretory function such as the pancreas and liver. Iwakoshi et al., *Immunological Reviews* 194: 29-38 (2003); Reimold et al., *Genes Dev* 14: 152-157 (2000); Reimold et al., *Nature* 412: 300-307 (2001). However, we found that multiple bioactive doses of irestatin 9389 were well tolerated and did not result in acute injury to these organ systems, as indicated by analysis of blood chemistry and organ pathology. Without intending to be bound by theory, our observations are consistent with the finding that expression of XBP-1 in the liver rescues the embryonic lethality of XBP-1 deficient mice, indicating that most tissues can function adequately in the absence of this key UPR transcription factor. Lee et al., *Embo J* 24: 4368-4380 (2005). Likewise, deletion of PERK results in a multitude of developmental abnormalities, including hyperglycemia and atrophy of the exocrine pancreas. Harding et al., *Mol Cell* 7: 1153-1163 (2001). However, PERK is necessary for the development of insulin-secreting pancreatic beta cells specifically during the fetal and early neonatal period and is not required in adults to maintain beta cell functions or glucose homeostasis. Zhang et al., *Cell Metab* 4: 491-497 (2006). Without intending to be bound by theory, these findings indicate that the major UPR pathways are required in a subset of secretory tissues during temporally delimited developmental windows, and that inactivation of core UPR signaling modules using drug-like molecules can be well tolerated in mature animals.

Although individual UPR pathways are dispensable under most circumstances, we found that pharmacological inhibition of IRE1α significantly impaired the growth of implanted tumors. This finding reinforces the idea that tumors are subjected to significantly elevated levels of ER stress relative to the surrounding normal tissues, a condition that may arise through the distinct contrasts in oxygenation status between normal tissues and solid tumors. Hockel and Vaupel, *Seminars in Oncology* 28: 36-41(2001); Vaupel et al., *Methods in Enzymology* 381: 335-354 (2004). Without intending to be bound by theory, the antitumor effects of irestatin 9389 are consistent with a report demonstrating that inhibition of UPR target gene expression during glucose-deprivation can impair tumor growth. Park et al., *Journal of the National Cancer Institute* 96: 1300-1310 (2004). Without intending to be bound by theory, the rate of tumor growth may be naturally constrained by the severity of ER stress and by the capacity of the UPR to restore cellular homeostasis. Inhibition of this response induces proteotoxicity in hypoxic tumor cells, as indicated by the increased output of parallel UPR pathways downstream of ATF6 and PERK following treatment with irestatin 9389. In support of this model, irestatin 9389 potently blocks the induction of the XBP-1 targets DER-1 and P58$^{IPK}$, essential components of the ERAD machinery that mediate clearance of misfolded proteins from the ER. Ye et al., *Nature* 429: 841-847 (2004); Oyadomari et al., *Cell* 126: 727-739 (2006).

The pharmacological induction of ER proteotoxicity represents an effective therapeutic strategy in the treatment of solid tumors or secretory cell malignancies such as multiple myeloma, in which the UPR sustains cell viability under conditions of elevated secretory output. Iwakoshi et al., *Nat Immunol* 4: 321-329 (2003). Without intending to be bound by theory, since activation of the UPR can confer drug resistance to cancer cells (Gray et al., *Mol Pharmacol* 68: 1699-1707 (2005); Li and Lee, *Curr Mol Med* 6: 45-54 (2006)), our findings indicate that coordinated treatment with UPR-targeting agents may potentiate the efficacy of conventional chemotherapies. Inhibition of the UPR may also sensitize tumors to vascular targeting agents or anti-angiogenic drugs, which increase the fraction of hypoxic or nutrient-deprived tumor tissues (El-Emir et al., *Eur J Cancer* 41: 799-806 (2005); Boyle and Travers, *Anticancer Agents Med Chem* 6: 281-286 (2006); Dong et al., *Cancer Research* 65: 5785-5791 (2005)), or to radiation therapy, which preferentially kills oxygenated cell populations (Vaupel et al., *Medical Oncology* 18: 243-259 (2001); Vaupel et al., *Seminars in Oncology* 28: 29-35 (2001)). Likewise, proteasome inhibitors such as bortezomib (Velcade) have been shown to cause ER stress, while also inhibiting the UPR. Lee et al., *Proceedings of the National Academy of Sciences of the United States of America* 100: 9946-9951 (2003); Nawrocki et al., *Cancer Res* 65: 11510-11519 (2005); Obeng et al., *Blood* 107: 4907-4916 (2006). A combination of an irestatin and one or more proteasome inhibitors may exhaust the protective capacity of the UPR, pushing tumor cells into a decompensated state and ultimately cell death.

Example 6

Activity of Irestatins with 9389-Like Structure

Compounds of the screening library with structural similarity to compound 9389 (see Table 1) have been identified and in some cases further assayed for inhibitory activity. See Table 4. Compounds listed with "IC50" values were assayed secondarily after initially being identified in the high throughput screen. Each value represents a separate calculation of reporter inhibition based upon the high throughput robotic screening platform. The actual IC50 values are calculated and represent an estimate of the potency of each compound. This assay is not considered to be accurate below a concentration of 10 nM. Compounds classified with "mild" activity inhibited the XBP1-luciferase reporter by 10-30%. Compounds classified with "moderate" activity inhibited the XBP1-luciferase reporter by 30-75%. Compounds classified with "potent" activity inhibited the XBP1-luciferase reporter by 75-100%. Compounds classified with "undetected" activity inhibited the XBP1-luciferase reporter by less than 10% under the defined conditions.

Compounds with activities classified as "undetected" in Table 4 were identified by manual review of the structures of compounds reportedly present in the chemical libraries. Compounds displaying at least some structural similarity to the compounds with demonstrated activity are shown. The presence of these compounds in the assays has not been independently confirmed, however, so a lack of detectable activity may not necessarily be due to a compound's lack of activity.

TABLE 4

Activities of compounds having structural similarity to Compound 9389.

| Compound | STRUCTURE | IC50 Assay | Conc (uM) | % (uM) Inh | Activity Class |
|---|---|---|---|---|---|
| 1567 | 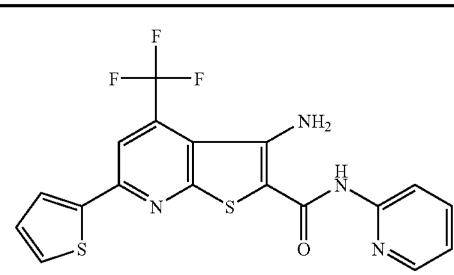 | HTS | | 10  −41.2 | undetected |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 2399 | 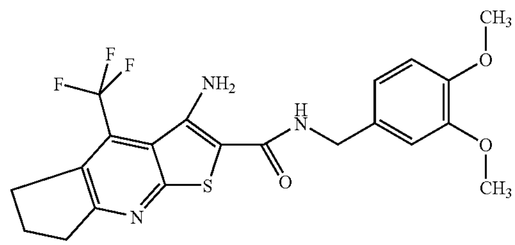 [SMILES: COc1ccc(CNC(=O)c2sc3nc4c(c(C(F)(F)F)c3c2N)CCC4)cc1OC] | HTS | | 10 | 13.3 | mild |
| 3290 | 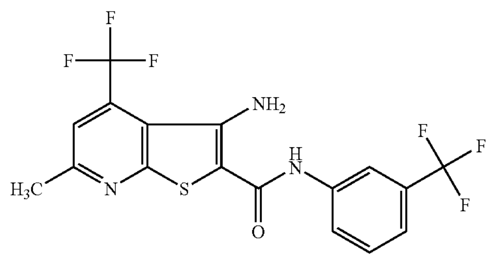 [SMILES: Cc1cc(C(F)(F)F)c2c(N)c(C(=O)Nc3cccc(C(F)(F)F)c3)sc2n1] | HTS | | 10 | −30.3 | undetected |
| 1491 | 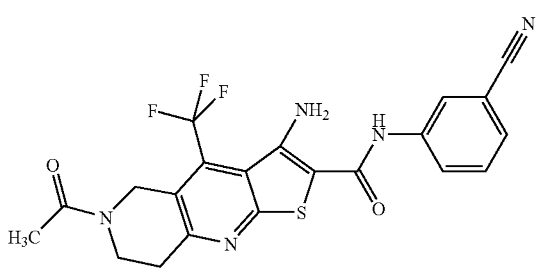 [SMILES: CC(=O)N1CCc2nc3sc(C(=O)Nc4cccc(C#N)c4)c(N)c3c(C(F)(F)F)c2C1] | HTS | | 10 | 11.0 | mild |
|  |  | HTS |  | 10 | 63.4 |  |
| 1740 | 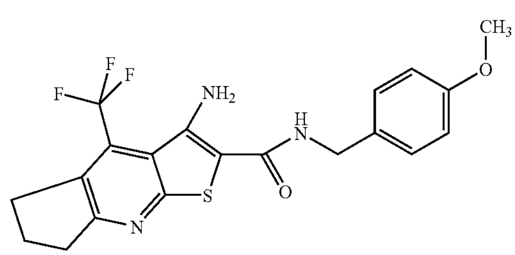 [SMILES: COc1ccc(CNC(=O)c2sc3nc4c(c(C(F)(F)F)c3c2N)CCC4)cc1] | HTS | | 10 | 25.1 | mild |
|  |  | HTS |  | 10 | 5.9 |  |
| 2750 | 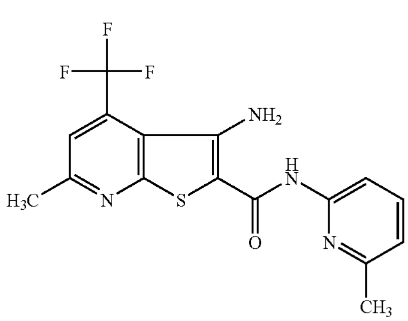 [SMILES: Cc1cccc(NC(=O)c2sc3nc(C)cc(C(F)(F)F)c3c2N)n1] | HTS | | 10 | 11.7 | mild |
|  |  | HTS |  | 10 | 16.6 |  |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 4335 | 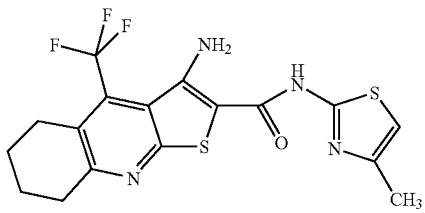 [SMILES: Cc1csc(NC(=O)c2sc3nc4c(c(C(F)(F)F)c3c2N)CCCC4)n1] | IRE IC50 | 0.09 | 20 | 67.4 | moderate |
| | | IRE IC50 | 6.30 | 20 | 70.4 | |
| 5500 | 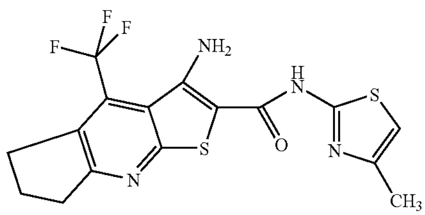 [SMILES: Cc1csc(NC(=O)c2sc3nc4c(c(C(F)(F)F)c3c2N)CCC4)n1] | IRE IC50 | 0.06 | 20 | 100.4 | potent |
| | | IRE IC50 | 0.000048 | 20 | 104.4 | |
| 8878 | 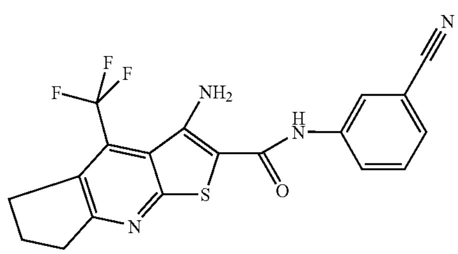 [SMILES: N#Cc1cccc(NC(=O)c2sc3nc4c(c(C(F)(F)F)c3c2N)CCC4)c1] | IRE IC50 | 0.023 | 20 | 72.4 | moderate |
| | | IRE IC50 | 5.14 | 20 | 50.0 | |
| 2853 | 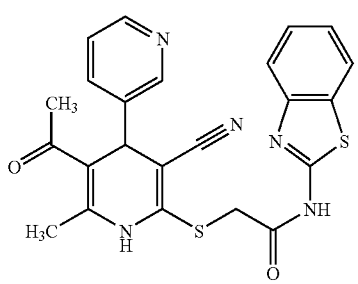 [SMILES: CC(=O)C1=C(C)NC(SCC(=O)Nc2nc3ccccc3s2)=C(C#N)C1c1cccnc1] | HTS | | 10 | 26.5 | mild |
| 3371 | 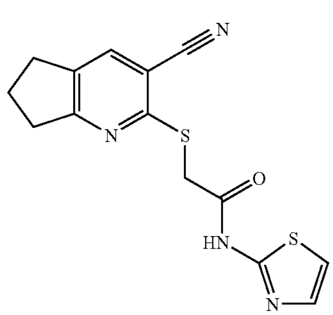 [SMILES: N#Cc1cc2c(nc1SCC(=O)Nc1nccs1)CCC2] | IRE IC50 | 13.90 | 20 | 72.6 | moderate |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 3398 | 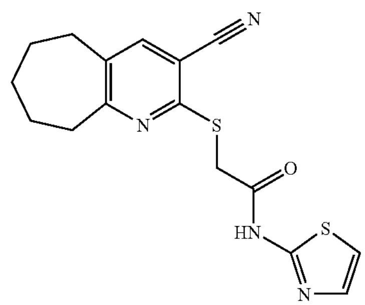 [SMILES: N#Cc1cc2c(nc1SCC(=O)Nc1nccs1)CCCCC2] | HTS | | 10 | −56.2 | undetected |
| 4645 | 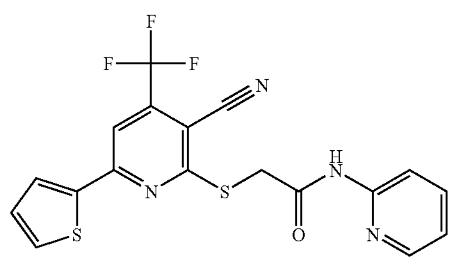 [SMILES: N#Cc1c(C(F)(F)F)cc(-c2cccs2)nc1SCC(=O)Nc1ccccn1] | HTS | | 10 | −8.3 | undetected |
| 4950 | 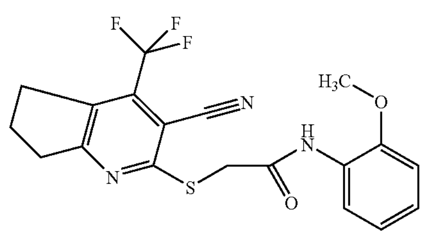 [SMILES: COc1ccccc1NC(=O)CSc1nc2c(c(C(F)(F)F)c1C#N)CCC2] | HTS | | 10 | −6.2 | undetected |
| 6392 | 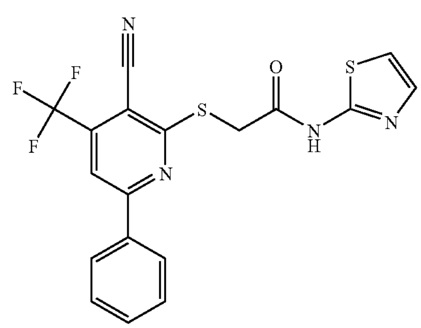 [SMILES: N#Cc1c(C(F)(F)F)cc(-c2ccccc2)nc1SCC(=O)Nc1nccs1] | HTS | | 10 | 2.7 | undetected |
| 6451 | 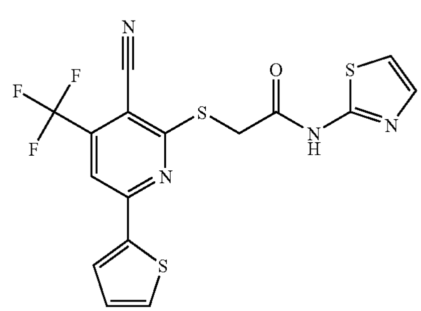 [SMILES: N#Cc1c(C(F)(F)F)cc(-c2cccs2)nc1SCC(=O)Nc1nccs1] | HTS | | 10 | −55.6 | undetected |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 8233 | 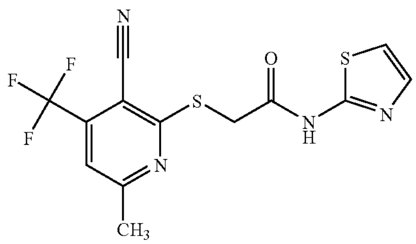 [SMILES: Cc1cc(C(F)(F)F)c(C#N)c(SCC(=O)Nc2nccs2)n1] | HTS | | 10 | −59.6 | undetected |
| 8920 | 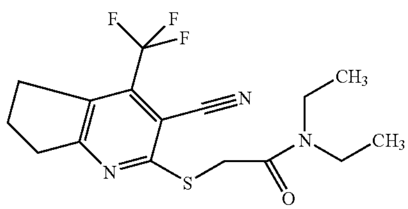 [SMILES: CCN(CC)C(=O)CSc1nc2c(c(C(F)(F)F)c1C#N)CCC2] | HTS | | 10 | 25.7 | mild |
| 9165 | 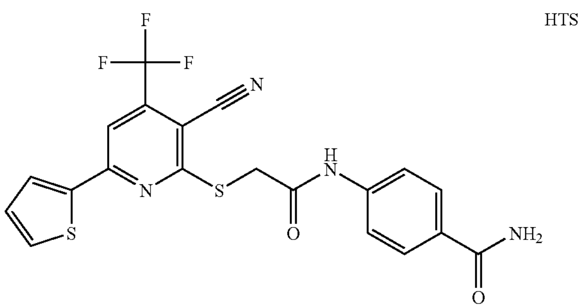 | HTS | | 10 | −6.5 | undetected |
| 9388 | 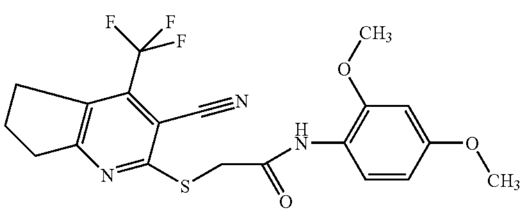 [SMILES: COc1ccc(NC(=O)CSc2nc3c(c(C(F)(F)F)c2C#N)CCC3)c(OC)c1] | HTS | | 10 | −40.8 | undetected |
| 9389 | 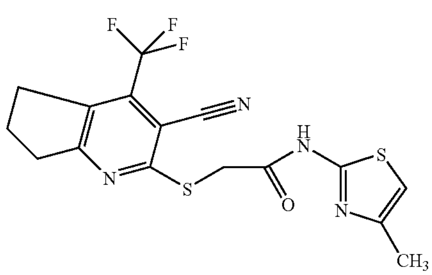 [SMILES: Cc1csc(NC(=O)CSc2nc3c(c(C(F)(F)F)c2C#N)CCC3)n1] | IRE IC50 | 0.0063 | 20 | 87.1 | potent |
| | | IRE IC50 | 0.031 | 20 | 100.3 | |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 9668 | 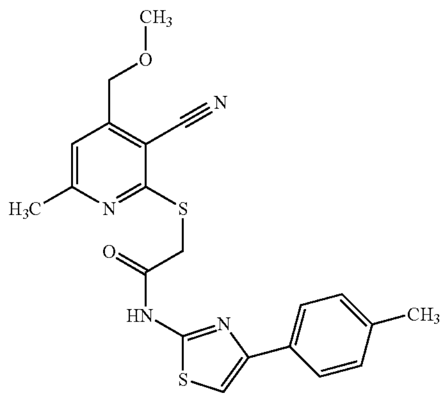 | HTS | | 10 | 19.0 | mild |
| 9766 | 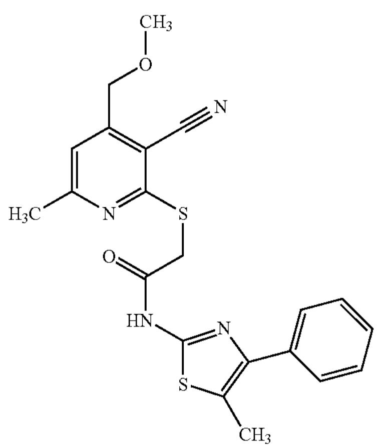 [SMILES: COCc1cc(C)nc(SCC(=O)Nc2nc(-c3ccccc3)c(C)s2)c1C#N] | HTS | | 10 | 26.7 | mild |
| 9787 | 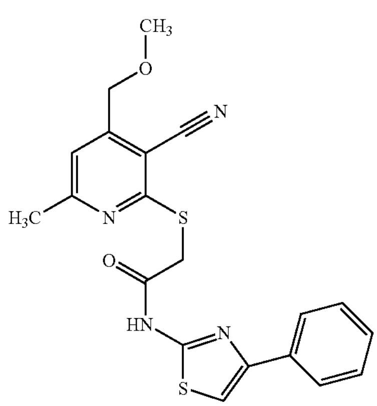 [SMILES: COCc1cc(C)nc(SCC(=O)Nc2nc(-c3ccccc3)cs2)c1C#N] | HTS | | 10 | −122.3 | undetected |

TABLE 4-continued

Activities of compounds having structural similarity to Compound 9389.

| Compound | STRUCTURE | Assay | IC50 (uM) | Conc (uM) | % Inh | Activity Class |
|---|---|---|---|---|---|---|
| 0040 | 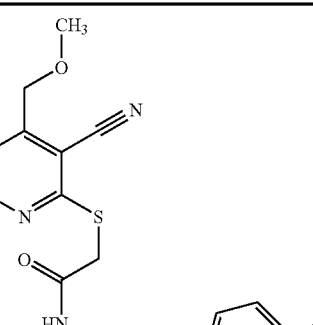 | HTS | | 10 | −4.6 | undetected |
| 0069 | 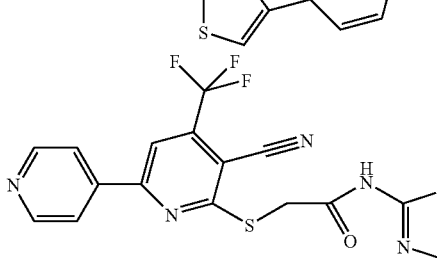 | HTS | | 10 | −5.4 | undetected |
| 6068 | 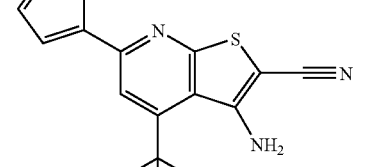 | HTS | | 12.3 | 5.8 | undetected |

From the foregoing, it will be appreciated that, although specific embodiments of the invention have been described herein for the purpose of illustration, various modifications may be made without deviating from the spirit and scope of the invention.

All references disclosed herein, including patent references and non-patent references, are hereby incorporated by reference in their entirety as if each was incorporated individually.

Those skilled in the art will recognize, or be able to ascertain using no more than routine experimentation, numerous equivalents to the specific method and reagents described herein. Such equivalents are considered to be within the scope of this invention and are covered by the following claims.

What is claimed is:

1. A compound represented by structural formula (I):

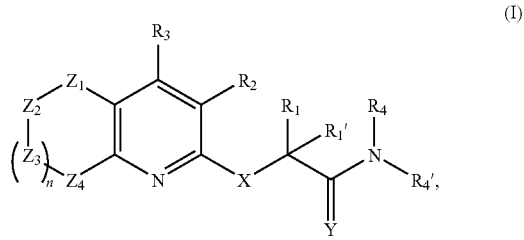

(I)

or a pharmaceutically acceptable salt thereof, wherein:
X is S;
Y is O or S;
$Z_1$, $Z_2$, $Z_3$, and $Z_4$ are independently $C(R_6)(R_6')$;
n is 0;
$R_1$, $R_1'$, $R_6$, and $R_6'$ are independently hydrogen, alkyl, halo, or cyano;
$R_2$ is alkyl;
$R_3$ is alkyl and is optionally substituted with 1-3 J groups;
$R_4$ is hydrogen;
$R_4'$ is selected from the group consisting of

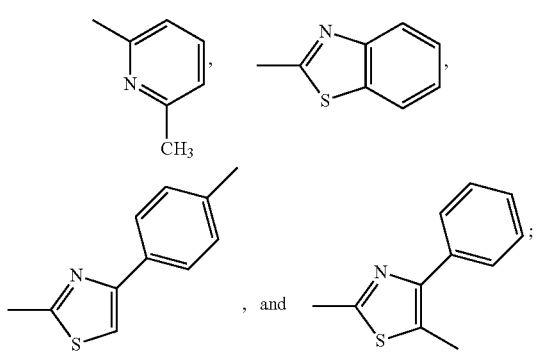

and J is one of alkyl or halo.

2. A pharmaceutical composition comprising a compound represented by structural formula (I):

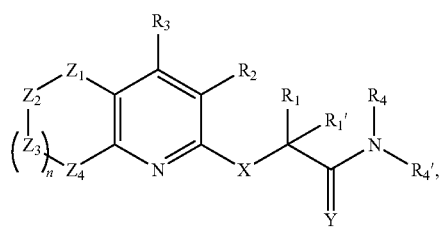

or a pharmaceutically acceptable salt thereof,
wherein:
X is S;
Y is O or S;
$Z_1$, $Z_2$, $Z_3$, and $Z_4$ are each $C(R_6)(R_6')$;
n is 0;
$R_1$, $R_1'$, $R_6$, and $R_6'$ are independently hydrogen, alkyl, halo, or cyano;
$R_2$ is alkyl or cyano;
$R_3$ is alkyl or haloalkyl and is optionally substituted with 1-3 J groups;
R4 is hydrogen;
R4' is selected from the group consisting of

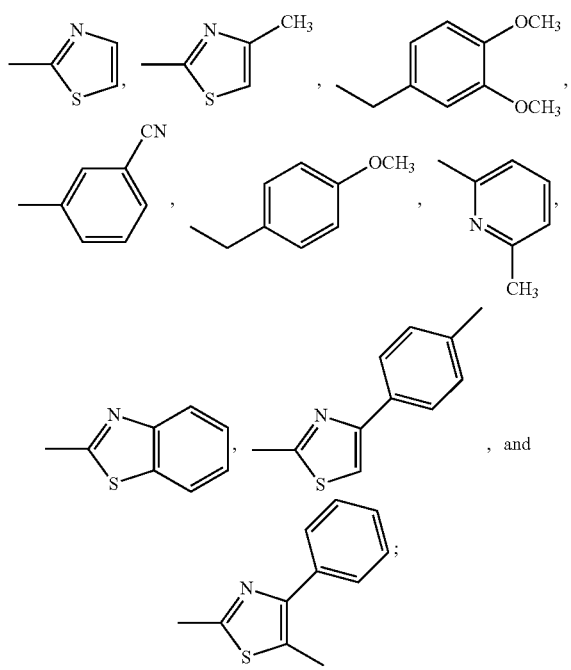

and J is one of alkyl or halo;
and a pharmaceutically acceptable carrier.

3. The pharmaceutical composition of claim 2, wherein: $R_6$ and $R_6'$ are both hydrogen.

4. The pharmaceutical composition of claim 2, wherein: Y is O.

5. The pharmaceutical composition of claim 2, wherein: $R_3$ is alkyl or haloalkyl.

6. The pharmaceutical composition of claim 5, wherein: $R_3$ is $CF_3$.

7. The pharmaceutical composition of claim 2, wherein: $R_1$ and $R_1'$ are both hydrogen.

8. The pharmaceutical composition of claim 2, wherein: $R_1$ and $R_1'$ are both hydrogen; and $R_2$ is CN.

9. The pharmaceutical composition of claim 8, wherein: $R_4'$ is

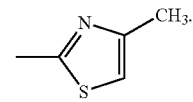

10. The pharmaceutical composition of claim 2, wherein: Y is O; $R_1$ and $R_1'$ are hydrogen; $R_2$ is CN; and $R_3$ is $CF_3$.

11. The pharmaceutical composition of claim 10, wherein: $R_6$ and $R_6'$ are both hydrogen.

12. The pharmaceutical composition of claim 2, wherein: Y is O; and $R_3$ is $CF_3$.

13. The pharmaceutical composition of claim 12, wherein: $R_6$ and $R_6'$ are both hydrogen.

14. The pharmaceutical composition of claim 2, wherein the compound is

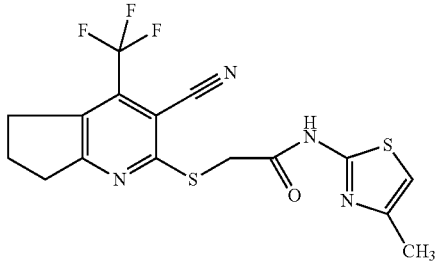 [SMILES: Cc1csc(NC(=O)CSc2nc3c(c(C(F)(F)F)c2C#N)CCC3)n1]

15. The pharmaceutical composition of claim 2, wherein $R_1$, $R_1'$, $R_2$, $R_3$, $R_4$, $R_4'$, $R_4''$, $R_5$, and J each independently contains 10 or fewer non-hydrogen atoms.

16. The pharmaceutical composition of claim 15, wherein $R_1$, $R_1'$, $R_2$, $R_3$, $R_4$, $R_4'$, $R_4''$, $R_5$, and J each independently contains 6 or fewer non-hydrogen atoms.

17. The pharmaceutical composition of claim 2 further comprising a chemotherapeutic agent.

18. The pharmaceutical composition of claim 17, wherein the chemotherapeutic agent is selected from the group consisting of bevacizumab, bortezomib, cetuximab, erlotinib, gemcitabine, cisplatin, oxaliplatin, etoposide, adriamycin, taxol, and thalidomide.

* * * * *